United States Patent
Chobanian et al.

(10) Patent No.: US 10,131,651 B2
(45) Date of Patent: Nov. 20, 2018

(54) [7,6]-FUSED BICYCLIC ANTIDIABETIC COMPOUNDS

(71) Applicant: Merck Sharp & Dohme Corp., Rahway, NJ (US)

(72) Inventors: Harry Chobanian, Aberdeen, NJ (US); Duane DeMong, Hanover, MA (US); Christopher W. Plummer, Hoboken, NJ (US); Minghai Fang, Shanghai (CN); Bin Hu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/328,913

(22) PCT Filed: Aug. 5, 2015

(86) PCT No.: PCT/CN2015/086108
§ 371 (c)(1),
(2) Date: Jan. 25, 2017

(87) PCT Pub. No.: WO2016/019863
PCT Pub. Date: Feb. 11, 2016

(65) Prior Publication Data
US 2017/0217942 A1    Aug. 3, 2017

(30) Foreign Application Priority Data

Aug. 8, 2014 (WO) ............... PCT/CN2014/084034
Aug. 5, 2015 (WO) ............... PCT/CN2015/086108

(51) Int. Cl.
| | |
|---|---|
| *C07D 405/14* | (2006.01) |
| *C07D 405/04* | (2006.01) |
| *C07D 405/10* | (2006.01) |
| *C07D 313/08* | (2006.01) |
| *A61K 45/06* | (2006.01) |
| *A61K 31/335* | (2006.01) |
| *A61K 31/397* | (2006.01) |
| *A61K 31/4427* | (2006.01) |
| *A61K 31/444* | (2006.01) |

(52) U.S. Cl.
CPC .......... *C07D 405/14* (2013.01); *A61K 31/335* (2013.01); *A61K 31/397* (2013.01); *A61K 31/444* (2013.01); *A61K 31/4427* (2013.01); *A61K 45/06* (2013.01); *C07D 313/08* (2013.01); *C07D 405/04* (2013.01); *C07D 405/10* (2013.01)

(58) Field of Classification Search
None
See application file for complete search history.

(56) References Cited

U.S. PATENT DOCUMENTS

| | | |
|---|---|---|
| 6,268,354 B1 | 7/2001 | Nishimura et al. |
| 8,030,354 B2 | 10/2011 | Brown et al. |
| 8,450,522 B2 | 5/2013 | Brown et al. |
| 2008/0090865 A1 | 4/2008 | Ge et al. |

FOREIGN PATENT DOCUMENTS

| | | |
|---|---|---|
| CN | 103012343 A | 4/2013 |
| CN | 103030646 A | 4/2013 |
| CN | 101106991 A | 1/2014 |
| EP | 0250265 B1 | 9/1990 |
| EP | 0388188 A1 | 9/1990 |
| GB | 2498976 A | 7/2013 |
| IN | 200702898 | 9/2007 |
| JP | 2008528590 A | 7/2008 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |

(Continued)

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.
Brown, S. P. et al., Discovery of AM-1638: A Potent and Orally Bioavailable GPR40/FFA1 Full Agonist, American Chemical Society, 2012, p. 726-730, vol. 3.
Du, Xiaohui, et al., Improving the Pharmacokinetics of GPR40/FFA1 Full Agonists, ACS Medicinal Chemistry Letters, 2014, p. 384-389, vol. 5, No. 4.

(Continued)

*Primary Examiner* — Samantha L Shterengarts
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

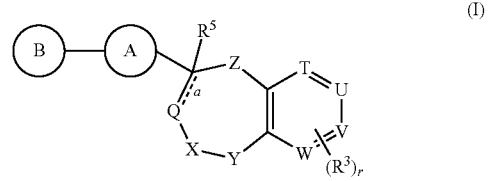

(I)

16 Claims, No Drawings

(56) References Cited

FOREIGN PATENT DOCUMENTS

| WO | WO2006083781 A1 | 8/2006 |
| --- | --- | --- |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | WO2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012011125 A1 | 1/2012 |
| WO | WO2012072691 A1 | 6/2012 |
| WO | WO2013104257 A1 | 7/2013 |
| WO | WO2013122028 A1 | 8/2013 |
| WO | WO2013122029 A1 | 8/2013 |
| WO | WO2013128378 A1 | 9/2013 |
| WO | WO2013178575 A1 | 12/2013 |
| WO | WO2014073904 A1 | 5/2014 |
| WO | WO2014078608 A1 | 5/2014 |
| WO | WO2014078609 A1 | 5/2014 |
| WO | WO2014078610 A1 | 5/2014 |
| WO | WO2014078611 A1 | 5/2014 |
| WO | WO2016019587 A1 | 2/2016 |
| WO | WO2016019863 A1 | 2/2016 |
| WO | WO2016022446 A1 | 2/2016 |
| WO | WO2016022448 A1 | 2/2016 |
| WO | WO2016022742 A1 | 2/2016 |

OTHER PUBLICATIONS

Executive Summary, Detection, Evaluation, and Treatment of High Blood Cholesterol in Adults (Adult Treatment Panel III), National Institutes of Health, 2001, pp. 1-40, NIH Publication No. 01-3670.

Ford, Earl, S. et al, Prevalence of the Metabolic Syndrome Amonh US Adults, JAMA, 2002, p. 356-359, vol. 287, No. 3.

Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Lou, J. et al., A Potent Class of GPR40 Full Agonist Engages the EnteroInsular Axis to Promote Glucose Control in Rodents, Plos ONE, 2012, p. 6-12, vol. 7, Issue 10.

Lu, H. et al., Discovery of novel orally bioavailable GPR40 agonists, Bioorganic & Medicinal Chemistry Letters, 2013, p. 2920-2924, vol. 23.

Negoro, Nobuyuki, et al., Discovery of TAK-875: A Potent, Selective, and Orally Bioavailable GPR40 Agonist, ACS Medicinal Chemistry Letters, 2010, p. 290-294, vol. 1, No. 6.

Suchand, B. et al., An efficient Intermolecular [Pd]-catalyzed C-C and intramolecular [Cu]-catalyzed C—O bonds formation: synthesis of functionalized flavans and benzoxepine, Tetrahedron Letters, 2012, p. 3861-3864, vol. 53.

Takano, Rieko, et al., Discovery of 3-aryl-3-ethoxypropanoic acids as orally acitve GPR40 Agonists, Bioorganic & Medicinal Chemistry Letters, 2014, p. 2949-2953, vol. 24.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Wang, Y. et al., Discoveryand Optimization of Potent GPR40 Full Agonists Containing Tricyclic Spirocycles, ACS Medicinal Chemistry Letters, 2013, p. 551-555, vol. 4.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

[7,6]-FUSED BICYCLIC ANTIDIABETIC COMPOUNDS

CROSS-REFERENCE TO RELATED APPLICATIONS

This application is a U.S. National Phase application under 35 U.S.C. § 371 of Chinese PCT Application No. PCT/CN15/086108, filed on Aug. 5, 2015, which claims priority from and the benefit of Chinese PCT Patent Application No. PCT/CN14/084034, filed Aug. 8, 2014.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body, however patients have a resistance to the effects of insulin in stimulating glucose and lipid metabolism in the insulin-sensitive muscle, liver and adipose tissues. Type 2 diabetes patients often have normal levels of insulin, and may have hyperinsulinemia (elevated plasma insulin levels), as they compensate for the reduced effectiveness of insulin by secreting increased amounts of insulin. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia is associated with increased and premature morbidity and mortality. Abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670). Patients with Metabolic Syndrome have an increased risk of developing the macrovascular and microvascular complications that occur with Type 2 diabetes, such as atherosclerosis and coronary heart disease.

There are several available treatments for Type 2 diabetes. Physical exercise and a reduction in dietary intake of calories are the recommended first-line treatment of Type 2 diabetes and of pre-diabetic conditions associated with insulin resistance, however compliance is generally poor. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The two best known biguanides, phenformin and metformin, cause some correction of hyperglycemia, but can also induce lactic acidosis and nausea/diarrhea. PPAR gamma agonists, such as rosiglitazone and pioglitazone, are modestly effective in reducing plasma glucose and Hemoglobin A1C. However, the currently marketed glitazones do not greatly improve lipid metabolism and may negatively effect on the lipid profile. The administration of insulin secretagogues, such as the sulfonylureas (e.g. tolbutamide, glipizide, and glimepiride) can result in hypoglycemia; their administration must therefore be carefully controlled.

There has been a renewed focus on pancreatic islet-based insulin secretion that is controlled by glucose-dependent insulin secretion. This approach has the potential for stabilization and restoration of β-cell function. Several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be advantageous, because long term diabetes therapy often leads to the gradual diminution of islet activity; after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight.

There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/011125, WO 2012/072691, WO2013/104257, WO 2013/122028, WO 2013/122029, WO 2013/128378, WO 2013/178575, WO 2014/073904, WO 2014/078608, WO 2014/078609, WO 2014/078610, WO 2014/078611, U.S. Pat. No. 8,030,354, U.S. Pat. No. 8,450,522, CN 103030646, CN 103012343, and GB 2498976.

GPR40 agonists are also disclosed in Negoro et al., ACS Medicinal Chemistry Letters (2010), 1(6), 290-294; Walsh et al., Bioorganic & Medicinal Chemistry Letters (2011), 21(11), 3390-3394; Zhou et al., Bioorganic & Medicinal Chemistry Letters (2010), 20(3), 1298-1301; Houze et al., Bioorganic & Medicinal Chemistry Letters (2012), 22(2), 1267-1270; Lu et al., Bioorganic & Medicinal Chemistry Letters (2013), 23(10), 2920-2924; Takano et al., Bioorganic & Medicinal Chemistry Letters (2014), 24(13), 2949-2953; Tan et al., Diabetes (2008), 57(8), 2211-2219; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; Houze et al., Abstracts of Papers, 243rd ACS National Meeting & Exposition, San Diego, Calif., USA Mar. 25-29, 2012, MEDI-265; Wang et al., ACS Medicinal Chemistry Letters (2013), 4(6), 551-555; and Du et al., ACS Medicinal Chemistry Letters (2014), 5(4), 384-389.

SUMMARY OF THE INVENTION

The present invention relates to novel substituted compounds of structural formula I:

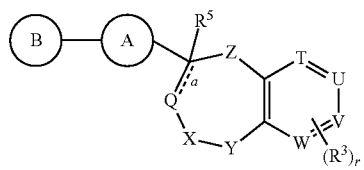

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

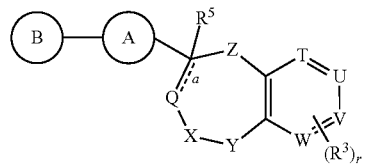

or a pharmaceutically acceptable salt thereof; wherein
"a" is a single bond or a double bond, provided that if "a" is a double bond, then $R^5$ and $R^6$ are absent and Q is selected from the group consisting of: C—$R^4$, —C—O$C_{1-6}$alkyl, and N, and further provided that if "a" is a single bond, then $R^5$ and $R^6$ are present and Q is selected from the group consisting of:
  (1) oxygen,
  (2) sulfur,
  (3) —$CR^4R^6$,
  (4) S(O)$_2$,
  (5) C=O,
  (6) —C($R^9$)O$C_{1-6}$alkyl, and
  (7) —N$R^c$;
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;

W is selected from the group consisting of:
(1) CH,
(2) N, and
(3) N-oxide,
provided that no more than two of T, U, V and W are selected from N and N-oxide, further provided that if both T and W are N or N-oxide, then $R^3$ is absent, and further provided that both U and V are not N or N-oxide;

X is selected from the group consisting of:
(1) oxygen,
(2) sulfur,
(3) —$CR^9R^9$,
(4) $S(O)_2$,
(5) C=O,
(6) —$C(R^9)OC_{1-6}$alkyl, and
(7) —$NR^c$,
provided that if Q is oxygen, sulfur or —$NR^c$, then X is not oxygen, sulfur or —$NR^c$, further provided that if Q is C=O, then X is not C=O or $S(O)_2$, and further provided that if Q is $S(O)_2$, then X is not $S(O)_2$, C=O, oxygen or sulfur;

Y is selected from the group consisting of:
(1) oxygen,
(2) sulfur,
(3) —$CR^9R^9$,
(4) $S(O)_2$,
(5) C=O,
(6) —$C(R^9)OC_{1-6}$alkyl, and
(7) —$NR^c$,
provided that if X is oxygen, sulfur or —$NR^c$, then Y is not oxygen, sulfur or —$NR^c$, further provided that if X is C=O, then Y is not C=O or $S(O)_2$, and further provided that if X is $S(O)_2$, then Y is not $S(O)_2$, C=O, oxygen or sulfur;

Z is selected from the group consisting of:
(1) oxygen,
(2) sulfur,
(3) —$CR^9R^9$,
(4) $S(O)_2$,
(5) C=O,
(6) —$C(R^9)OC_{1-6}$alkyl, and
(7) —$NR^c$;

A is selected from the group consisting of:
(1) aryl,
(2) heteroaryl,
(3) $C_{3-6}$cycloalkyl, and
(4) $C_{2-5}$cycloheteroalkyl,
wherein A is unsubstituted or substituted with one to five substituents selected from $R^a$;

B is selected from the group consisting of:
(1) hydrogen,
(2) aryl,
(3) aryl-O—,
(4) aryl-$C_{1-10}$ alkyl-,
(5) aryl-$C_{1-10}$ alkyl-O—,
(6) $C_{3-6}$cycloalkyl,
(7) $C_{3-6}$cycloalkyl-$C_{1-10}$alkyl-,
(8) $C_{3-6}$cycloalkyl-$C_{1-10}$alkyl-O—,
(9) $C_{3-6}$cycloalkenyl,
(10) $C_{3-6}$cycloalkenyl-$C_{1-10}$alkyl-,
(11) $C_{3-6}$cycloalkenyl-$C_{1-10}$alkyl-O—,
(12) $C_{2-5}$cycloheteroalkyl,
(13) $C_{3-6}$cycloheteroalkyl-$C_{1-10}$alkyl-,
(14) $C_{3-6}$cycloheteroalkyl-$C_{1-10}$alkyl-O—,
(15) heteroaryl,
(16) heteroaryl-O—,
(17) heteroaryl-$C_{1-10}$ alkyl-, and
(18) heteroaryl-$C_{1-10}$ alkyl-O—,
wherein B is unsubstituted or substituted with one to five substituents selected from $R^b$;

$R^1$ and $R^2$ are each independently selected from:
(1) a bond,
(2) hydrogen,
(3) halogen,
(4) —$OR^k$,
(5) —CN,
(6) —$C_{1-6}$alkyl,
(7) —$C_{3-6}$cycloalkyl,
(8) $C_{3-6}$cycloalkyl-$C_{1-3}$alkyl-,
(9) —$C_{2-6}$cycloheteroalkyl, and
(10) $C_{2-6}$cycloheteroalkyl-$C_{1-3}$ alkyl-,
wherein each alkyl, cycloalkyl and cycloheteroalkyl is unsubstituted or substituted with one to three substituents selected from $R^L$, and wherein one of $R^1$ and $R^2$ is substituted with $R^7$,
or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$;

$R^3$ is absent or selected from the group consisting of:
(1) hydrogen,
(2) halogen,
(3) —$OR^e$,
(4) —CN,
(5) —$C_{1-6}$alkyl,
(6) —$C_{3-6}$cycloalkyl, and
(7) $C_{3-6}$cycloalkyl-$C_{1-3}$alkyl-,
wherein each alkyl and cycloalkyl is unsubstituted or substituted with one to three substituents selected from $R^i$;

$R^4$ is selected from the group consisting of:
(1) hydrogen,
(2) halogen,
(3) $OR^e$,
(4) $C_{0-5}$alkyl$NR^cR^d$,
(5) $C_{1-6}$alkyl,
(6) $C_{1-6}$alkyl-O—,
(7) $C_{3-6}$cycloalkyl,
(8) $C_{3-6}$cycloalkyl-O—,
(9) $C_{3-6}$cycloalkyl-$C_{1-10}$alkyl-,
(10) $C_{3-6}$cycloalkyl-$C_{1-10}$alkyl-O—,
(11) $C_{2-5}$cycloheteroalkyl,
(12) $C_{2-5}$cycloheteroalkyl-O—,
(13) $C_{2-5}$ cycloheteroalkyl-$C_{1-10}$alkyl-,
(14) $C_{2-5}$ cycloheteroalkyl-$C_{1-10}$alkyl-O—,
(15) aryl,
(16) aryl-O—,
(17) aryl-$C_{1-10}$alkyl-,
(18) heteroaryl,
(19) heteroaryl-O—, and
(20) heteroaryl-$C_{1-10}$alkyl-,
wherein each alkyl, cycloalkyl, cycloheteroalkyl, aryl and heteroaryl is unsubstituted or substituted with one to three substituents selected from $R^j$,
provided that when $R^4$ is selected from the group consisting of:
(1) $OR^e$,
(2) $C_0$alkyl-$NR^cR^d$,
(3) $C_{1-6}$alkyl-O—,
(4) $C_{3-6}$cycloalkyl-O—,
(5) $C_{3-6}$cycloalkyl-$C_{1-10}$alkyl-O—,
(6) $C_{2-5}$cycloheteroalkyl-O—,
(7) $C_{2-5}$ cycloheteroalkyl-$C_{1-10}$alkyl-O—, (8) aryl-O—, and
(9) heteroaryl-O—,
then X is selected from the group consisting of:
(1) —$CR^9R^9$,
(2) C=O, and
(3) —$C(R^9)OC_{1-6}$alkyl;
$R^5$ is absent or selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^6$ is absent or selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

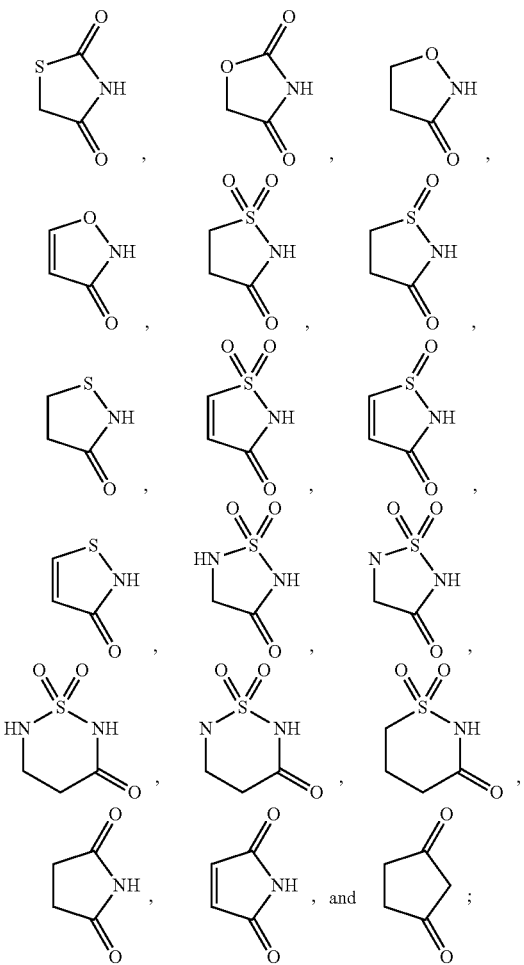

$R^8$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three substituents selected from $R^j$;
$R^9$ is selected from the group consisting of:
(1) hydrogen,
(2) —$C_{1-6}$alkyl,
(3) halogen,
(4) —$(CH_2)_{0-5}$OH,
(5) —$(CH_2)_{0-5}OC_{1-6}$alkyl,
(6) —$(CH_2)_{0-5}NR^cR^d$,
(7) —$C_{3-6}$cycloalkyl, and
(8) aryl-$C_{1-6}$alkyl,
wherein $CH_2$ is unsubstituted or substituted with one or two substituents selected from $R^j$, and wherein alkyl, cycloalkyl and aryl is unsubstituted or substituted with one to three substituents selected from $R^j$;
$R^a$ is selected from the group consisting of:
(1) —$C_{1-6}$alkyl,
(2) halogen,
(3) —$C_{0-6}$alkyl-$OR^e$,
(4) —$C_{0-6}$alkyl-$NR^cS(O)_nR^e$,
(5) —$C_{0-6}$alkyl-$S(O)_nR^e$,
(6) —$C_{0-6}$alkyl-$S(O)_nNR^cR^d$,
(7) —$C_{0-6}$alkyl-$NR^cR^d$,
(8) —$C_{0-6}$alkyl-$C(O)R^e$,
(9) —$C_{0-6}$alkyl-$OC(O)R^e$,
(10) —$C_{0-6}$alkyl-$CO_2R^e$,
(11) —$C_{0-6}$alkyl-CN,
(12) —$C_{0-6}$alkyl-$C(O)NR^cR^d$,
(13) —$C_{0-6}$alkyl-$NR^cC(O)R^e$,
(14) —$C_{0-6}$alkyl-$NR^cC(O)OR^e$,
(15) —$C_{0-6}$alkyl-$NR^cC(O)NR^cR^d$,
(16) —$CF_3$,
(17) —$OCF_3$,
(18) —$OCHF_2$,
(19) —$C_{0-6}$alkyl-aryl,
(20) —$C_{0-6}$alkyl-heteroaryl,
(21) —$C_{0-6}$alkyl-$C_{3-10}$cycloalkyl,
(22) —$C_{0-6}$alkyl-$C_{3-10}$cycloalkenyl, and
(23) —$C_{0-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;
$R^b$ is selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)pOC_{1-10}$alkyl,
(10) —$O(CH_2)pC_{3-6}$cycloalkyl,
(11) —$O(CH_2)pC_{3-6}$ cycloalkyl-$C_{1-10}$alkyl,
(12) —$O(CH_2)pC_{2-5}$cycloheteroalkyl,
(13) —$O(CH_2)pC_{2-5}$cycloheteroalkyl-$C_{1-10}$alkyl,
(14) —O-aryl,
(15) —O-heteroaryl,
(16) —O-aryl-$C_{1-10}$alkyl,
(17) —O-heteroaryl-$C_{1-10}$alkyl,

(18) —O(CH$_2$)pNR$^c$S(O)$_m$R$^e$,
(19) —O(CH$_2$)pS(O)$_m$R$^e$,
(20) —O(CH$_2$)pS(O)$_m$NR$^c$R$^d$,
(21) —O(CH$_2$)pNR$^c$R$^d$,
(22) —C(O)R$^e$,
(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)pO—C$_{3-6}$cycloalkyl,
(30) —O(CH$_2$)pO—C$_{2-5}$ cycloheteroalkyl,
(31) —OCF$_3$,
(32) —OCHF$_2$,
(33) —(CH$_2$)pC$_{3-6}$cycloalkyl,
(34) —(CH$_2$)pC$_{2-5}$ cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH$_2$, alkyl, alkenyl, cycloalkyl, cycloheteroalkyl, aryl and heteroaryl is unsubstituted or substituted with one to five substituents independently selected from: —C$_{1-6}$alkyl, halogen, OH, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$cycloheteroalkyl,
(7) C$_{2-5}$ cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$,
or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) C$_{3-6}$ cycloalkyl-C$_{1-10}$alkyl-,
(6) —C$_{2-5}$cycloheteroalkyl,
(7) C$_{2-5}$ cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents selected from R$^h$;
each R$^f$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein alkyl is unsubstituted or substituted with one to three substituents independently selected from: —OH, halogen, C$_{1-6}$alkyl, cyano and S(O)$_2$C$_{1-6}$alkyl;
each R$^g$ is independently selected from the group consisting of:
(1) hydrogen,
(2) —C(O)R$^e$, and
(3) —C$_{1-10}$alkyl,
wherein alkyl is unsubstituted or substituted with one to five halogens;
each R$^h$ is independently selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein alkyl is unsubstituted or substituted with one to three substituents independently selected from: —OH, halogen, C$_{1-6}$alkyl, cyano and S(O)$_2$C$_{1-6}$alkyl;
each R$^i$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each R$^j$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,

(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

each R$^k$ is independently selected from the group consisting of:
(1) hydrogen,
(2) —C$_{1-6}$ alkyl,
(3) —C$_{1-6}$alkyl-SO$_2$C$_{1-6}$alkyl,
(4) —CF$_3$, and
(5) —CHF$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;

each R$^L$ is independently selected from the group consisting of:
(1) —CO$_2$C$_{1-6}$alkyl,
(2) —C$_{1-10}$alkyl,
(3) —C$_{2-10}$ alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with one to four substituents independently selected from C$_{1-6}$alkyl, halogen, and —OC$_{1-6}$alkyl;

each R$^m$ is independently selected from the group consisting of:
(1) —C$_{1-10}$alkyl,
(2) —C$_{2-10}$ alkenyl,
(3) —C$_{3-6}$ cycloalkyl,
(4) C$_{3-6}$ cycloalkyl-C$_{1-10}$alkyl-,
(5) —C$_{2-5}$cycloheteroalkyl,
(6) C$_{2-5}$ cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;

each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, "a" is a single bond. In another embodiment of the present invention, "a" is a single bond; and R$^5$ and R$^6$ are present.

In another embodiment of the present invention, "a" is a double bond and R$^5$ and R$^6$ are absent. In another embodiment, "a" is a double bond, R$^5$ and R$^6$ are absent and Q is selected from the group consisting of: C—R$^4$, —C—OC$_{1-6}$alkyl, and N.

In another embodiment of the present invention, "a" is a single bond, and Q is selected from the group consisting of: oxygen, sulfur, —CR$^4$R$^6$, S(O)$_2$, C=O, —C(R$^9$)OC$_{1-6}$alkyl, and —NR$^c$. In another embodiment of the present invention, "a" is a single bond, R$^5$ and R$^6$ are present, and Q is selected from the group consisting of: oxygen, sulfur, —CR$^4$R$^6$, S(O)$_2$, C=O, —C(R$^9$)OC$_{1-6}$alkyl, and —NR$^c$.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: CR$^1$, N and N-oxide. In a class of this embodiment, U is selected from the group consisting of: CR$^1$ and N. In another class of this embodiment, U is CR$^1$. In another class of this embodiment, U is N or N-oxide. In another class of this embodiment, U is N. In another class of this embodiment, U is N-oxide.

In another embodiment of the present invention, V is selected from the group consisting of: CR$^2$, N and N-oxide. In a class of this embodiment, V is selected from the group consisting of: CR$^2$ and N. In another class of this embodiment, V is CR$^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then R$^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then R$^3$ is absent, and further provided that both U and V are not N or N-oxide. In another class of this embodiment, W is CH, provided that no more than two of T, U, V and W are selected from N and N-oxide, further provided that if both T and W are N or N-oxide, then R$^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then R$^3$ is absent, and further provided that both U and V are not N or N-oxide. In another class of this embodiment, W is N, provided that no more than two of T, U, V and W are selected from N and N-oxide, further provided that if both T and W are N or N-oxide, then R$^3$ is absent, and further provided that both U and V are not N or N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is CR$^1$, V is CR$^2$, and W is CH. In a class of this embodiment, T is CH, U is CR$^1$, V is CH, and W is CH. In another class of this embodiment, T is CH, U is CH, V is CR$^2$, and W is CH.

In another embodiment of the present invention, T is N or N-oxide, U is CR$^1$, V is CR$^2$, and W is CH. In a class of this embodiment, T is N, U is CR$^1$, V is CR$^2$, and W is CH. In another embodiment of the present invention, T is CH, U is N or N-oxide, and V is CR$^2$, and W is CH. In a class of this embodiment, T is CH, U is N, V is CR$^2$, and W is CH. In another embodiment of the present invention, T is CH, U is $CR^1$, V is N or N-oxide, and W is CH. In a class of this embodiment, T is CH, U is $CR^1$, and V is N or N-oxide, and W is CH. In another embodiment of the present invention, T is CH, U is $CR^1$, V is $CR^2$, and W is CH, N or N-oxide. In another embodiment of the present invention, T is CH, U is $CR^1$, V is $CR^2$, and W is N or N-oxide. In a class of this embodiment, T is CH, U is $CR^1$, V is $CR^2$, and W is N.

In another embodiment of the present invention, T is N or N-oxide, U is N or N-oxide, V is $CR^2$, and W is CH. In a class of this embodiment, T is N, U is N, V is $CR^2$, and W is CH. In another embodiment of the present invention, T is N or N-oxide, U is $CR^1$, V is N or N-oxide, and W is CH. In a class of this embodiment, T is N, U is $CR^1$, V is N, and W is CH. In another embodiment of the present invention, T is N or N-oxide, U is $CR^1$, V is $CR^2$, and W is N or N-oxide. In a class of this embodiment, T is N, U is $CR^1$, V is $CR^2$, and W is N.

In another embodiment of the present invention, T is N or N-oxide, U is $CR^1$, V is $CR^2$, and W is N or N-oxide; and $R^3$ is absent. In a class of this embodiment, T is N, U is $CR^1$, V is $CR^2$, and W is N; and $R^3$ is absent. In another embodiment of the present invention, T is CH, U is N or N-oxide, V is $CR^2$, and W is N or N-oxide. In a class of this embodiment, T is CH, U is N, V is $CR^2$, and W is N. In another embodiment of the present invention, T is CH, U is $CR^1$, V is N or N-oxide, and W is N or N-oxide. In a class of this embodiment, T is CH, U is $CR^1$, V is N, and W is N. In another embodiment of the present invention, T is CH; U is $CR^1$; V is $CR^2$; and W is CH, N or N-oxide.

In another embodiment of the present invention, Q is selected from the group consisting of: oxygen, sulfur, $-CR^4R^6$, C=O, $-C(R^9)OC_{1-6}$alkyl, and $-NR^c$. In another embodiment of the present invention, Q is selected from the group consisting of: oxygen, sulfur, $-CR^4R^6$, $-C(R^9)OC_{1-6}$alkyl, and $-NR^c$. In another embodiment of the present invention, Q is selected from the group consisting of: oxygen, sulfur, $-CR^4R^6$, and $-NR^c$. In another embodiment of the present invention, Q is selected from the group consisting of: oxygen, $-CR^4R^6$, and $-NR^c$. In another embodiment of the present invention, Q is selected from the group consisting of: oxygen, and $-CR^4R^6$. In a class of this embodiment, Q is selected from the group consisting of: oxygen, and $-CH_2$.

In another embodiment of the present invention, Q is oxygen. In another embodiment of the present invention, Q is $-CR^4R^6$. In a class of this embodiment, Q is $-CH_2$. In another class of this embodiment, Q is $-CH$.

In another embodiment of the present invention, X is selected from the group consisting of: oxygen, $-CR^9R^9$, $S(O)_2$, C=O, $-C(R^9)OC_{1-6}$alkyl, and $-NR^c$, provided that if Q is oxygen, sulfur or $-NR^c$, then X is not oxygen or $-NR^c$, further provided that if Q is C=O, then X is not C=O or $S(O)_2$, and further provided that if Q is $S(O)_2$, then X is not $S(O)_2$, C=O, or oxygen. In another embodiment of the present invention, X is selected from the group consisting of: oxygen, $-CR^9R^9$, $S(O)_2$, C=O, and $-NR^c$, provided that if Q is oxygen, sulfur or $-NR^c$, then X is not oxygen or $-NR^c$, further provided that if Q is C=O, then X is not C=O or $S(O)_2$, and further provided that if Q is $S(O)_2$, then X is not $S(O)_2$, C=O, or oxygen.

In another embodiment of the present invention, X is selected from the group consisting of: oxygen, $-CR^9R^9$, C=O, and $-NR^c$, provided that if Q is oxygen, sulfur or $-NR^c$, then X is not oxygen or $-NR^c$, further provided that if Q is C=O, then X is not C=O, and further provided that if Q is $S(O)_2$, then X is not C=O, or oxygen. In another embodiment of the present invention, X is selected from the group consisting of: oxygen, $-CR^9R^9$, and $-NR^c$, provided that if Q is oxygen, sulfur or $-NR^c$, then X is not oxygen or $-NR^c$, and further provided that if Q is $S(O)_2$, then X is not oxygen. In another embodiment of the present invention, X is oxygen. In another embodiment of the present invention, X is $-NR^c$. In another embodiment of the present invention, X is $-CR^9R^9$. In a class of this embodiment, X is $-CH_2$.

In another embodiment of the present invention, X is selected from the group consisting of: $-CR^9$, $-C-OC_{1-6}$alkyl, and $-N$, provided that if Q is oxygen, sulfur or $-NR^c$, then X is not $-N$. In another embodiment of the present invention, X is selected from the group consisting of: $-CR^9$, and $-N$, provided that if Q is oxygen, sulfur or $-NR^c$, then X is not $-N$. In another embodiment of the present invention, X is $-N$. In another embodiment of the present invention, X is $-CR^9$. In a class of this embodiment, X is $-CH-$.

In another embodiment of the present invention, Y is selected from the group consisting of: oxygen, $-CR^9R^9$, $S(O)_2$, C=O, $-C(R^9)OC_{1-6}$alkyl, and $-NR^c$, that if X is oxygen, sulfur or $-NR^c$, then Y is not oxygen or $-NR^c$, further provided that if X is C=O, then Y is not C=O or $S(O)_2$, and further provided that if X is $S(O)_2$, then Y is not $S(O)_2$, C=O, or oxygen. In another embodiment of the present invention, Y is selected from the group consisting of: oxygen, $-CR^9R^9$, $S(O)_2$, C=O, and $-NR^c$, provided that if X is oxygen, sulfur or $-NR^c$, then Y is not oxygen, or $-NR^c$, further provided that if X is C=O, then Y is not C=O or $S(O)_2$, and further provided that if X is $S(O)_2$, then Y is not $S(O)_2$, C=O, or oxygen. In another embodiment of the present invention, Y is selected from the group consisting of: oxygen, $-CR^9R^9$, C=O, and $-NR^c$, provided that if X is oxygen, sulfur or $-NR^c$, then Y is not oxygen, or $-NR^c$, further provided that if X is C=O, then Y is not C=O, and further provided that if X is $S(O)_2$, then Y is not C=O, or oxygen.

In another embodiment of the present invention, Y is selected from the group consisting of: oxygen, $-CR^9R^9$, and $-NR^c$, provided that if X is oxygen, sulfur or $-NR^c$, then Y is not oxygen, or $-NR^c$, and further provided that if X is $S(O)_2$, then Y is not oxygen. In another embodiment of the present invention, Y is oxygen. In another embodiment of the present invention, Y is $-NR^c$. In another embodiment of the present invention, Y is $-CR^9R^9$. In a class of this embodiment, Y is $-CH_2$.

In another embodiment of the present invention, Y is selected from the group consisting of: $-CR^9$, $-C-OC_{1-6}$alkyl, and $-N$, provided that if X is oxygen, sulfur or $-NR^c$, then Y is not $-N$. In another embodiment of the present invention, Y is selected from the group consisting of: $-CR^9$, and $-N$, provided that if X is oxygen, sulfur or $-NR^c$, then Y is not $-N$. In another embodiment of the present invention, Y is $-N$. In another embodiment of the present invention, Y is $-CR^9R^9$. In a class of this embodiment, Y is $-CH_2$.

In another embodiment of the present invention, Z is selected from the group consisting of: oxygen, $-CR^9R^9$, $S(O)_2$, and $-NR^c$. In another embodiment of the present invention, Z is selected from the group consisting of: oxygen, $-CR^9R^9$, and $-NR^c$. In another embodiment of the present invention, Z is selected from the group consisting of: oxygen, and $-CR^9R^9$. In another embodiment of the present invention, Z is selected from the group consisting of: oxygen, and $-NR^c$. In another embodiment of the present invention, Z is $-NR^c$. In another embodiment of the present invention, Z is S(O)$_2$. In another embodiment of the present invention, Z is —CR$^9$R$^9$. In a class of this embodiment, Z is CH$_2$. In another embodiment of the present invention, Z is oxygen.

In another embodiment of the present invention, A is selected from the group consisting of: aryl, heteroaryl, and C$_{2-5}$cycloheteroalkyl, wherein each aryl, heteroaryl and cycloheteroalkyl is unsubstituted or substituted with one to five substituents selected from R$^a$. In a class of this embodiment, A is selected from the group consisting of: phenyl, pyridyl, and azetidine, wherein each phenyl, pyridyl and azetidine is unsubstituted or substituted with one to four substituents selected from R$^a$. In another class of this embodiment, A is selected from the group consisting of: phenyl, pyridyl, azetidine and pyrazinyl, wherein each phenyl, pyridyl, azetidine and pyrazinyl is unsubstituted or substituted with one to four substituents selected from R$^a$. In another embodiment of the present invention, A is selected from the group consisting of: aryl, and heteroaryl, wherein each aryl and heteroaryl is unsubstituted or substituted with one to five substituents selected from R$^a$. In a class of this embodiment, A is selected from the group consisting of: phenyl, pyridyl and pyrazinyl, wherein phenyl, pyridyl and pyrazinyl is unsubstituted or substituted with one to four substituents selected from R$^a$. In another class of this embodiment, A is selected from the group consisting of: phenyl and pyridyl, wherein each phenyl and pyridyl is unsubstituted or substituted with one to four substituents selected from R$^a$. In another embodiment of the present invention, A is selected from the group consisting of: aryl, wherein aryl is unsubstituted or substituted with one to five substituents selected from R$^a$. In a class of this embodiment, A is phenyl, wherein phenyl is unsubstituted or substituted with one to five substituents selected from R$^a$. In another embodiment of the present invention, A is selected from the group consisting of: heteroaryl, wherein heteroaryl is unsubstituted or substituted with one to five substituents selected from R$^a$. In a class of this embodiment, A is selected from the group consisting of: pyridyl and pyrazinyl, wherein each pyridyl and pyrazinyl is unsubstituted or substituted with one to four substituents selected from R$^a$. In another class of this embodiment, A is pyrazinyl, wherein pyrazinyl is unsubstituted or substituted with one to four substituents selected from R$^a$. In another class of this embodiment, A is pyridyl, wherein pyridyl is unsubstituted or substituted with one to four substituents selected from R$^a$. In another embodiment of the present invention, A is selected from the group consisting of: C$_{2-5}$cycloheteroalkyl, wherein each cycloheteroalkyl is unsubstituted or substituted with one to five substituents selected from R$^a$. In a class of this embodiment, A is azetidine, wherein azetidine is unsubstituted or substituted with one to four substituents selected from R$^a$.

In another embodiment of the present invention, B is selected from the group consisting of: aryl, aryl-O—, aryl-C$_{1-10}$ alkyl-, aryl-C$_{1-10}$ alkyl-O—, C$_{3-6}$cycloalkyl, C$_{3-6}$cycloalkyl-C$_{1-10}$alkyl-, C$_{3-6}$cycloalkyl-C$_{1-10}$alkyl-O—, C$_{3-6}$cycloalkenyl, C$_{3-6}$cycloalkenyl-C$_{1-10}$alkyl-, C$_{3-6}$cycloalkenyl-C$_{1-10}$alkyl-O—, C$_{2-5}$cycloheteroalkyl, C$_{3-6}$cycloheteroalkyl-C$_{1-10}$alkyl-, C$_{3-6}$cycloheteroalkyl-C$_{1-10}$alkyl-O—, heteroaryl, heteroaryl-O—, heteroaryl-C$_{1-10}$ alkyl-, and heteroaryl-C$_{1-10}$ alkyl-O—, wherein B is unsubstituted or substituted with one to five substituents selected from R$^b$.

In another embodiment of the present invention, B is selected from the group consisting of: aryl, aryl-C$_{1-10}$ alkyl-, C$_{3-6}$cycloalkyl, C$_{3-6}$cycloalkyl-C$_{1-10}$alkyl-, C$_{3-6}$cycloalkenyl, C$_{3-6}$cycloalkenyl-C$_{1-10}$alkyl-, C$_{2-5}$cycloheteroalkyl, C$_{3-6}$cycloheteroalkyl-C$_{1-10}$alkyl, heteroaryl, and heteroaryl-C$_{1-10}$ alkyl-, wherein B is unsubstituted or substituted with one to five substituents selected from R$^b$. In another embodiment of the present invention, B is selected from the group consisting of: aryl, aryl-C$_{1-10}$ alkyl-, C$_{3-6}$cycloalkyl, C$_{3-6}$cycloalkyl-C$_{1-10}$alkyl-, C$_{2-5}$cycloheteroalkyl, C$_{3-6}$cycloheteroalkyl-C$_{1-10}$alkyl-, heteroaryl, and heteroaryl-C$_{1-10}$ alkyl-, wherein B is unsubstituted or substituted with one to five substituents selected from R$^b$. In another embodiment of the present invention, B is selected from the group consisting of: aryl, aryl-C$_{1-10}$ alkyl-, C$_{3-6}$cycloalkyl, C$_{2-5}$cycloheteroalkyl, heteroaryl, and heteroaryl-C$_{1-10}$ alkyl-, wherein B is unsubstituted or substituted with one to five substituents selected from R$^b$.

In another embodiment of the present invention, B is selected from the group consisting of: aryl, aryl-C$_{1-10}$ alkyl-, and heteroaryl, wherein each alkyl, aryl and heteroaryl is unsubstituted or substituted with one to five substituents selected from R$^b$. In a class of this embodiment, B is selected from the group consisting of: phenyl, —CH$_2$-phenyl, and pyridyl, wherein each phenyl and pyridyl is unsubstituted or substituted with one to five substituents selected from R$^b$.

In another embodiment of the present invention, B is selected from the group consisting of: aryl, wherein each aryl is unsubstituted or substituted with one to five substituents selected from R$^b$. In a class of this embodiment, B is phenyl, wherein each phenyl is unsubstituted or substituted with one to five substituents selected from R$^b$. In another embodiment of the present invention, B is selected from the group consisting of: aryl-C$_{1-10}$ alkyl-, wherein each alkyl and aryl is unsubstituted or substituted with one to five substituents selected from R$^b$. In a class of this embodiment, B is selected from the group consisting of: —CH$_2$-phenyl, wherein each phenyl is unsubstituted or substituted with one to five substituents selected from R$^b$. In another embodiment of the present invention, B is selected from the group consisting of: heteroaryl, wherein each heteroaryl is unsubstituted or substituted with one to five substituents selected from R$^b$. In a class of this embodiment, B is selected from the group consisting of: pyridyl, wherein each pyridyl is unsubstituted or substituted with one to five substituents selected from R$^b$.

In another embodiment of the present invention, R$^1$ and R$^2$ are each independently selected from: hydrogen, halogen, —OR$^k$, —CN, —C$_{1-6}$alkyl, —C$_{3-6}$cycloalkyl, C$_{3-6}$cycloalkyl-C$_{1-3}$alkyl-, —C$_{2-6}$cycloheteroalkyl, and C$_{2-6}$cycloheteroalkyl-C$_{1-3}$alkyl-, wherein each alkyl, cycloalkyl and cycloheteroalkyl is unsubstituted or substituted with one to three substituents selected from R$^L$, and wherein one of R$^1$ and R$^2$ is substituted with R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with R$^7$.

In another embodiment of the present invention, R$^1$ and R$^2$ are each independently selected from: hydrogen, halogen, —OR$^k$, —CN, —C$_{1-6}$alkyl, —C$_{3-6}$cycloalkyl, C$_{3-6}$cycloalkyl-C$_{1-3}$alkyl-, —C$_{2-6}$cycloheteroalkyl, and C$_{2-6}$cycloheteroalkyl-C$_{1-3}$alkyl-, wherein each alkyl, cycloalkyl and cycloheteroalkyl is unsubstituted or substituted with one to three substituents selected from R$^L$, and wherein one of R$^1$ and R$^2$ is substituted with R$^7$. In another embodiment of the present invention, R$^1$ and R$^2$ are each independently selected from: hydrogen, halogen, —OR$^k$, —CN, and —C$_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen, halogen, —$OR^k$, —CN, and —$C_{1-6}$alkyl, wherein each alkyl is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen, and —$C_{1-6}$alkyl, wherein each alkyl is unsubstituted or substituted with one to three substituents selected from $R^L$, and wherein one of $R^1$ and $R^2$ is substituted with $R^7$. In another embodiment of the present invention, $R^1$ and $R^2$ are each independently selected from: hydrogen, and ethyl, wherein ethyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen, and ethyl, wherein ethyl is unsubstituted or substituted with one to three substituents selected from $R^L$, and wherein one of $R^1$ and $R^2$ is substituted with $R^7$. In another class of this embodiment, $R^1$ is selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ is selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ is —CH(cyclopropyl)-CH($CH_3$)—$CO_2H$. In another embodiment of the present invention, $R^1$ is —CH(cyclopropyl)-CH($CH_3$)—$CO_2H$, and $R^2$ is hydrogen. In another embodiment of the present invention, $R^2$ is —CH(cyclopropyl)-CH($CH_3$)—$CO_2H$. In another embodiment of the present invention, $R^2$ is —CH(cyclopropyl)-CH($CH_3$)—$CO_2H$, and $R^1$ is hydrogen.

In another embodiment of the present invention, $R^1$ is —$(CH_2)_2$—$CO_2H$. In another embodiment of the present invention, $R^1$ is —$(CH_2)_2$—$CO_2H$, and $R^2$ is hydrogen. In another embodiment of the present invention, $R^2$ is —$(CH_2)_2$—$CO_2H$. In another embodiment of the present invention, $R^2$ is —$(CH_2)_2$—$CO_2H$, and $R^1$ is hydrogen.

In another embodiment of the present invention, $R^1$ is selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$. In another embodiment of the present invention, $R^1$ is selected from: hydrogen, halogen, —$OR^k$, and —CN.

In another embodiment of the present invention, $R^1$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$. In another embodiment of the present invention, $R^1$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$; and $R^2$ is hydrogen.

In another embodiment of the present invention, $R^1$ is selected from: hydrogen, halogen, —$OR^k$, —CN, and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another embodiment of the present invention, $R^1$ is selected from: hydrogen, halogen, —$OR^k$, —CN, and —$C_{1-6}$alkyl, wherein each alkyl is unsubstituted or substituted with one to three substituents selected from $R^L$, and wherein one of $R^1$ and $R^2$ is substituted with $R^7$.

In another embodiment of the present invention, $R^1$ is selected from: hydrogen, and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another embodiment of the present invention, $R^1$ is selected from: hydrogen, and —$C_{1-6}$alkyl, wherein each alkyl is unsubstituted or substituted with one to three substituents selected from $R^L$, and wherein one of $R^1$ and $R^2$ is substituted with $R^7$. In another embodiment of the present invention, $R^1$ is selected from: hydrogen and ethyl, wherein ethyl is unsubstituted or substituted with one to three substituents selected from $R^L$, and wherein one of $R^1$ and $R^2$ is substituted with $R^7$. In another embodiment of the present invention, $R^1$ is hydrogen. In another embodiment of the present invention, $R^1$ is selected from: —$C_{1-6}$alkyl, wherein alkyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another embodiment of the present invention, $R^1$ is ethyl, wherein ethyl is unsubstituted or substituted with one to three substituents selected from $R^L$, and wherein $R^1$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with $R^7$. In another embodiment of the present invention, $R^1$ is ethyl, wherein ethyl is unsubstituted or substituted with one to three substituents selected from $R^L$, and wherein $R^1$ is substituted with $R^7$.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with $R^7$; and $R^2$ is hydrogen. In another embodiment of the present invention, $R^1$ is ethyl, wherein ethyl is unsubstituted or substituted with one to three substituents selected from $R^L$, and wherein $R^1$ is substituted with $R^7$; and $R^2$ is hydrogen.

In another embodiment of the present invention, $R^1$ is hydrogen. In another embodiment, $R^1$ is independently selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$; and $R^2$ is hydrogen.

In another embodiment, $R^2$ is selected from: a bond, hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^2$ is selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^1$ and $R^2$ are each independently selected from: hydrogen, and —$C_{1-6}$alkyl, wherein one of $R^1$ and $R^2$ is —$C_{1-6}$alkyl substituted with $R^7$, and wherein alkyl is unsubstituted or substituted with one to three substituents independently selected from $R^L$; or a pharmaceutically acceptable salt thereof. In another embodiment of the present invention, $R^1$ and $R^2$ are each independently selected from: hydrogen, and ethyl, wherein one of $R^1$ and $R^2$ is ethyl substituted with $R^7$, and wherein ethyl is unsubstituted or substituted with one to three substituents independently selected from $R^L$; or a pharmaceutically acceptable salt thereof.

In another embodiment of the present invention, $R^2$ is selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein one of $R^1$ and $R^2$ is substituted with $R^7$. In another embodiment of the present invention, $R^2$ is selected from: hydrogen, halogen, —$OR^k$, and —CN.

In another embodiment of the present invention, $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$. In another embodiment of the present invention, $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$; and $R^1$ is hydrogen.

In another embodiment of the present invention, $R^2$ is selected from: hydrogen, halogen, —$OR^k$, —CN, and —$C_{1-6}$alkyl, wherein each alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$. In another embodiment of the present invention, $R^2$ is selected from: hydrogen, halogen, —$OR^k$, —CN, and —$C_{1-6}$alkyl, wherein each alkyl is unsubstituted or substituted with one to three substituents selected from $R^L$, and wherein one of $R^1$ and $R^2$ is substituted with $R^7$.

In another embodiment of the present invention, $R^2$ is selected from: hydrogen, and —$C_{1-6}$alkyl, wherein alkyl is unsubstituted or substituted with one to three substituents selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^2$ is selected from: hydrogen, and —$C_{1-6}$alkyl, wherein alkyl is unsubstituted or substituted with one to three substituents selected from $R^L$, and wherein one of $R^1$ and $R^2$ is substituted with $R^7$. In another embodiment of the present invention, $R^2$ is selected from: hydrogen and ethyl, wherein ethyl is unsubstituted or substituted with one to three substituents selected from $R^L$, and wherein one of $R^1$ and $R^2$ is substituted with $R^7$. In another embodiment of the present invention, $R^2$ is hydrogen. In another embodiment of the present invention, $R^2$ is ethyl, wherein ethyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^2$ is selected from: ethyl, wherein ethyl is unsubstituted or substituted with one to three substituents selected from $R^L$, and wherein $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with $R^7$.

In another embodiment of the present invention, $R^2$ is —$C_{1-6}$alkyl, wherein alkyl is unsubstituted or substituted with one to three substituents selected from $R^L$, and wherein $R^2$ is substituted with $R^7$. In another embodiment of the present invention, $R^2$ is ethyl, wherein ethyl is unsubstituted or substituted with one to three substituents selected from $R^L$, and wherein $R^2$ is substituted with $R^7$.

In another embodiment of the present invention, $R^2$ is —$C_{1-6}$alkyl, wherein alkyl is unsubstituted or substituted with one to three substituents selected from $R^L$, and wherein $R^2$ is substituted with $R^7$; and $R^1$ is hydrogen. In another embodiment of the present invention, $R^2$ is ethyl, wherein ethyl is unsubstituted or substituted with one to three substituents selected from $R^L$, and wherein $R^2$ is substituted with $R^7$; and $R^1$ is hydrogen.

In another embodiment, $R^2$ is independently selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$; and $R^1$ is hydrogen.

In one class of the embodiments of the present invention, at least one of $R^1$ and $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-. wherein each alkyl, cycloalkyl and cycloheteroalkyl is unsubstituted or substituted with one to three substituents independently selected from $R^L$, and wherein one alkyl, cycloalkyl or cycloheteroalkyl is substituted with $R^7$. In another class of the embodiments of the present invention, one of $R^1$ and $R^2$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein one alkyl, cycloalkyl or cycloheteroalkyl is substituted with $R^7$. In another class of the embodiments of the present invention, at least one of $R^1$ and $R^2$ is —$C_{1-6}$alkyl, wherein alkyl is unsubstituted or substituted with one to three substituents independently selected from $R^L$, and wherein one alkyl is substituted with $R^7$. In another class of the embodiments of the present invention, one of $R^1$ and $R^2$ is —$C_{1-6}$alkyl, wherein alkyl is unsubstituted or substituted with one to three substituents independently selected from $R^L$, and wherein alkyl is substituted with $R^7$. In another class of the embodiments of the present invention, one of $R^1$ and $R^2$ is —$C_{1-6}$alkyl, wherein alkyl is substituted with one or two substituents independently selected from $R^L$, and wherein alkyl is substituted with $R^7$. In another class of the embodiments of the present invention, at least one of $R^1$ and $R^2$ is ethyl, wherein ethyl is unsubstituted or substituted with one to three substituents independently selected from $R^L$, and wherein one ethyl is substituted with $R^7$. In another class of the embodiments of the present invention, one of $R^1$ and $R^2$ is ethyl, wherein ethyl is unsubstituted or substituted with one to three substituents independently selected from $R^L$, and wherein ethyl is substituted with $R^7$. In another class of the embodiments of the present invention, one of $R^1$ and $R^2$ is ethyl, wherein ethyl is substituted with one or two substituents independently selected from $R^L$, and wherein ethyl is substituted with $R^7$.

In another embodiment, $R^3$ is absent or when present is selected from the group consisting of: hydrogen, halogen, —$OR^e$, —CN, —$C_{1-6}$alkyl, —$C_{3-6}$cycloalkyl, and $C_{3-6}$cycloalkyl-$C_{1-3}$alkyl-, wherein each alkyl and cycloalkyl is unsubstituted or substituted with one to three substituents selected from $R^i$. In another embodiment of the present invention, $R^3$ is absent or selected from the group consisting of: hydrogen, halogen, and —$C_{1-6}$alkyl, wherein each alkyl is unsubstituted or substituted with one to three substituents selected from $R^1$. In another embodiment of the present invention, $R^3$ is absent or selected from the group consisting of: hydrogen, and halogen, wherein each alkyl is unsubstituted or substituted with one to three substituents selected from $R^1$. In another embodiment of the present invention, $R^3$ is absent. In another embodiment of the present invention, $R^3$ is absent or hydrogen. In another embodiment of the present invention, $R^3$ is hydrogen. In another embodiment of the present invention, $R^3$ is absent or halogen. In another embodiment of the present invention, $R^3$ is halogen.

In another embodiment of the present invention, $R^3$ is absent or —$C_{1-6}$alkyl, wherein alkyl is unsubstituted or substituted with one to three substituents selected from $R^1$. In another embodiment of the present invention, $R^3$ is —$C_{1-6}$alkyl, wherein alkyl is unsubstituted or substituted with one to three substituents selected from $R^1$.

In another embodiment of the present invention, $R^4$ is selected from the group consisting of: hydrogen, halogen, $OR^e$, $C_{0-5}$alkylNR$^c$R$^d$, $C_{1-6}$alkyl, and $C_{1-6}$alkyl-O—, wherein alkyl is unsubstituted or substituted with one to three substituents selected from $R^j$, provided that when $R^4$ is selected from the group consisting of: $OR^e$, $C_0$alkyl-NR$^c$R$^d$, and $C_{1-6}$alkyl-O—, then X is selected from the group consisting of: —$CR^9R^9$, C=O, and —$C(R^9)OC_{1-6}$alkyl. In another embodiment of the present invention, $R^4$ is selected from the group consisting of: hydrogen, halogen, —$C_{0-5}$alkylNR$^c$R$^d$, and —$C_{1-6}$alkyl, wherein alkyl is unsubstituted or substituted with one to three substituents selected from $R^j$, provided that when $R^4$ is selected from the group consisting of: —$C_0$alkyl-NR$^c$R$^d$, then X is selected from the group consisting of: —$CR^9R^9$, C=O, and —$C(R^9)OC_{1-6}$alkyl.

In another embodiment of the present invention, $R^4$ is selected from the group consisting of: hydrogen, halogen, and $C_{1-6}$alkyl, wherein alkyl is unsubstituted or substituted with one to three substituents selected from $R^j$. In another embodiment of the present invention, $R^4$ is selected from the group consisting of: hydrogen, and $C_{1-6}$alkyl, wherein alkyl is unsubstituted or substituted with one to three substituents selected from $R^j$. In another embodiment of the present invention, $R^4$ is hydrogen. In another embodiment of the present invention, $R^4$ is —$C_{1-6}$alkyl, wherein alkyl is unsubstituted or substituted with one to three substituents selected from $R^j$.

In another embodiment of the present invention, $R^5$ is absent or when present $R^5$ is selected from the group consisting of: hydrogen, —$C_{1-6}$alkyl, and —$C_{3-6}$cycloalkyl, wherein each alkyl and cycloalkyl is unsubstituted or substituted with one to three substituents selected from $R^1$. In another embodiment of the present invention, $R^5$ is absent or selected from the group consisting of: hydrogen, and —$C_{1-6}$alkyl, wherein alkyl is unsubstituted or substituted with one to three substituents selected from $R^j$. In another embodiment of the present invention, $R^5$ is absent. In another embodiment of the present invention, $R^5$ is absent or hydrogen. In another embodiment of the present invention, $R^5$ is hydrogen. In another embodiment of the present invention, $R^5$ is absent or —$C_{1-6}$alkyl, wherein alkyl is unsubstituted or substituted with one to three substituents selected from $R^j$. In another embodiment of the present invention, $R^5$ is selected from the group consisting of: —$C_{1-6}$alkyl, wherein alkyl is unsubstituted or substituted with one to three substituents selected from $R^j$. In another embodiment of the present invention, $R^5$ is —$C_{1-6}$alkyl.

In another embodiment of the present invention, $R^6$ is absent, or when present $R^6$ is selected from the group consisting of: hydrogen, —$C_{1-6}$alkyl, and —$C_{3-6}$cycloalkyl, wherein each alkyl and cycloalkyl is unsubstituted or substituted with one to three substituents selected from $R^j$. In another embodiment of the present invention, $R^6$ is absent or selected from the group consisting of: hydrogen, and —$C_{1-6}$alkyl, wherein alkyl is unsubstituted or substituted with one to three substituents selected from $R^j$. In another embodiment of the present invention, $R^6$ is absent. In another embodiment of the present invention, $R^6$ is absent or hydrogen. In another embodiment of the present invention, $R^6$ is hydrogen. In another embodiment of the present invention, $R^6$ is absent or —$C_{1-6}$alkyl, wherein alkyl is unsubstituted or substituted with one to three substituents selected from $R^j$. In another embodiment of the present invention, $R^6$ is —$C_{1-6}$alkyl, wherein alkyl is unsubstituted or substituted with one to three substituents selected from $R^j$. In another embodiment of the present invention, $R^6$ is —$C_{1-6}$alkyl.

In another embodiment of the present invention, $R^7$ is —$CO_2R^8$. In a class of this embodiment, $R^7$ is —$CO_2H$.

In another embodiment of the present invention, $R^8$ is selected from the group consisting of: hydrogen, —$C_{1-6}$alkyl, and —$C_{3-6}$cycloalkyl, wherein each alkyl, and cycloalkyl is unsubstituted or substituted with one to three substituents selected from $R^j$. In another embodiment of the present invention, $R^8$ is selected from the group consisting of: hydrogen, and —$C_{1-6}$alkyl, wherein alkyl is unsubstituted or substituted with one to three substituents selected from $R^j$. In another embodiment of the present invention, $R^8$ is hydrogen. In another embodiment of the present invention, $R^8$ is —$C_{1-6}$alkyl, wherein alkyl is unsubstituted or substituted with one to three substituents selected from $R^j$. In another embodiment of the present invention, $R^8$ is —$C_{1-6}$alkyl.

In another embodiment of the present invention, $R^9$ is selected from the group consisting of: hydrogen, —$C_{1-6}$alkyl, halogen, —$(CH_2)_{0-5}$OH, —$(CH_2)_{0-5}$OC$_{1-6}$alkyl, and —$(CH_2)_{0-6}$NR$^c$R$^d$, wherein each $CH_2$ is unsubstituted or substituted with one or two substituents selected from $R^j$, and alkyl is unsubstituted or substituted with one to three substituents selected from $R^j$. In another embodiment of the present invention, $R^9$ is selected from the group consisting of: hydrogen, —$C_{1-6}$alkyl, halogen, and —$(CH_2)_{0-6}$NR$^c$R$^d$, wherein each $CH_2$ is unsubstituted or substituted with one or two substituents selected from $R^j$, and alkyl is unsubstituted or substituted with one to three substituents selected from $R^j$. In another embodiment of the present invention, $R^9$ is selected from the group consisting of: hydrogen, —$C_{1-6}$alkyl, and halogen, wherein alkyl is unsubstituted or substituted with one to three substituents selected from $R^j$. In another embodiment of the present invention, $R^9$ is selected from the group consisting of: hydrogen, and halogen. In another embodiment of the present invention, $R^9$ is selected from the group consisting of: hydrogen, and F. In another embodiment of the present invention, $R^9$ is hydrogen. In another embodiment of the present invention, $R^9$ is —$C_{1-6}$alkyl, wherein alkyl is unsubstituted or substituted with one to three substituents selected from $R^j$. In another embodiment of the present invention, $R^9$ is halogen.

In another embodiment of the present invention, $R^a$ is selected from the group consisting of: —$C_{1-6}$alkyl, halogen, —$C_{0-6}$alkyl-OR$^e$, —$C_{0-6}$alkyl-NR$^c$S(O)$_n$R$^e$, —$C_{0-6}$alkyl-S(O)$_n$R$^e$, —$C_{0-6}$alkyl-S(O)$_n$NR$^c$R$^d$, —$C_{0-6}$alkyl-NR$^c$R$^d$, —$C_{0-6}$alkyl-C(O)$R^e$, —$C_{0-6}$alkyl-OC(O)$R^e$, —$C_{0-6}$alkyl-CO$_2R^e$, —$C_{0-6}$alkyl-CN, —$C_{0-6}$alkyl-C(O)NR$^cR^d$, —$C_{0-6}$alkyl-NR$^c$C(O)$R^e$, —$C_{0-6}$alkyl-NR$^c$C(O)O$R^e$, —$C_{0-6}$alkyl-NR$^c$C(O)NR$^cR^d$, —CF$_3$, —OCF$_3$, —OCHF$_2$, aryl, heteroaryl, —$C_{3-10}$cycloalkyl, —$C_{3-10}$cycloalkenyl, and —$C_{2-10}$cycloheteroalkyl, wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —S(O)$_2$—$C_{1-4}$alkyl, —CN, —OCHF$_2$, —OCF$_3$, —CF$_3$, and —$C_{0-6}$alkyl-NR$^cR^d$;

In another embodiment of the present invention, $R^a$ is selected from the group consisting of: —$C_{1-6}$alkyl, halogen, —$C_{0-6}$alkyl-O$R^e$, —$C_{0-6}$alkyl-NR$^c$S(O)$_nR^e$, —$C_{0-6}$alkyl-S(O)$_nR^e$, —$C_{0-6}$alkyl-S(O)$_n$NR$^cR^d$, —$C_{0-6}$alkyl-NR$^cR^d$, —$C_{0-6}$alkyl-C(O)$R^e$, —$C_{0-6}$alkyl-OC(O)$R^e$, —$C_{0-6}$alkyl-CO$_2R^e$, —$C_{0-6}$alkyl-CN, —$C_{0-6}$alkyl-C(O)NR$^cR^d$, —$C_{0-6}$alkyl-NR$^c$C(O)$R^e$, —$C_{0-6}$alkyl-NR$^c$C(O)O$R^e$, —$C_{0-6}$alkyl-NR$^c$C(O)NR$^cR^d$, —CF$_3$, —OCF$_3$, and —OCHF$_2$, wherein each alkyl is unsubstituted or substituted with one to five substituents independently selected from: —$C_{1-6}$alkyl, halogen, OH, —O—$C_{1-6}$alkyl, —S(O)$_2$—$C_{1-4}$alkyl, —CN, —OCHF$_2$, —OCF$_3$, —CF$_3$, and —$C_{0-6}$alkyl-NR$^cR^d$. In another embodiment of the present invention, $R^a$ is selected from the group consisting of: —$C_{1-6}$alkyl, halogen, —O$R^e$, —$C_{0-6}$alkyl-NR$^cR^d$, —C(O)$R^e$, —OC(O)$R^e$, —CO$_2R^e$, —CN, —CF$_3$, —OCF$_3$, and —OCHF$_2$, wherein each alkyl is unsubstituted or substituted with one to five substituents independently selected from: —$C_{1-6}$alkyl, halogen, OH, —O—$C_{1-6}$alkyl, —S(O)$_2$—$C_{1-4}$alkyl, —CN, —OCHF$_2$, —OCF$_3$, —CF$_3$, and —$C_{0-6}$alkyl-NR$^cR^d$.

In another embodiment of the present invention, $R^a$ is selected from the group consisting of: —$C_{1-6}$alkyl, halogen, —O$R^e$, —$C_{0-5}$alkyl-NR$^cR^d$, —CN, —CF$_3$, —OCF$_3$, and —OCHF$_2$, wherein alkyl is unsubstituted or substituted with one to five substituents independently selected from: —$C_{1-6}$alkyl, halogen, OH, —O—$C_{1-6}$alkyl and —CF$_3$. In another embodiment of the present invention, $R^a$ is selected from the group consisting of: —$C_{1-6}$alkyl, and halogen, wherein alkyl is unsubstituted or substituted with one to five substituents independently selected from: —$C_{1-6}$alkyl, halogen, OH, —O—$C_{1-6}$alkyl and —CF$_3$. In another embodiment of the present invention, $R^a$ is —$C_{1-6}$alkyl, wherein alkyl is unsubstituted or substituted with one to five substituents independently selected from: —$C_{1-6}$alkyl, halogen, OH, —O—$C_{1-6}$alkyl and —CF$_3$. In another embodiment of the present invention, $R^a$ is halogen. In a class of this embodiment, $R^a$ is F.

In another embodiment of the present invention, $R^b$ is selected from the group consisting of: —$C_{1-10}$alkyl, —$C_{2-10}$alkenyl, —CF$_3$, halogen, —CN, —OH, —OC$_{1-10}$alkyl, —OC$_{2-10}$alkenyl, —O(CH$_2$)pOC$_{1-10}$alkyl, —O(CH$_2$)pNR$^c$S(O)$_mR^e$, —O(CH$_2$)pS(O)$_mR^e$, —O(CH$_2$)pS(O)$_m$NR$^cR^d$, —O(CH$_2$)pNR$^cR^d$, —C(O)$R^e$, —OC(O)$R^e$, —CO$_2R^e$, —C(O)NR$^cR^d$, —NR$^c$C(O)$R^e$, —NR$^c$C(O)O$R^e$, —NR$^c$C(O)NR$^cR^d$, —OCF$_3$, and —OCHF$_2$, wherein each CH, CH$_2$, alkyl, and alkenyl is unsubstituted or substituted with one to five substituents independently selected from: —$C_{1-6}$alkyl, halogen, OH, —O—$C_{1-6}$alkyl and —CF$_3$. In another embodiment of the present invention, $R^b$ is selected from the group consisting of: —$C_{1-10}$alkyl, —CF$_3$, halogen, —CN, —OH, —OC$_{1-10}$alkyl, —O(CH$_2$)pOC$_{1-10}$alkyl, —O(CH$_2$)pNR$^cR^d$, —C(O)$R^e$, —OC(O)$R^e$, —CO$_2R^e$, —OCF$_3$, and —OCHF$_2$, wherein each CH, CH$_2$, alkyl, and alkenyl is unsubstituted or substituted with one to five substituents independently selected from: —$C_{1-6}$alkyl, halogen, OH, —O—$C_{1-6}$alkyl and —CF$_3$.

In another embodiment of the present invention, $R^b$ is selected from the group consisting of: —$C_{1-10}$alkyl, —CF$_3$, halogen, —CN, —OH, —OC$_{1-10}$alkyl, —OCF$_3$, and —OCHF$_2$, wherein each CH, and alkyl is unsubstituted or substituted with one to five substituents independently selected from: —$C_{1-6}$alkyl, halogen, OH, —O—$C_{1-6}$alkyl and —CF$_3$. In another embodiment of the present invention, $R^b$ is selected from the group consisting of: —$C_{1-10}$alkyl, —CF$_3$, halogen, and —OC$_{1-10}$alkyl, wherein each alkyl is unsubstituted or substituted with one to five substituents independently selected from: —$C_{1-6}$alkyl, halogen, OH, —O—$C_{1-6}$alkyl and —CF$_3$. In a class of this embodiment, $R^b$ is selected from the group consisting of: —CH$_3$, —CF$_3$, F, and —OCH$_3$. In another class of this embodiment, $R^b$ is selected from the group consisting of: F and —OCH$_3$.

In another embodiment of the present invention, $R^c$ and $R^d$ are each independently selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$. In another embodiment of the present invention, $R^c$ and $R^d$ are each independently selected from the group consisting of: hydrogen, $C_{1-10}$alkyl, and $C_{2-10}$alkenyl, wherein each alkyl, and alkenyl is unsubstituted or substituted with one to three substituents independently selected from $R^f$. In another embodiment of the present invention, $R^c$ and $R^d$ are each independently selected from the group consisting of: hydrogen, and $C_{1-10}$alkyl, wherein alkyl is unsubstituted or substituted with one to three substituents independently selected from $R^f$. In another embodiment of the present invention, $R^c$ and $R^d$ are each hydrogen. In another embodiment of the present invention, $R^c$ and $R^d$ are each independently selected from the group consisting of: $C_{1-10}$alkyl, wherein alkyl is unsubstituted or substituted with one to three substituents independently selected from $R^f$. In another embodiment of the present invention, $R^c$ and $R^d$ are each independently selected from the group consisting of: $C_{1-10}$alkyl.

In another embodiment of the present invention, $R^c$ is selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$. In another embodiment of the present invention, $R^c$ is selected from the group consisting of: hydrogen, $C_{1-10}$alkyl, and $C_{2-10}$alkenyl, wherein each alkyl, and alkenyl is unsubstituted or substituted with one to three substituents independently selected from $R^f$. In another embodiment of the present invention, $R^c$ is selected from the group consisting of: hydrogen, and $C_{1-10}$alkyl, wherein alkyl is unsubstituted or substituted with one to three substituents independently selected from $R^f$. In another embodiment of the present invention, $R^c$ is hydrogen. In another embodiment of the present invention, $R^c$ is —$C_{1-10}$alkyl, wherein alkyl is unsubstituted or substituted with one to three substituents independently selected from $R^f$. In another embodiment of the present invention, $R^c$ is —$C_{1-10}$alkyl.

In another embodiment of the present invention, $R^d$ is selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$. In another embodiment of the present invention, $R^d$ is selected from the group consisting of: hydrogen, $C_{1-10}$alkyl, and $C_{2-10}$alkenyl, wherein each alkyl and alkenyl is unsubstituted or substituted with one to three substituents independently selected from $R^f$. In another embodiment of the present invention, $R^d$ is selected from the group consisting of: hydrogen, and $C_{1-10}$alkyl, wherein alkyl is unsubstituted or substituted with one to three substituents independently selected from $R^f$. In another embodiment of the present invention, $R^d$ is hydrogen. In another embodiment of the present invention, $R^d$ is —$C_{1-10}$alkyl, wherein alkyl is unsubstituted or substituted with one to three substituents independently selected from $R^f$. In another embodiment of the present invention, $R^d$ is —$C_{1-10}$alkyl.

In another embodiment of the present invention, $R^e$ is independently selected from the group consisting of: hydrogen, —$C_{1-10}$alkyl, and —$C_{2-10}$ alkenyl, wherein each alkyl, and alkenyl is unsubstituted or substituted with one to three substituents selected from $R^h$. In another embodiment of the present invention, each $R^e$ is independently selected from the group consisting of: hydrogen, and —$C_{1-10}$alkyl, wherein alkyl is unsubstituted or substituted with one to three substituents selected from $R^h$. In another embodiment of the present invention, $R^e$ is hydrogen. In another embodiment of the present invention, each $R^e$ is —$C_{1-10}$alkyl, wherein alkyl is unsubstituted or substituted with one to three substituents selected from $R^h$. In another embodiment of the present invention, each $R^e$ is —$C_{1-10}$alkyl.

In another embodiment of the present invention, each $R^f$ is selected from the group consisting of: halogen, —$C_{1-10}$alkyl, —OH, —O—$C_{1-4}$alkyl, —CN, —$CF_3$, —$OCHF_2$, and —$OCF_3$, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is selected from the group consisting of: halogen, —$C_{1-10}$alkyl, —CN, and —$CF_3$, wherein alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen, and $C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is selected from the group consisting of: halogen. In another embodiment of the present invention, each $R^f$ is —$C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is —$C_{1-10}$alkyl.

In another embodiment of the present invention, each $R^g$ is independently selected from the group consisting of: hydrogen, and —$C_{1-10}$alkyl, wherein alkyl is unsubstituted or substituted with one to five halogens. In another embodiment of the present invention, $R^g$ is hydrogen. In another embodiment of the present invention, each $R^g$ is —$C_{1-10}$alkyl, wherein alkyl is unsubstituted or substituted with one to five halogens. In another embodiment of the present invention, each $R^g$ is —$C_{1-10}$alkyl.

In another embodiment of the present invention, each $R^h$ is independently selected from the group consisting of: halogen, —$C_{1-10}$alkyl, —OH, —O—$C_{1-4}$alkyl, —CN, —$CF_3$, —$OCHF_2$, and —$OCF_3$, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is independently selected from the group consisting of: halogen, —$C_{1-10}$alkyl, —CN, and —$CF_3$, wherein alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^h$ is independently selected from the group consisting of: halogen, and $C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is independently selected from the group consisting of: halogen. In another embodiment of the present invention, each $R^h$ is —$C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is —$C_{1-10}$alkyl.

In another embodiment of the present invention, each $R^i$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, and —$OCHF_2$. In another embodiment of the present invention, each $R^i$ is independently selected from the group consisting of: —$C_{1-6}$alkyl, —$OR^e$, halogen, —$S(O)_mR^e$, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, each $R^i$ is independently selected from the group consisting of: —$C_{1-6}$alkyl, —$OR^e$, halogen, —$NR^cR^d$, —CN, —$CF_3$, —$OCF_3$, and —$OCHF_2$. In another embodiment of the present invention, each $R^i$ is independently selected from the group consisting of: —$C_{1-6}$alkyl, and halogen. In another embodiment of the present invention, each $R^i$ is independently selected from the group consisting of: halogen. In another embodiment of the present invention, each $R^i$ is independently selected from the group consisting of: —$C_{1-6}$alkyl.

In another embodiment of the present invention, each $R^j$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, and —$OCHF_2$. In another embodiment of the present invention, each $R^j$ is independently selected from the group consisting of: —$C_{1-6}$alkyl, —$OR^e$, halogen, —$S(O)_mR^e$, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, each $R^j$ is independently selected from the group consisting of: —$C_{1-6}$alkyl, —$OR^e$, halogen, —$NR^cR^d$, —CN, —$CF_3$, —$OCF_3$, and —$OCHF_2$. In another embodiment of the present invention, each $R^j$ is independently selected from the group consisting of: —$C_{1-6}$alkyl, and halogen. In another embodiment of the present invention, each $R^j$ is halogen. In another embodiment of the present invention, each $R^j$ is —$C_{1-6}$alkyl.

In another embodiment of the present invention, each $R^k$ is independently selected from the group consisting of:

hydrogen, —$C_{1-6}$alkyl, —$CF_3$, and —$CHF_2$, wherein alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, each $R^k$ is independently selected from the group consisting of: hydrogen, and —$C_{1-6}$alkyl, wherein alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, $R^k$ is hydrogen. In another embodiment of the present invention, each $R^k$ is —$C_{1-6}$alkyl, wherein alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, each $R^k$ is —$C_{1-6}$alkyl.

In another embodiment of the present invention, each $R^L$ is independently selected from the group consisting of: —$CO_2C_{1-6}$alkyl, —$C_{1-10}$alkyl, —$C_{2-10}$alkenyl, —$C_{2-10}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to four substituents independently selected from —$C_{1-6}$alkyl, halogen, and —$OC_{1-6}$alkyl. In another embodiment of the present invention, each $R^L$ is independently selected from the group consisting of: —$CO_2C_{1-6}$alkyl, —$C_{1-10}$alkyl, —$C_{3-6}$cycloalkyl, and —$C_{2-6}$cycloheteroalkyl, wherein each alkyl, cycloalkyl, and cycloheteroalkyl is unsubstituted or substituted with one to four substituents independently selected from $C_{1-6}$alkyl, halogen, and —$OC_{1-6}$alkyl. In another embodiment of the present invention, each $R^L$ is independently selected from the group consisting of: —$C_{1-10}$alkyl, —$C_{3-6}$cycloalkyl, and —$C_{2-6}$cycloheteroalkyl, wherein each alkyl, cycloalkyl, and cycloheteroalkyl is unsubstituted or substituted with one to four substituents independently selected from $C_{1-6}$alkyl, halogen, and —$OC_{1-6}$alkyl.

In another embodiment of the present invention, each $R^L$ is independently selected from the group consisting of: —$C_{1-10}$alkyl, and —$C_{3-6}$cycloalkyl, wherein each alkyl, and cycloalkyl is unsubstituted or substituted with one to four substituents independently selected from —$C_{1-6}$alkyl, halogen, and —$OC_{1-6}$alkyl. In another embodiment of the present invention, each $R^L$ is independently selected from the group consisting of: —$CH_3$, cyclobutyl and -cyclopropyl. In another embodiment of the present invention, each $R^L$ is independently selected from the group consisting of: —$CH_3$, and -cyclopropyl. In another embodiment of the present invention, each $R^L$ is —$C_{1-10}$alkyl, wherein alkyl is unsubstituted or substituted with one to four substituents independently selected from $C_{1-6}$alkyl, halogen, and —$OC_{1-6}$alkyl. In another embodiment of the present invention, each $R^L$ is —$CH_3$. In another embodiment of the present invention, each $R^L$ is independently selected from the group consisting of: —$C_{3-6}$cycloalkyl, wherein cycloalkyl is unsubstituted or substituted with one to four substituents independently selected from $C_{1-6}$alkyl, halogen, and —$OC_{1-6}$alkyl. In another embodiment of the present invention, each $R^L$ is independently selected from the group consisting of: cyclobutyl and -cyclopropyl. In another embodiment of the present invention, each $R^L$ is -cyclopropyl. In another embodiment of the present invention, each $R^L$ is cyclobutyl.

In another embodiment of the present invention, each $R^m$ is independently selected from the group consisting of: —$C_{1-10}$alkyl, and —$C_{2-10}$ alkenyl. In another embodiment of the present invention, each $R^m$ is —$C_{1-10}$alkyl.

In another embodiment of the present invention, n is 0, 1 or 2. In a class of this embodiment, n is 0 or 1. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In another embodiment of the present invention, p is 0, 1, 2, 3 or 4. In a class of this embodiment, p is 0, 1, 2 or 3. In a class of this embodiment, p is 0, 1 or 2. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, each r is independently selected from: 0, 1, 2 or 3. In a class of this embodiment, r is 0, 1 or 2. In another class of this embodiment, r is 1, 2 or 3. In a class of this embodiment, r is 1 or 2. In another class of this embodiment, r is 0 or 1. In another class of this embodiment, r is 0 or 2. In another class of this embodiment, r is 0 or 1. In another class of this embodiment, r is 1 or 3. In another class of this embodiment, r is 2 or 3. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, the invention relates to compounds of structural formula Ia:

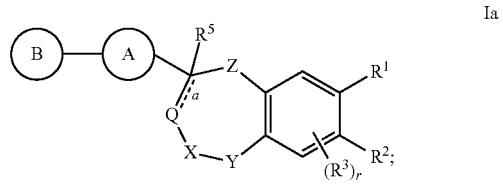

or a pharmaceutically acceptable salt thereof.

In another embodiment of the present invention, the invention relates to compounds of structural formula Ib:

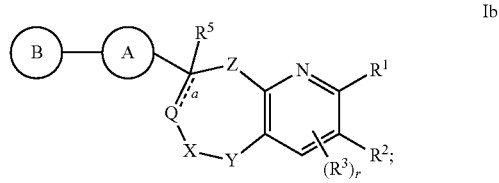

or a pharmaceutically acceptable salt thereof.

In another embodiment of the present invention, the invention relates to compounds of structural formula Ic:

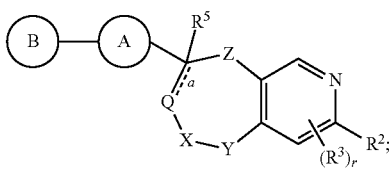

or a pharmaceutically acceptable salt thereof.

In another embodiment of the present invention, the invention relates to compounds of structural formula Id:

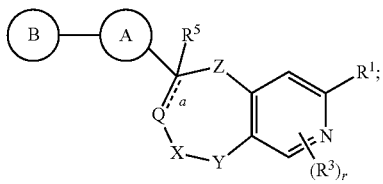

or a pharmaceutically acceptable salt thereof.

In another embodiment of the present invention, the invention relates to compounds of structural formula Ie:

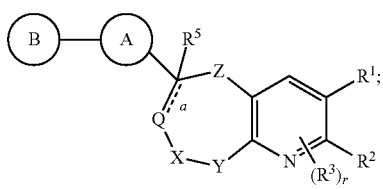

or a pharmaceutically acceptable salt thereof.

In another embodiment of the present invention, the invention relates to compounds of structural formula If:

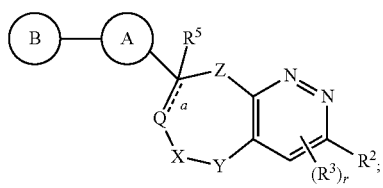

or a pharmaceutically acceptable salt thereof.

In another embodiment of the present invention, the invention relates to compounds of structural formula Ig:

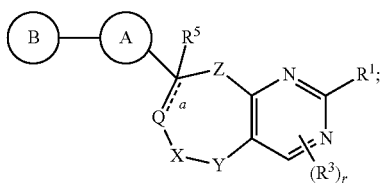

or a pharmaceutically acceptable salt thereof.

In another embodiment of the present invention, the invention relates to compounds of structural formula Ih:

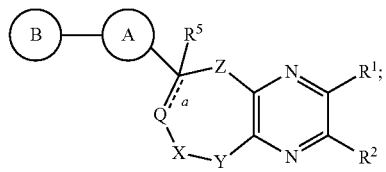

or a pharmaceutically acceptable salt thereof.

In another embodiment of the present invention, the invention relates to compounds of structural formula Ii:

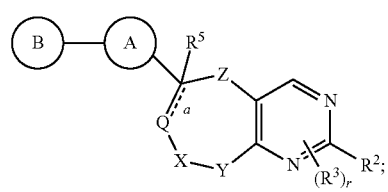

or a pharmaceutically acceptable salt thereof.

In another embodiment of the present invention, the invention relates to compounds of structural formula Ij:

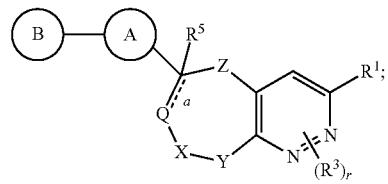

or a pharmaceutically acceptable salt thereof.

In another embodiment of the present invention, the invention relates to compounds of structural formula Ik:

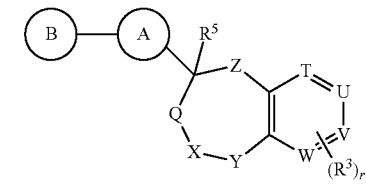

or a pharmaceutically acceptable salt thereof.

In another embodiment of the present invention, the invention relates to compounds of structural formula Il:

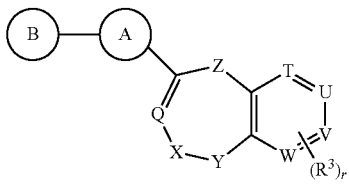

or a pharmaceutically acceptable salt thereof.

In another embodiment of the present invention, the invention relates to compounds of structural formula Im:

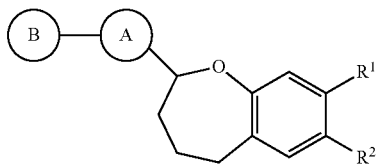

or a pharmaceutically acceptable salt thereof.

The compound of structural formula I includes the compounds of structural formulas Ia, Ib, Ic, Id, Ie, If, Ig, Ih, Ii, Ij, Ik, Il and Im, and pharmaceutically acceptable salts, hydrates and solvates thereof.

Another embodiment of the present invention relates to compounds of structural formula Ia:

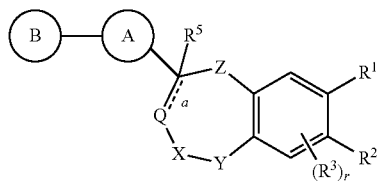

wherein
"a" is a single bond;
Q is —$CR^4R^6$;
X is —$CR^9R^9$;
Y is —$CR^9R^9$;
Z is oxygen;
A is selected from the group consisting of:
  (1) aryl,
  (2) heteroaryl, and
  (3) $C_{2-5}$ cycloheteroalkyl,
wherein each aryl, heteroaryl and cycloheteroalkyl is unsubstituted or substituted with one to five substituents selected from $R^a$;
B is selected from the group consisting of:
  (1) aryl,
  (2) aryl-$C_{1-10}$ alkyl-, and
  (3) heteroaryl,
wherein each alkyl, aryl and heteroaryl is unsubstituted or substituted with one to five substituents selected from $R^b$;
$R^1$ and $R^2$ are each independently selected from:
  (1) hydrogen, and
  (2) —$C_{1-6}$alkyl,
wherein one of $R^1$ and $R^2$ is —$C_{1-6}$alkyl substituted with $R^7$, and wherein alkyl is unsubstituted or substituted with one to three substituents independently selected from $R^L$;
$R^3$ is absent or hydrogen;
$R^4$ is hydrogen;
$R^5$ is absent or hydrogen;
$R^6$ is absent or hydrogen;
$R^7$ is —$CO_2R^8$;
$R^8$ is hydrogen;
$R^9$ is hydrogen;
each $R^L$ is independently selected from the group consisting of: —$C_{1-10}$alkyl, and —$C_{3-6}$cycloalkyl,
wherein each alkyl, and cycloalkyl is unsubstituted or substituted with one to four substituents independently selected from $C_{1-6}$alkyl, halogen, and —$OC_{1-6}$alkyl; and
each r is independently selected from: 0, 1, 2 or 3;
or a pharmaceutically acceptable salt thereof.

Another embodiment of the present invention relates to compounds of structural Formula Ia:

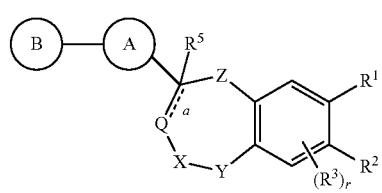

wherein
"a" is a single bond;
Q is —$CR^4R^6$;
X is —$CR^9R^9$;
Y is —$CR^9R^9$;
Z is oxygen;
A is selected from the group consisting of:
  (1) phenyl,
  (2) pyridyl, and
  (3) azetidine,
wherein each phenyl, pyridyl and azetidine is unsubstituted or substituted with one to four substituents selected from $R^a$;
B is selected from the group consisting of:
  (1) phenyl,
  (2) —$CH_2$-phenyl, and
  (3) pyridyl,
wherein each phenyl and pyridyl is unsubstituted or substituted with one to five substituents selected from $R^b$;
$R^1$ and $R^2$ are each independently selected from:
  (1) hydrogen, and
  (2) ethyl,
wherein one of $R^1$ and $R^2$ is ethyl substituted with $R^7$, and wherein ethyl is unsubstituted or substituted with one to three substituents independently selected from $R^L$;
$R^3$ is absent or hydrogen;
$R^4$ is hydrogen;
$R^5$ is hydrogen;
$R^6$ is hydrogen;
$R^7$ is —$CO_2R^8$;
$R^8$ is hydrogen;
$R^9$ is hydrogen;
each $R^L$ is independently selected from the group consisting of: —$CH_3$, and -cyclopropyl; and
each r is independently selected from: 0, 1, 2 or 3;
or a pharmaceutically acceptable salt thereof.

Illustrative, but non-limiting, examples of the compounds of the present invention that are useful as agonists of G-protein-coupled receptor 40 (GPR40) are the following compounds:

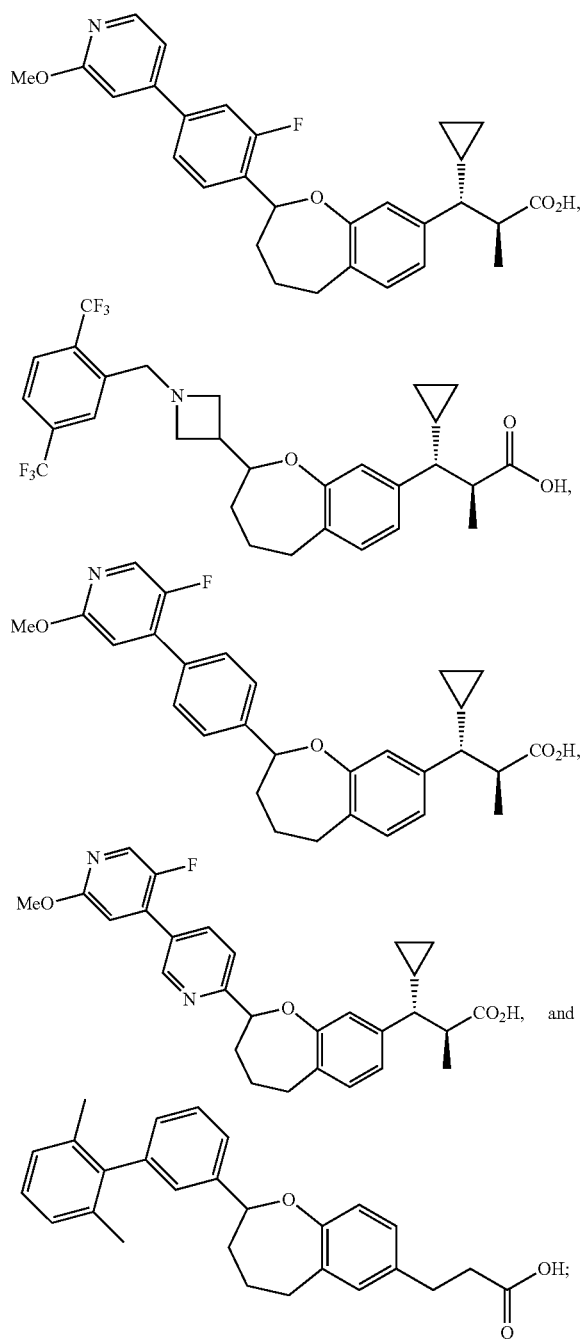

and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. The term —$C_2$alkyl is ethyl. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl. In another embodiment of the present invention, alkyl is ethyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is cyclopropane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is azetidine.

"Cycloheteroalkenyl" means a nonaromatic monocyclic, bicyclic or bridged carbocyclic ring or ring system containing at least one double bond and containing at least one heteroatom selected from N, NH, S (including SO and $SO_2$) and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

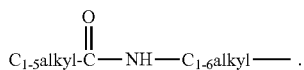

For example, $-NR^cC(O)R^e$ is equivalent to $-N(R^c)C(O)R^e$.

Unless expressly depicted or described otherwise, substituents depicted in a structural formula with a "floating" bond, such as but not limited to $R^3$, is permitted on any available carbon atom in the ring to which the substituent is attached. In one embodiment of the present invention, $R^3$ may be substituted on any CH in the ring to which $R^3$ is attached.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of a GPR40 agonist in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or other mammal in need of treatment.

The term "patient" should be understood to mean a human or other mammal in need of treatment.

The administration of the compound of structural formula I in order to practice the present methods of therapy is carried out by administering a therapeutically effective amount of the compound of structural formula I to the mammal (human or other mammal) in need of such treatment or prophylaxis. The need for a prophylactic administration according to the methods of the present invention is determined via the use of well known risk factors. The therapeutically effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with a therapeutically effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which may be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may preferably be provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention may be indicated, generally satisfactory results could be obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

The compounds of this invention may be used in pharmaceutical compositions comprising (a) the compound(s) or a pharmaceutically acceptable salt thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention may be useful in methods for the prevention or treatment of the aforementioned diseases, disorders and conditions in combination with other therapeutic agents.

The compounds of the present invention may be useful in combination with one or more other drugs in the treatment, prevention, suppression or amelioration of diseases or conditions for which compounds of formula I or the other drugs may have utility, where the combination of the drugs together are safer, more effective or more therapeutically effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to: (1) dipeptidyl peptidase-IV (DPP-4) inhibitors (e.g., sitagliptin, omarigliptin, trelagliptin, teneligliptin, biseagliptin, anagliptin, vildagliptin, saxagliptin, alogliptin, melogliptin, linagliptin, gosogliptin, evogliptin, and gemigliptin), (2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine, insulin lispro and inhalable formulations of each); (4) leptin and leptin derivatives and agonists; (5) amylin and amylin analogs (e.g., pramlintide); (6) sulfonylurea and non-sulfonylurea insulin secretagogues (e.g., tolbutamide, glyburide, glipizide, glimepiride, mitiglinide, meglitinides, nateglinide and repaglinide); (7) α-glucosidase inhibitors (e.g., acarbose, voglibose and miglitol); (8) glucagon receptor antagonists (e.g., MK-3577, MK-0893, LY-2409021 and KT6-971); (9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); (10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe); (11) HDL-raising drugs, (e.g., niacin and nicotinic acid receptor agonists, and extended-release versions thereof; (12) anti-obesity compounds; (13) agents intended for use in inflammatory conditions, such as aspirin, non-steroidal anti-inflammatory drugs or NSAIDs, glucocorticoids, and selective cyclooxygenase-2 or COX-2 inhibitors; (14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan, medoxomil, valsartan, telmisartan, and eprosartan), renin inhibitors (e.g., aliskiren), beta blockers, and calcium channel blockers; (15) glucokinase activators (GKAs) (e.g., AZD6370); (16) inhibitors of 11β-hydroxysteroid dehydrogenase type 1, (e.g., such as those disclosed in U.S. Pat. No. 6,730,690, and LY-2523199); (17) CETP inhibitors (e.g., anacetrapib, evacetrapib, torcetrapib, and AT-03); (18) inhibitors of fructose 1,6-bisphosphatase, (e.g., MB-07803, and such as those disclosed in U.S. Pat. Nos. 6,054,587; 6,110,903; 6,284,748; 6,399,782; and 6,489,476); (19) inhibitors of acetyl CoA carboxylase-1 or 2 (ACC1 or ACC2); (20) AMP-activated Protein Kinase (AMPK) activators (e.g., MB-11055); (21) other agonists of the G-protein-coupled receptors: (i) GPR-109, (ii) GPR-119 (e.g., MBX2982 and PSN821), (iii) GPR-40 (e.g., fasiglifam, JTT-851, TAK-875, and P-11187, and (iv) GPR-120 (e.g., KDT-501); (22) SSTR3 antagonists (e.g., pasireotide, and such as those disclosed in WO 2009/011836); (23) neuromedin U receptor agonists (e.g., such as those disclosed in WO 2009/042053, including, but not limited to, neuromedin S (NMS)); (24) SCD inhibitors; (25) GPR-105 antagonists (e.g., such as those disclosed in WO 2009/000087); (26) SGLT inhibitors (e.g., LIK-066, ASP1941, SGLT-3, ertugliflozin, empagliflozin, dapagliflozin, canagliflozin, BI-10773, PF-04971729, remogliflozin, luseogliflozin, tofogliflozin, ipragliflozin, and LX-4211); (27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (28) inhibitors of fatty acid synthase; (29) inhibitors of acyl coenzyme A:monoacylglycerol acyltransferase 1 and 2 (MGAT-1 and MGAT-2); (30) agonists of the TGR5 receptor (also known as GPBAR1, BG37, GPCR19, GPR131, and M-BAR) (eg., sodium taurocholate); (31) ileal bile acid transporter inhibitors (eg., elobixibat); (32) PACAP, PACAP mimetics, and PACAP receptor 3 agonists; (33) PPAR agonists; (34) protein tyrosine phosphatase-1B (PTP-1B) inhibitors; (35) IL-1b antibodies and inhibitors, (e.g., gevokizumab, canakinumab, danazol, AC-201, and BLX-1002); and (36) bromocriptine mesylate and rapid-release formulations thereof.

Of particular interest are dipeptidyl peptidase-IV (DPP-4) inhibitors that may be useful in combination with compounds of the present invention. Such inhibitors include, without limitation, sitagliptin (disclosed in U.S. Pat. No. 6,699,871), omarigliptin, trelagliptin, teneligliptin, biseligliptin, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, or a sulfonylurea.

Other GPR-40 agonists that may be useful in combination with compounds of the formulas described herein include, but are not limited to: (1) 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide; (2) 5-(4-((3-(2,6-dimethyl-4-(3-(methylsulfonyl)propoxy)phenyl)phenyl)-methoxy)-phenyl)isothiazole-3-ol 1-oxide; and (3) 5-(4-((3-(2-methyl-6-(3-hydroxypropoxy)-pyridine-3-yl)-2-methylphenyl)methoxy)-phenyl)isothiazole-3-ol 1-oxide; and (4) 5-[4-[[3-[4-(3-aminopropoxy)-2,6-dimethylphenyl]phenyl]-methoxy]phenyl]isothiazole-3-ol 1-oxide, and pharmaceutically acceptable salts thereof.

Antiobesity compounds that may be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); $\beta_3$ adrenergic receptor agonists; CB-1 receptor inverse agonists and antagonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that may be useful in combination with a compound of the present invention, see S. Chaki et al., "Recent advances in feeding suppressing agents: potential therapeutic strategy for the treatment of obesity," Expert Opin. Ther. Patents, 11: 1677-1692 (2001); D. Spanswick and K. Lee, "Emerging antiobesity drugs," Expert Opin. Emerging Drugs, 8: 217-237 (2003); J. A. Fernandez-Lopez, et al., "Pharmacological Approaches for the Treatment of Obesity," Drugs, 62: 915-944 (2002); and K. M. Gadde, et al., "Combination pharmaceutical therapies for obesity," Exp. Opin. Pharmacother., 10: 921-925 (2009).

Glucagon receptor antagonists that may be useful in combination with the compounds of formula I include, but are not limited to: (1) N-[4-((1S)-1-{3-(3,5-dichlorophenyl)-5-[6-(trifluoromethoxy)-2-naphthyl]-1H-pyrazol-1-yl}ethyl)benzoyl]-β-alanine; (2) N-[4-((1R)-1-{3-(3,5-dichlorophenyl)-5-[6-(trifluoromethoxy)-2-naphthyl]-1H-pyrazol-1-yl}ethyl)benzoyl]-β-alanine; (3) N-(4-{1-[3-(2,5-dichlorophenyl)-5-(6-methoxy-2-naphthyl)-1H-pyrazol-1-yl]ethyl}benzoyl)-β-alanine; (4) N-(4-{(1S)-1-[3-(3,5-dichlorophenyl)-5-(6-methoxy-2-naphthyl)-1H-pyrazol-1-yl]ethyl}benzoyl)-β-alanine; (5) N-(4-{(1S)-1-[(R)-(4-chlorophenyl)(7-fluoro-5-methyl-1H-indol-3-yl)methyl]butyl}benzoyl)-β-alanine; and (6) N-(4-{(1S)-1-[(4-chlorophenyl)(6-chloro-8-methylquinolin-4-yl)methyl]butyl}benzoyl)-β-alanine; and pharmaceutically acceptable salts thereof.

Another embodiment of the present invention relates to a pharmaceutical composition comprising one or more of the following agents: (a) a compound of structural formula I; (b) one or more compounds selected from the group consisting of: (1) dipeptidyl peptidase-IV (DPP-4) inhibitors (e.g., sitagliptin, omarigliptin, trelagliptin, teneligliptin, biseligliptin, anagliptin, vildagliptin, saxagliptin, alogliptin, melogliptin, linagliptin, gosogliptin, evogliptin, and gemigliptin); (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814; (3) sulfonylurea and non-sulfonylurea insulin secretagogues, (e.g., tolbutamide, glyburide, glipizide, glimepiride, mitiglinide, and meglitinides, such as nateglinide and repaglinide); (4) α-glucosidase inhibitors (e.g., acarbose, voglibose and miglitol); (5) glucagon receptor antagonists; (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe); (7) HDL-raising drugs, such as niacin or a salt thereof and extended-release versions thereof; and nicotinic acid receptor agonists; (8) antiobesity compounds; (9) agents intended for use in inflammatory conditions, such as aspirin, non-steroidal anti-inflammatory drugs (NSAIDs), glucocorticoids, and selective cyclooxygenase-2 (COX-2) inhibitors; (10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers); (11) glucokinase activators (GKAs) (e.g., AZD6370, GKM-001, TMG-123, HMS-5552, DS-7309, PF-04937319, TTP-399, ZYGK-1); (12) inhibitors of 11β-hydroxysteroid dehydrogenase type 1 (e.g., such as those disclosed in U.S. Pat. No. 6,730,690; WO 03/104207; and WO 04/058741); (13) inhibitors of cholesteryl ester transfer protein (CETP), (e.g., torcetrapib, evacetrapib, anacetrapib, and AT-03); (14) inhibitors of fructose 1,6-bisphosphatase (e.g., MB-07803, and such as those disclosed in U.S. Pat. Nos. 6,054,587; 6,110,903; 6,284,748; 6,399,782; and 6,489,476); (15) inhibitors of acetyl CoA carboxylase-1 or 2 (ACC1 or ACC2); (16) AMP-activated Protein Kinase (AMPK) activators (e.g., MB-11055); (17) agonists of the G-protein-coupled receptors: (i) GPR-109, (ii) GPR-119 (e.g., MBX2982, and PSN821), (iii) GPR-40 (e.g., fasiglifam, JTT-851, P-11187, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)phenyl)-isothiazole-3-ol 1-oxide, 5-(4-((3-(2- methyl-6-(3-hydroxypropoxy)pyridine-3-yl)-2-methyl-phenyl)methoxy)phenyl)-isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and (iv) GPR-120 (e.g., KDT-501); (18) SSTR3 antagonists (e.g., pasireotide, and such as those disclosed in WO 2009/011836); (19) neuromedin U receptor agonists (e.g., such as those disclosed in WO2009/042053, including, but not limited to, neuromedin S (NMS)); (20) inhibitors of stearoyl-coenzyme A delta-9 desaturase (SCD); (21) GPR-105 antagonists (e.g., such as those disclosed in WO 2009/000087); (22) inhibitors of glucose uptake, such as sodium-glucose transporter (SGLT) inhibitors and its various isoforms, such as SGLT-1; SGLT-2 (e.g., LIK-066, ertuglifozin, ASP1941, luseogliflozin, BI10773, tofogliflozin, LX4211, canagliflozin, dapagliflozin and remogliflozin; and SGLT-3); (23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (24) inhibitors of fatty acid synthase; (25) inhibitors of acyl coenzyme A:monoacylglycerol acyltransferase 1 and 2 (MGAT-1 and MGAT-2); (26) agonists of the TGR5 receptor (also known as GPBAR1, BG37, GPCR19, GPR131, and M-BAR) (eg., sodium taurocholate); (28) bromocriptine mesylate and rapid-release formulations thereof, and (29) IL-1b antibodies and inhibitors (e.g., gevokizumab, canakinumab, danazol, AC-201, and BLX-1002); and (c) a pharmaceutically acceptable carrier.

Specific compounds that may be useful in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, olmesartan, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention may also provide a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

For the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an effective amount of a compound of the present invention and an amount of another pharmaceutical agent effective to threat that disorder, such that together they give effective relief.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" or "a therapeutically effective dose" means the amount the compound of structural formula I that will elicit the biological or medical response of a tissue, system, animal, mammal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes, but is not limited to, humans, and companion animals such as dogs and cats.

The weight ratio of the compound of the Formula I to the second active ingredient may be varied and will depend upon the effective dose of each ingredient. Generally, a therapeutically effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). All temperatures are degrees Celsius unless otherwise noted.

LIST OF ABBREVIATIONS

Ac is acetyl; AcCN is acetonitrile; AcO is acetoxy; Alk is alkyl; anh. is anhydrous; APCI is atmospheric pressure chemical ionization; aq or aq. is aqueous; Ar is aryl; atm is atmosphere; Boc is tert-butoxycarbonyl; Bn—O is phenyl-CH$_2$—O or benzyloxy; BrettPhos palladacycle precatalyst is Brettphos Pd G1 precatalyst (Aldrich); n-BuLi is n-butyl lithium; Bu$_3$P is tributylphosphine; t-buxhos palladacycle is chloro(2-di-t-butylphosphino-2',4',6'-tri-i-propyl-1,1'-biphenyl)[2-(2-aminoethyl)phenyl]palladium(II), min. 98% [t-BuXPhos Palladacycle]; t-BuOK is potassium tert-butoxide; ° C. is degrees celsius; Cataxium precatalyst or Cataxium Pd precat or precatalyst is cataCXium A Pd G3 (Aldrich); Cbz is benzyloxycarbonyl; conc or conc. is concentrated; CDI is carbonyldiimidazole; CV is column volumes; diatomite is diatomaceous earth or Celite™; DAST is (diethylamino)sulfur trifluoride; DIBAL-H is diisobutylaluminum hydride; DIAD is diisopropyl azodicarboxylate; DCM is dichloromethane; DEA is diethyl amine; DIPEA is N,N-diisopropylethylamine; DIPA is diisopropyl amine; DMAP is 4-dimethyl-aminopyridine; DMF is N,N-dimethylformamide; DMS is dimethyl sulfide; DMSO is dimethylsulfoxide; dppf is 1,1'-Bis(diphenyl-phosphino)ferrocene; eq or equiv is equivalent(s); ESI is electrospray ionization; EA or EtOAc is ethyl acetate; Et is ethyl; Et$_2$O is diethyl ether; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA or i-PrOH is isopropanol; KOAc is potassium acetate; KOtBu is potassium tert-butoxide; L is liter; LAH is lithium aluminum hydride; M is molar; LC-MS is liquid chromatography-mass spectroscopy; LDA is lithium diisopropyl amide; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeOH is methyl alcohol or methanol; MPLC is medium pressure liquid chromatography; MPa is megapascals; MS is mass spectroscopy; MsCl or Ms-Cl is methane sulfonyl chloride; MeCN is acetonitrile; MeI is methyl iodide; MsCl is methane sulfonyl chloride; MTBE is methyl tert-butyl ether; MW is molecular weight; NaOMe is sodium methoxide; NaHMDS is sodium hexamethyl disilazide; NH$_4$OAc is ammonium acetate; NBS is N-bromo succinamide; NEt$_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; PE is petroleum ether; PG is protecting group; Pd$_2$(dba)$_3$ is tris(dibenzylidene-acetone)-dipalladium(0); Pd(OAc)$_2$ is palladium acetate; Pd[P(t-Bu)$_3$]$_2$ is bis(tri-tert-butylphosphine)-palladium (0); Pd(dppf)Cl$_2$ is [1,1'-bis(diphenyl-phosphino)-ferrocene]dichloro-palladium (II); PdCl$_2$ (dppf)$_2$CH$_2$Cl$_2$ is [1,1'-Bis(diphenyl-phosphino)-ferrocene]dichloropalladium(II), complex with dichloromethane (Aldrich); Pd(PPh$_3$)$_4$ is tetrakis or tetrakis(triphenylphosphine)palladium (0); PPh$_3$ is triphenyl phosphine; Pd(t-Bu$_2$P)$_2$—FerrCl$_2$ is bis-tri-tert-butyl-phosphino ferrocene dichloro palladium (II); Pd(OH)$_2$/C is 20% palladium hydroxide on activated carbon (50 wt. % water) or Pearlman's catalyst; precat is precatalyst; prep is preparative; prep. TLC or prep-TLC, or prep TCL is preparative thin layer chromatography; rt or r.t. or RT is room temperature; RuCl[(R,R)-TSDPEN](mesitylene) is [N-[(1R,2R)-2-(Amino-κN)-1,2-diphenylethyl]-4-methylbenzene-sulfonamidato-κN]chloro-[(1,2,3,4,5,6-η)-1,3,5-trimethyl-benzene]-ruthenium; Ru-Josiphos is generated using (Me-allyl)2Ru(COD) (Aldrich) and Josiphos SL-J502-2 (Aldrich); R$_f$ is retention factor; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro(2-dicyclohexylphosphino-2',6'-dimethoxy-1,1'-biphenyl)[2-(2-aminoethylphenyl))]-palladium(II) [CAS-No. 1028206-58-7]; S-Phos precatalyst is S-Phos Pd G2 precatalyst—Aldrich; S-Phos second generation precatalyst is Chloro(2-dicyclohexyl-phosphino-2',6'-dimethoxy-1,1'-biphenyl)[2-(2'-amino-1,1'-biphenyl)]-palladium-(II), SPhos-Pd-G2) [CAS-No. 1375325-64-6]; TBAF is tetrabutylammonium fluoride; TBSCl is tert-butyl dimethylsilyl chloride; TEA is triethyl amine; Tf is trifluoromethane sulfonyl; THF is tetrahydrofuran; Ti(OiPr)$_4$ is titanium isopropoxide; TFA is trifluoroacetic acid; TLC is thin-layer chromatography; TosCl and TsCl is p-toluene sulfonyl chloride; pTSA, pTsOH and TsOH is p-toluenesulfonic acid, Ts$_2$O is tosic anhydride or p-toluene sulfonic anhydride; xphos is 2-dicyclohexylphosphino-2',4',6'-triisopropyl-biphenyl; and vol is volume(s).

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided to illustrate the invention and are not to be construed as limiting the invention in any manner. The scope of the invention is defined by the appended claims.

SCHEME 1

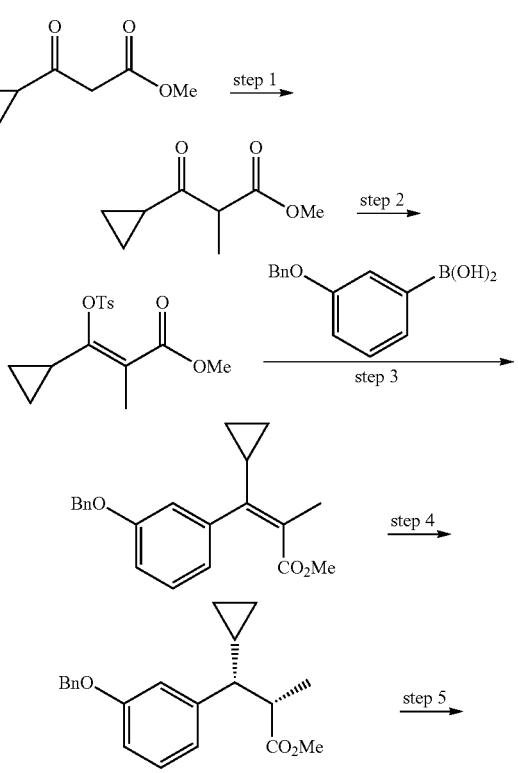

-continued

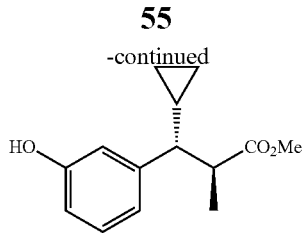

Step 1: MeI, K$_2$CO$_3$, THF;
Step 2: NaHMDS, Ts$_2$O, MTBE;
Step 3: Cataxium-Pd precat, K$_3$PO$_3$, MeCN;
Step 4: Ru-Josiphos,BF$_4$H—Et$_2$O, H$_2$ gas, MeOH;
Step 5: Pd/Pt/C, H$_2$ gas, MeOH Scheme 1 provides a route to Intermediate 1. The cyclopropyl β-ketoester was methylated and then trapped at the vinyl tosylate. Suzuki cross-coupling with m-benzyloxy phenylboronic acid delivered the "Z" enoate. Asymmetric reduction of the double bond was followed by debenzylation under hydrogen pressure.

Intermediate 1

(2R,3R)-Methyl 3-cyclopropyl-3-(3-hydroxyphenyl)-2-methylpropanoate

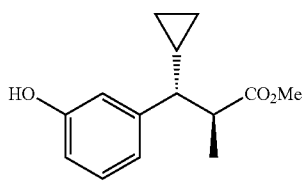 [SMILES: COC(=O)[C@@H](C)[C@H](c1cccc(O)c1)C1CC1]

Step 1: methyl 3-cyclopropyl-2-methyl-3-oxopropanoate

A slurry of NaH (0.563 g, 60% in mineral oil) in THF (20 mL) was cooled to 10° C., and methyl 3-cyclopropyl-3-oxopropanoate (2 g) was added in portions at room temperature over 30 min. Then MeI (0.88 mL) was added over 5 min at room temperature and the reaction was stirred at room temperature overnight. The reaction was then reverse quenched into a half saturated sodium bicarbonate solution (100 mL) and EtOAc (100 mL). The aqueous layer was separated and extracted once with 50 mL EtOAc. The organic layer was washed with water and brine, and then concentrated to give the title compound, which was used in the next the step without further purification.

Step 2: (Z)-methyl 3-cyclopropyl-2-methyl-3-(tosyloxy)acrylate

To a solution of methyl 3-cyclopropyl-2-methyl-3-oxopropanoate (5 g) in MTBE (50 mL) was added a 1M solution of NaHMDS in hexane (41 mL), while keeping the internal temperature between 18-23° C. The reaction was stirred at room temperature for 30 min. Then tosic anhydride (10 g) was slurried in MTBE (200 mL). The reaction mixture was added to the tosic anhydride slurry, while keeping the internal temperature between 19° C. and 24° C. After 30 min, additional tosic anhydride (3.3 g, 0.3 eq) was added, and the reaction was stirred for 1 h. Then water (500 mL) and EtOAc (400 mL) were added to the reaction mixture. The aqueous layer was separated and extracted once with EtOAc (100 mL) The organic layer was separated, washed with water (200 mL) and brine (100 mL), and concentrated to give the crude product, which was re-crystallized from MTBE/heptanes (1:1, 50 mL) to give the title compound.

Step 3: (Z)-methyl 3-(3-(benzyloxy)phenyl)-3-cyclopropyl-2-methylacrylate (Z)-methyl 3-cyclopropyl-2-methyl-3-(tosyloxy)acrylate (1.03 g) was dissolved in MeCN (10 mL), then aqueous potassium phosphate (1 M, 10 mL) was added, followed by the addition of (3-(benzyloxy)phenyl)boronic acid (1 g). The resulting slurry was degassed with a nitrogen stream for 30 min, then cataCXium A Pd G3 (Aldrich #761435, 100 mg) was added and the reaction was heated to 35° C. for 14 h. The resulting slurry was filtered through Celite™, and the Celite™ was washed with EtOAc (20 mL). Then EtOAc (40 mL) and water (50 mL) were added to the filtrate. The aqueous layer was separated, and extracted once with EtOAc (20 mL). The combined organic layer was washed with water (50 mL) and brine (20 mL), and concentrated to give a crude oil, which was purified via ISCO silica column (40 g, diluted with 0-30% Hexanes/EtOAc) to give the title product.

Step 4: (2S,3R)-methyl 3-(3-(benzyloxy)phenyl)-3-cyclopropyl-2-methylpropanoate

Bis(2-methylallyl)(1,5-cyclooctadiene)ruthenium(II) (1.0 g) and (S)-1-[(R)-2-(Di-tert-butylphosphino) ferrocenyl]ethyldiphenylphosphine (Josiphos SL-J502-2, CAS#223121-01-5, 1.86 g) were added to DCM (12 mL) and agitated for 20 min at rt. Then tetrafluoroboric acid-diethyl ether complex (1.0 g) was added slowly and stirred for 20 min at rt. The reaction mixture was diluted with DCM (100 mL) and added to a catalyst bomb with a MeOH rinse. Then (Z)-methyl 3-(3-(benzyloxy)phenyl)-3-cyclopropyl-2-methylacrylate (2.57 g, 7.97 mmol) was added to the catalyst bomb with MeOH (200 mL) and agitated to dissolve. The catalyst bomb was pressurized to 500 psi with hydrogen, then heated to 80° C. and shaken for 20 h. Then the reaction was cooled, filtered through Celite™ and washed with MeOH. The filtrate was concentrated to give the crude product.

Step 5: (2S,3R)-methyl 3-cyclopropyl-3-(3-hydroxyphenyl)-2-methylpropanoate

To a solution of (2S,3S)-methyl 3-(3-(benzyloxy)phenyl)-3-cyclopropyl-2-methylpropanoate (4.81 g, 13 mmol) in methanol (67 ml) in a 25 ml glass shaker vessel, was 8% Pd-2% Pt/C (1.5 g, 35 wt % loading, 50 w/w, Johnson Matthey lot# F27N23). Then the vessel was evacuated and purged with nitrogen three times, and charged with 50 psi of hydrogen gas. The reaction was heated to 25° C. for 6 h, then filtered through Celite™, which was washed with MeOH (50 mL). The filtrate is concentrated to give the title compound.

Intermediate 2

(2S,3R)-methyl 3-cyclopropyl-3-(3-hydroxy-4-iodophenyl)-2-methylpropanoate

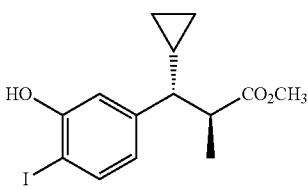 [SMILES: COC(=O)[C@@H](C)[C@H](c1ccc(I)c(O)c1)C1CC1]

A solution of (2S,3R)-methyl 3-cyclopropyl-3-(3-hydroxyphenyl)-2-methylpropanoate (1 g, 4.27 mmol) in DCM (10 mL) was cooled to 0° C., then NIS (0.960 g, 4.27 mmol) was added slowly over several minutes. After 2 h, the reaction was poured into saturated $Na_2SO_3$ (aq, 50 mL). The organic layer was separated, dried over $Na_2SO_4$ and concentrated. The resulting residue was purified by HPLC (ISCO 120 g, 0 to 50% EtOAc/Hex) to give the title compound. $^1$H NMR (500 MHz, $CDCl_3$) δ7.60 (d, 1H), 6.85 (s, 1H), 6.50 (d, 1H), 5.30 (br, 1H), 3.75 (s, 3H), 2.80 (m, 1H), 1.90 (t, 1H), 1.05 (m, 1H), 0.97 (d, 3H), 0.60 (m, 1H), 0.37 (m, 1H), 0.27 (m, 1H), 0.01 (m, 1H). (m/z): 361.07 $(M+H)^+$.

Intermediate 3

Methyl (2S,3R)-3-cyclobutyl-3-(3-hydroxy-4-iodophenyl)-2-methylpropanoate

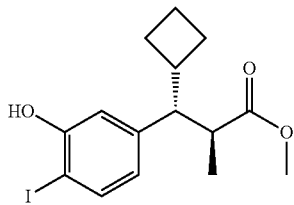

Step A: cyclobutyl(1H-imidazol-1-yl)methanone To a solution of cyclobutanecarboxylic acid (257 g, 2.57 mol) in THF (2600 mL) was added CDI (500 g, 3.08 mol) in portions at 10° C. After the addition, the mixture was stirred at 10° C. for 1 hr. Then the mixture was concentrated to afford cyclobutyl(1H-imidazol-1-yl)methanone, which was used in the next step.

Step B: 3-ethoxy-2-methyl-3-oxopropanoic acid A suspension of diethyl 2-methylmalonate (500.00 g, 2.87 mol, 1.00 eq) and KOH (177.16 g, 3.16 mol, 1.10 eq) in EtOH (5000 mL) was stirred at 70° C. for 12 hr. The reaction mixture was concentrated under vacuum. The resulting residue was diluted with water and the aqueous layer was extracted with EtOAc. The organic layer was separated, dried and concentrated to provide 3-ethoxy-2-methyl-3-oxopropanoic acid.

Step C: ethyl 3-cyclobutyl-2-methyl-3-oxopropanoate A suspension of 3-ethoxy-2-methyl-3-oxopropanoic acid (400 g, 2.74 mol) and $Mg(C_2H_5O)_2$ (313 g, 2.74 mol) in THF (4000 mL) was stirred at 70° C. for 12 hr. After the cooling down to 10° C., cyclobutyl(1H-imidazol-1-yl)methanone (702 g, crude) was added and the mixture was heated at reflux for 20 h. Then the mixture was filtered and the filtrate was concentrated. The resulting residue was diluted with DCM, washed with water and brine, dried and concentrated. The resulting residue was purified by silica gel chromatography to afford ethyl 3-cyclobutyl-2-methyl-3-oxopropanoate.

Step D: methyl 3-cyclobutyl-2-methyl-3-oxopropanoate A suspension of ethyl 3-cyclobutyl-2-methyl-3-oxopropanoate (321 g, 1.74 mol, 1.00 eq) and NaOMe (97.6 g, 1.74 mol, 1.00 eq) in MeOH (3200 mL) was stirred at 60° C. overnight. The mixture was concentrated and the resulting residue was diluted with DCM and water. The organic layer was separated and concentrated to provide a crude residue, which was purified by silica gel column chromatography to afford methyl 3-cyclobutyl-2-methyl-3-oxopropanoate.

Step E: 3-cyclobutyl-2-methyl-3-[[(4-methylbenzene)sulfonyl]oxy]prop-2-enoate To a solution of methyl 3-cyclobutyl-2-methyl-3-oxopropanoate (170.00 g, 998.79 mmol, 1.00 eq) in THF (2550 mL) at rt, NaHMDS (219.78 g, 1.20 mol, 1.20 Eq) was added drop wise. After the addition, the mixture was stirred at 0° C. for 30 min. Solid p-tolylsulfonyl 4-methylbenzenesulfonate (358.59 g, 1.10 mol) was added in portions at 0° C. and the mixture was stirred at 0° C. for 1 hr. The mixture was then poured into ice-water and extracted with DCM. The organic layer was separated, washed with brine and concentrated. The resulting residue was purified by silica gel column chromatography to afford 3-cyclobutyl-2-methyl-3-[[(4-methylbenzene)sulfonyl]oxy] prop-2-enoate.

Step G: methyl (Z)-3-cyclobutyl-3-(3-hydroxyphenyl)-2-methylacrylate To a 5 L, 4-necked round-bottom flask, purged and maintained with an inert atmosphere of nitrogen, were added a solution of methyl 3-cyclobutyl-2-methyl-3-[[(4-methylbenzene)sulfonyl]oxy]prop-2-enoate (295 g, 909.39 mmol, 1.00 eq) in 1,4-dioxane (2950 mL), 3-hydroxyphenylboronic acid (124.7 g, 904.09 mmol, 1.00 eq), 2N potassium carbonate (1357 mL, 3.00 equiv) and $Pd(PPh_3)_4$(52.6 g, 45.52 mmol, 0.05 equiv). The resulting solution was stirred for 1 h at 80° C. in an oil bath. Then the solids were filtered off, and the resulting filtrate was extracted with 3×800 mL of ethyl acetate. The organic layers combined, washed with 1×1000 mL of saturated aqueous $NH_4Cl$, dried over anhydrous sodium sulfate, filtered and concentrated under vacuum. The residue purified by silica gel chromatography (solvent: ethyl acetate/petroleum ether (1:2)) to afford (Z)-methyl 3-cyclobutyl-3-(3-hydroxyphenyl)-2-methylacrylate.

Step H: methyl (2S,3R)-3-cyclobutyl-3-(3-hydroxyphenyl)-2-methylpropanoate To a round bottomed flask, evacuated and purged with nitrogen three times, was added bis(2-methylallyl)(1,5-cyclooctadiene)ruthenium (II) (2.2 g, 6.89 mmol), followed by (R)-1-[(SP)-2-(diphenylphosphino)ferrocenyl]ethyldi-tert-butylphosphine (3.96 g, 7.29 mmol). Methanol (300 mL) was added to the flask and the mixture was stirred between 20 and 30° C. for 30 min under nitrogen.

Then tetrafluoroboric acid-diethylether complex (2.231 g, 13.78 mmol) was added dropwise to the mixture over a period of 10-20 min. The resulting mixture was stirred at 20 to 30° C. for 1 h under nitrogen. A separate flask was charged with (Z)-methyl 3-cyclobutyl-3-(3-hydroxyphenyl)-2-methylacrylate (100 g, 405 mmol). Methanol (500 mL) was added to this flask and argon was bubbled through the solution for 1 h to 2 h. To this solution was added, under argon, the ruthenium catalyst solution prepared in the first flask.

The resulting solution was evacuated and purged with argon three times, and was then evacuated and filled with hydrogen six times. The reaction mixture was then stirred at 80° C. for 19 h under hydrogen atmosphere (3.5 to 4.0 MPa).

The reaction mixture was cooled to between 20 and 30° C. and filtered through 50 g diatomite. The filtrate was concentrated to approximately 1-2 vol (milliliters solvent per grams of starting material). To this crude mixture was added MTBE (500 mL) and the mixture was concentrated again to approximately 1-2 vol. To this crude mixture was added MTBE (1000 mL) and the mixture was treated with decolorizing carbon overnight, filtered through 50 g diatomite then concentrated to approximately 1-2 vol. Then toluene (100 mL) was added to the solution, which was kept at a temperature between 25 and 30° C. Then heptane (600 mL) was added and the mixture was cooled to 15° C. and stirred for 3 to 6 hours. The resulting solid was collected via filtration and dried at 50-60° C. for 17 h to afford methyl (2S,3R)-3-cyclobutyl-3-(3-hydroxyphenyl)-2-methylpropanoate.

Step I: Methyl (2S,3R)-3-cyclobutyl-3-(3-hydroxy-4-iodophenyl)-2-methylpropanoate Methyl (2S,3R)-3-cyclobutyl-3-(3-hydroxy-4-iodophenyl)-2-methylpropanoate was prepared using a method similar to that outlined in the preparation of Intermediate 2 and starting from methyl (2S,3R)-3-cyclobutyl-3-(3-hydroxyphenyl)-2-methylpropanoate.

SCHEME 2

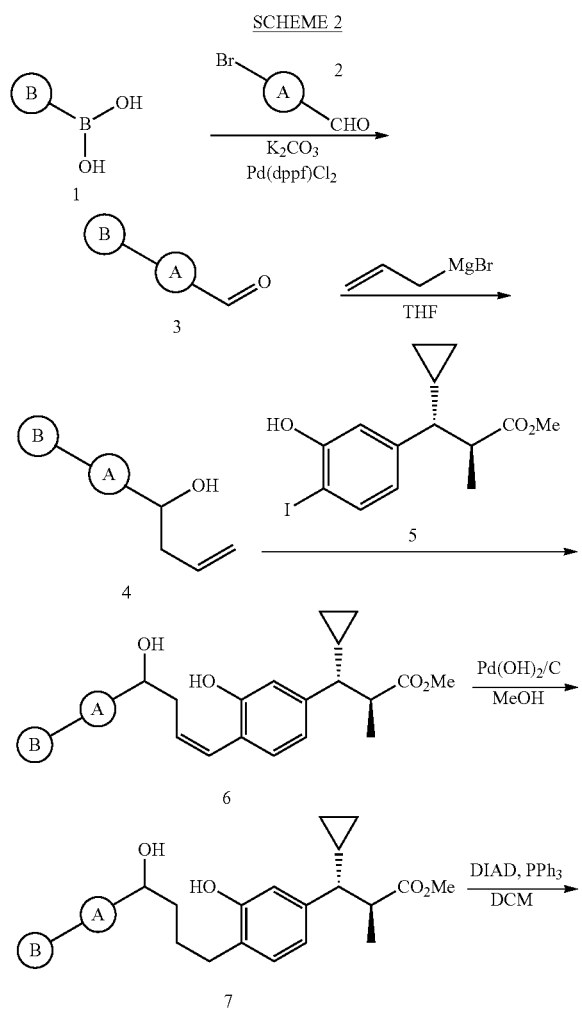

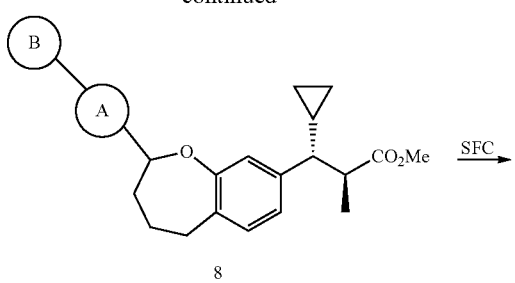

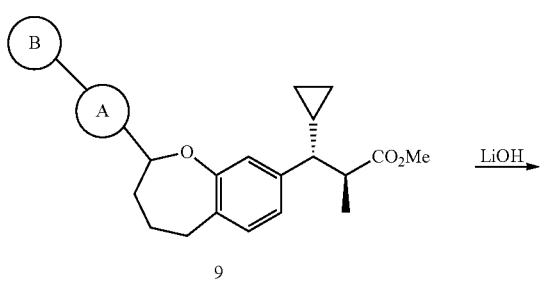

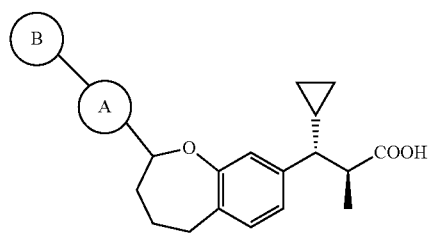

Scheme 2 provides a route to prepare the compounds of the present invention. Suzuki cross-coupling of boronic acid 1 and aldehyde 2, followed by allyl Grignard addition to aldehyde 3 delivered the homoallylic alcohol 4. Heck reaction of aryl iodide 5 with homoallylic alcohol 4 gave diol 6. Reduction of the alkene was achieved via palladium-mediated hydrogenation to give 7. An intramolecular Mitsonobu reaction resulted in ring closure to deliver the tetrahydrobenzoxapine ring 8. SFC separation of the benzylic diastereomers was followed by hydrolysis of the methyl ester to give the final compound 10.

SCHEME 3

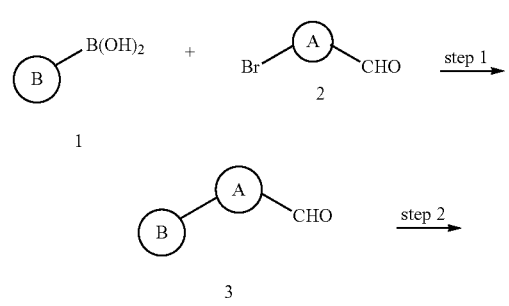

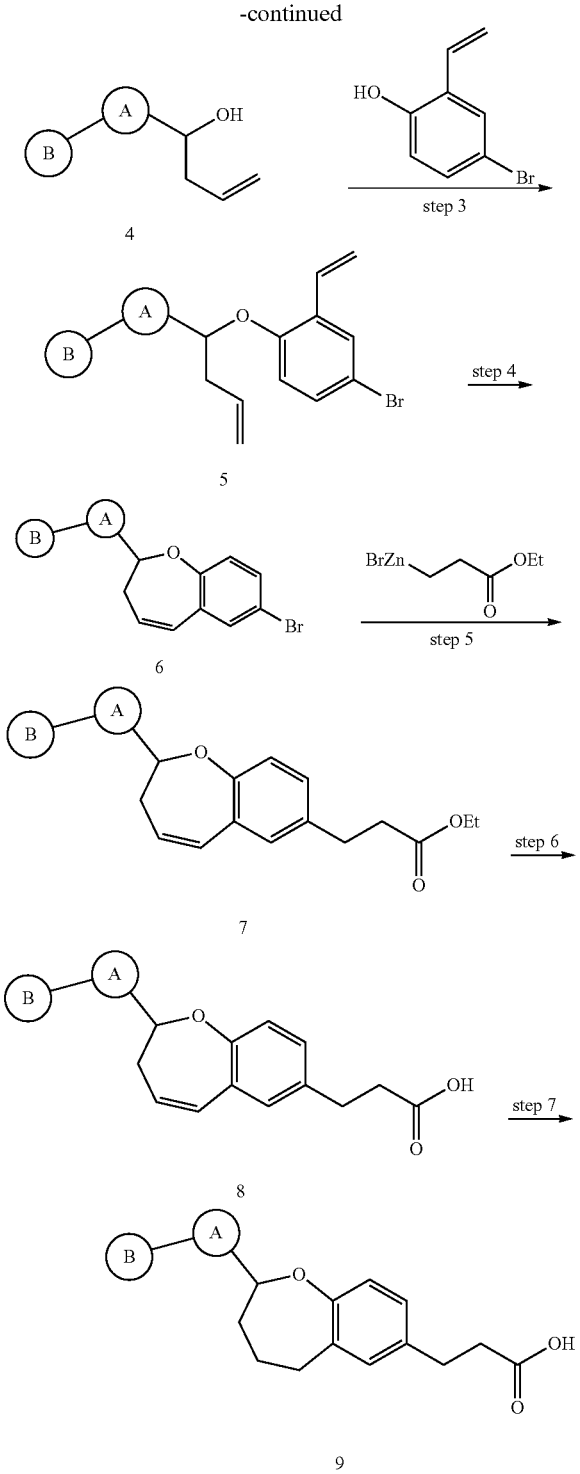

Step 1: Pd(PPh₃)₄, K₂CO₃, dioxane;
Step 2: allylMgBr, THF;
Step 3: PPh₃, DIAD, PhMe;
Step 4: Hoveyda-Grubbs 2, DCM;
Step 5: SPhos Pd precat, THF;
Step 6: LiOH, THF/H₂O/MeOH;
Step 7: H₂ (1 atm), Pd(OH)₂, EtOAc Scheme 3 provides an alternative route to prepare the compounds of the present invention. Suzuki cross-coupling of boronic acid 1 and aldehyde 2, followed by allyl Grignard addition to aldehyde 3 delivered the homoallylic alcohol 4. Mitsonobu coupling of the homoallylic alcohol 4 and 4-bromo-2-vinylphenol gave the aryl benzyl ether 5. Aryl benzyl ether 5 was subjected to ring-closing metathesis with catalytic Hoveyda-Grubbs 2 reagent to prepare dihyrdobenzoxapiene 6. The propanoic acid moiety was installed using a two step sequence consisting of Negishi reaction with (3-ethoxy-3-oxopropyl)zinc (II) bromide followed by lithium hydroxide-mediated hydrolysis of the ethyl ester to give acid 8. Finally, reduction of the dihydrobenzoxapiene double bond of 8 was achieved with hydrogenation in the presence of Pd(OH)₂ to provide compound 9.

EXAMPLE 1

(2S,3R)-3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoic acid

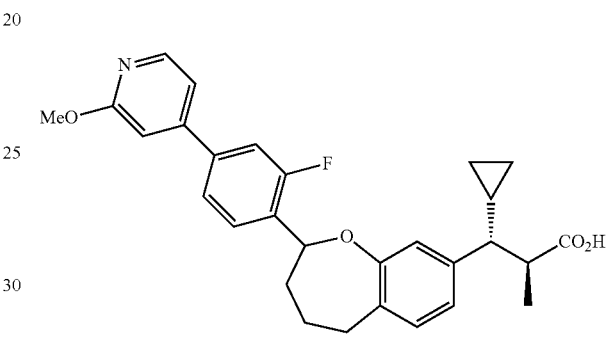

Step A: 1-(2-fluoro-4-(2-methoxypyridin-4-yl)phenyl) but-3-en-1-ol To a solution of 2-fluoro-4-(2-methoxypyridin-4-yl)benzaldehyde (1.00 g, 4.32 mmol) in THF (10 mL) was added allylmagnesium bromide (8.65 mL, 8.65 mmol, 1.0 M) dropwise at 0° C. under a N₂ atmosphere. The reaction mixture was stirred at 0° C. for 30 min, and at 20° C. for 3 hours. Then the reaction mixture was quenched with saturated NH₄Cl solution (20 mL) and extracted with EtOAc (10 mL×3). The combined organic layers were washed with brine (30 mL), dried over anhydrous Na₂SO₄ and filtered. The filtrate was concentrated in vacuo to give a residue, which was purified by preparative TLC (PE:EtOAc=5:1, v/v) to afford the title compound. ¹H NMR (400 MHz, CDCl₃): δ=8.23 (d, J=5.2 Hz, 1H), 7.60 (d, J=8.0 Hz, 1H), 7.44 (d, J=7.6 Hz, 1H), 7.30 (d, J=7.6 Hz, 1H), 7.09 (d, J=4.4 Hz, 1H), 6.93 (s, 1H), 5.89-5.82 (m, 1H), 5.23-5.19 (m, 2H), 5.13-5.11 (m, 1H), 3.99 (s, 3H), 2.63-2.49 (m, 2H).

Step B: (2S, 3R)-methyl 3-cyclopropyl-3-(4-((Z)-4-(2-fluoro-4-(2-methoxypyridin-4-yl) phenyl)-4-hydroxybut-1-en-1-yl)-3-hydroxyphenyl)-2-methylpropanoate To a solution of 1-(2-fluoro-4-(2-methoxypyridin-4-yl)phenyl)but-3-en-1-ol (804 mg, 2.94 mmol) and (2S, 3R)-methyl 3-cyclopropyl-3-(3-hydroxy-4-iodophenyl)-2-methylpropanoate (530 mg, 1.47 mmol) in toluene (10 mL) were added N-cyclohexyl-N-methylcyclohexanamine (575 mg, 2.94 mmol) and t-buxphos Pd G1 (CAS#1142811-12-8, 101 mg, 0.147 mmol) under a N₂ atmosphere. The reaction mixture was stirred at 100° C. for 2 hours, then cooled to room temperature and concentrated in vacuo to give a residue, which was purified by silica gel chromatography (eluted from PE:EtOAc=100:1 to 5:1, v/v) to afford the title compound. ¹H NMR (400 MHz, CDCl₃): δ=8.22 (d, J=5.2 Hz, 1H), 7.65-7.61 (m, 1H), 7.45 (d, J=7.2 Hz, 1H), 7.32-7.29 (m, 1H), 7.26-7.25 (m, 1H), 7.08 (d, J=5.6 Hz, 1H), 6.94 (s, 1H), 6.73-6.69 (m, 2H), 6.61 (s, 1H), 6.24-6.16 (m, 1H), 5.21-5.18 (m, 1H), 3.99 (s, 3H), 3.73 (s, 3H), 2.80-2.66 (m, 3H), 2.32-2.26 (m, 1H), 1.88-1.83 (m, 1H), 1.08-1.07 (m, 1H), 0.84 (d, J=4.0 Hz, 3H), 0.57-0.55 (m, 1H), 0.36-0.30 (m, 1H), 0.25-0.22 (m, 1H), 0.01-0.03 (m, 1H).

Step C: (2S, 3R)-methyl 3-cyclopropyl-3-(4-(4-(2-fluoro-4-(2-methoxypyridin-4-yl) phenyl)-4-hydroxybutyl)-3-hydroxyphenyl)-2-methylpropanoate To a solution of (2S, 3R)-methyl 3-cyclopropyl-3-(4-((Z)-4-(2-fluoro-4-(2-methoxypyridin-4-yl) phenyl)-4-hydroxybut-1-en-1-yl)-3-hydroxyphenyl)-2-methylpropanoate (610 mg, 1.21 mmol) in MeOH (10 mL) was added Pd(OH)$_2$/C (85.0 mg, 20%). The reaction mixture was stirred for at 20° C. for 3 hours under H$_2$ balloon pressure. Then the reaction mixture was filtered, and the filtrate was concentrated in vacuo to give the title compound, which was used in the next step. $^1$H NMR (400 MHz, CDCl$_3$): δ=8.20 (d, J=6.0 Hz, 1H), 7.58 (t, J=7.6 Hz, 1H), 7.41 (dd, J$_{13}$=8.0 Hz, J$_{12}$=2.0 Hz, 1H), 7.28 (dd, J$_{13}$=11.2 Hz, J$_{12}$=2.0 Hz, 1H), 7.07 (dd, J$_{13}$=7.2 Hz, J$_{12}$=1.6 Hz, 1H), 7.01 (d, J=8.0 Hz, 1H), 6.92 (s, 1H), 6.65 (d, J=8.0 Hz, 1H), 6.61 (s, 1H), 5.17 (t, J=6.0 Hz, 1H), 3.99 (s, 3H), 3.72 (s, 3H), 2.80-2.65 (m, 3H), 1.88-1.74 (m, 6H), 1.05-0.97 (m, 1H), 0.93 (d, J=6.8 Hz, 3H), 0.56-0.51 (m, 1H), 0.34-0.20 (m, 2H), 0.02-0.02 (m, 1H).

Step D: (2S, 3R)-methyl 3-cyclopropyl-3-(2-(2-fluoro-4-(2-methoxypyridin-4-yl) phenyl)-2, 3, 4, 5-tetrahydrobenzo[b]oxepin-8-yl)-2-methylpropanoate To a solution of (2S, 3R)-methyl 3-cyclopropyl-3-(4-(4-(2-fluoro-4-(2-methoxypyridin-4-yl) phenyl)-4-hydroxybutyl)-3-hydroxyphenyl)-2-methylpropanoate (400 mg, 0.788 mmol) and triphenylphosphine (289 mg, 1.10 mmol) in DCM (3.0 mL) was added dropwise a solution of diisopropyl azodicarboxylate (0.215 mL, 1.10 mmol) in DCM (1.0 mL) at 0° C. under a N$_2$ atmosphere. The reaction mixture was stirred at 20° C. for 2 hours, then concentrated in vacuo to give a residue, which was purified by preparative TLC (PE:EtOAc=5:1, v/v) to afford the title compound. $^1$H NMR (400 MHz, CDCl$_3$): δ=8.25 (d, J=5.2 Hz, 1H), 7.79 (t, J=8.0 Hz, 1H), 7.41 (dd, J$_{13}$=8.4 Hz, J$_{12}$=2.0 Hz, 1H), 7.33-7.30 (m, 1H), 7.11-7.09 (m, 2H), 6.96 (s, 1H), 6.84-6.79 (m, 2H), 4.96-4.92 (m, 1H), 4.00 (s, 3H), 3.71 (s, 3H), 3.00 (t, J=12.8 Hz, 1H), 2.83-2.76 (m, 2H), 2.24-2.21 (m, 1H), 2.15-2.09 (m, 2H), 1.87 (t, J=10.0 Hz, 1H), 1.72-1.69 (m, 1H), 1.06-0.99 (m, 1H), 0.94 (dd, J$_{13}$=6.8 Hz, J$_{12}$=5.6 Hz, 3H), 0.57-0.50 (m, 1H), 0.36-0.29 (m, 1H), 0.25-0.19 (m, 1H), 0.04-0.04 (m, 1H).

Step E: (2S, 3R)-methyl 3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoate (Peak 1, faster eluting); and (2S, 3R)-methyl 3-cyclopropyl-3-((S or R)-2-(2-fluoro-4-(2-methoxypyridin-4-yl)phenyl)-2,3,4,5-tetrahydrobenzo[b]oxepin-8-yl)-2-methylpropanoate (Peak 2, slower eluting)

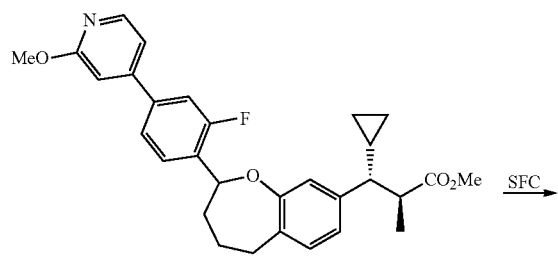

-continued

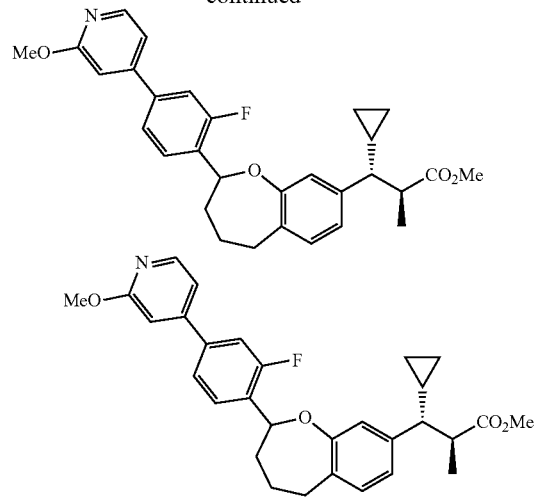

(2S, 3R)-methyl 3-cyclopropyl-3-(2-(2-fluoro-4-(2-methoxypyridin-4-yl)phenyl)-2,3,4,5-tetrahydrobenzo[b]oxepin-8-yl)-2-methylpropanoate (200 mg, 0.409 mmol) was separated via SFC (using SFC conditions: "Column: Chiralpak AD-3 50*4.6 mm I.D., 3 um Mobile phase: ethanol (0.05% DEA) in CO$_2$ from 5% to 40% Flow rate: 4 mL/min Wavelength: 220 nm") to give (2S, 3R)-methyl 3-cyclopropyl-3-((R or S)-2-(2-fluoro-4-(2-methoxypyridin-4-yl)phenyl)-2,3,4,5-tetrahydrobenzo[b]oxepin-8-yl)-2-methyl-propanoate (Peak 1, faster eluting), and (2S, 3R)-methyl 3-cyclopropyl-3-((S or R)-2-(2-fluoro-4-(2-methoxypyridin-4-yl)phenyl)-2,3,4,5-tetrahydrobenzo[b]oxepin-8-yl)-2-methyl-propanoate (Peak 2, slower eluting).

Step F: (2S,3R)-methyl 3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoic acid To a solution of (2S, 3R)-methyl 3-cyclopropyl-3-((R or S)-2-(2-fluoro-4-(2-methoxypyridin-4-yl)phenyl)-2,3,4,5-tetrahydro-benzo[b]oxepin-8-yl)-2-methyl-propanoate (Peak 1, faster eluting, 100 mg, 0.204 mmol) in THF/MeOH/H$_2$O (1.0 mL/1.0 mL/1.0 mL) was added LiOH (48.9 mg, 2.04 mmol). The reaction mixture was stirred at 50° C. for 16 hours, and then cooled to room temperature. The reaction mixture was then acidified with HCl (1.0 N) to adjust the pH to 2, and was extracted with EtOAc (5.0 mL×3). The combined organic layers were concentrated in vacuo to afford a residue, which was purified by preparative HPLC (on a GILSON 281 instrument fitted with a Phenomenex Gemini C$_{18}$ (250*21.2 mm*5 um) using water and acetonitrile as the eluents. Mobile phase A: water (neutral), mobile phase B: acetonitrile. Gradient: 33-63% B, 0-10 min; 100% B, 10.5-12.5 min; 5% B, 13-15 min) to give (2S,3R)-3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoic acid. $^1$H NMR (400 MHz, CDCl$_3$): δ=8.25 (d, J=4.8 Hz, 1H), 7.79 (t, J=8.0 Hz, 1H), 7.47 (d, J=7.2 Hz, 1H), 7.30 (d, J=11.2 Hz, 1H), 7.12-7.10 (m, 2H), 6.96 (s, 1H), 6.84-6.83 (m, 2H), 4.92 (d, J=10.0 Hz, 1H), 4.00 (s, 3H), 3.00 (t, J=13.2 Hz, 1H), 2.83-2.79 (m, 2H), 2.24-2.09 (m, 3H), 1.94 (t, J=10.0 Hz, 1H), 1.75-1.66 (m, 1H), 1.10-1.08 (m, 1H), 0.98 (d, J=6.8 Hz, 3H), 0.61-0.60 (m, 1H), 0.36-0.33 (m, 2H), 0.03-0.02 (m, 1H).

To a solution of (2S,3R)-3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoic acid in MeCN (1.0 mL) and water (1.0 mL) was added aq. NaOH (1.0 eq, 0.5 M). The mixture was stirred at 20° C. for 1 hour. Then the reaction mixture was lyophilized to give the sodium salt of the title compound.

Step B: tert-butyl 3-(4-(4-((1R, 2S)-1-cyclopropyl-3-methoxy-2-methyl-3-oxopropyl)-2-hydroxyphenyl) butanoyl) azetidine-1-carboxylate To a solution of tert-butyl 3-(1-hydroxybut-3-en-1-yl)azetidine-1-carboxylate (2.27 g,

TABLE 1

Example 2 was prepared from (2S, 3R)-methyl-3-cyclopropyl-3-((S or R)-2-(2-fluoro-4-(2-methoxypyridin-4-yl)phenyl)-2,3,4,5-tetrahydrobenzo[b]oxepin-8-yl)-2-methyl-propanoate (Peak 2, slower eluting isomer) in a similar manner to Example 1.

| Example | Structure | MW | Compound Name | LC/MS (ESI) observed [M + 1]+ |
|---|---|---|---|---|
| 2 | 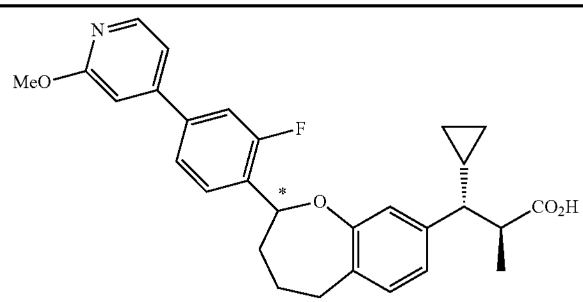 | 475.55 | (2S,3R)-3-cyclopropyl-3-((R or S)-2-(2-fluoro-4-(2-methoxypyridin-4-yl)phenyl)-2,3,4,5-tetrahydrobenzo[b]oxepin-8-yl)-2-methylpropanoic acid | 476.2 |

*stereoisomer at this position

EXAMPLES 3 and 4

(2S, 3R)-3-((R or S)-2-(1-(2, 5-bis (trifluoromethyl) benzyl) azetidin-3-yl)-2, 3, 4, 5-tetrahydrobenzo[b] oxepin-8-yl)-3-cyclopropyl-2-methylpropanoic acid (Example 3: peak 1, faster eluting isomer), and
(2S, 3R)-3-((R or S)-2-(1-(2, 5-bis (trifluoromethyl) benzyl) azetidin-3-yl)-2, 3, 4, 5-tetrahydrobenzo[b] oxepin-8-yl)-3-cyclopropyl-2-methylpropanoic acid (Example 4: peak 2, slower eluting isomer)

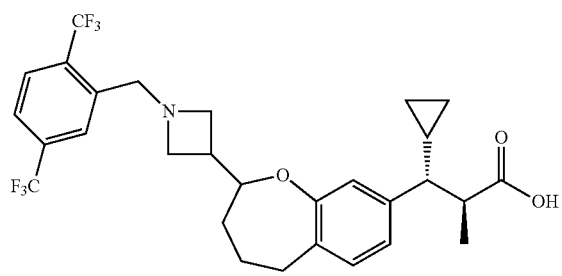 [SMILES: C[C@H](C(=O)O)[C@H](c1ccc2c(c1)OC(C1CN(Cc3cc(C(F)(F)F)ccc3C(F)(F)F)C1)CCC2)C1CC1]

Step A: tert-butyl 3-(1-hydroxybut-3-en-1-yl) azetidine-1-carboxylate

To a solution of tert-butyl 3-formylazetidine-1-carboxylate (2.00 g, 10.8 mmol) in THF (20 mL) was added dropwise allylmagnesium bromide (21.6 mL, 21.6 mmol) at 0° C. under a $N_2$ atmosphere. The reaction mixture was stirred for 30 min at 0° C. and 3 hours at 20° C. (room temperature). Then the reaction mixture was quenched with saturated $NH_4Cl$ (20 mL) and extracted with EtOAc (10 mL×3). The combined organic layers were washed with brine (50 mL), dried over anhydrous $Na_2SO_4$ and filtered. The filtrate was concentrated in vacuo to give the title compound, which was used in the next step. $^1H$ NMR (400 MHz, $CDCl_3$): δ=5.85-5.75 (m, 1H), 5.19-5.04 (m, 2H), 4.14-3.71 (m, 6H), 2.24-2.04 (m, 2H), 1.44 (s, 9H).

9.99 mmol) in DMF (20 ml) were added lithium chloride (1.05 g, 24.9 mmol), lithium acetate (1.65 g, 24.9 mmol), (2S,3R)-methyl 3-cyclopropyl-3-(3-hydroxy-4-iodophenyl)-2-methyl propanoate (3.00 g, 8.33 mmol), tetrabutylammonium chloride (4.63 g, 16.6 mmol) and $PdOAc_2$ (0.374 g, 1.66 mmol) under a $N_2$ atmosphere. The reaction mixture was stirred for 2 hours at 100° C., then diluted with water (20 mL). The mixture was extracted with EtOAc (30 mL×3). The combined organic layers were washed with water (100 mL) twice. Then the organic layer was concentrated in vacuo to give crude product, which was purified via silica gel column (PE:EtOAc=20:1) to give the title compound. MS (ESI) m/z: 482.2 [M+Na$^+$].

Step C: tert-butyl 3-(4-(4-((1R, 2S)-1-cyclopropyl-3-methoxy-2-methyl-3-oxopropyl)-2-hydroxyphenyl)-1-hydroxybutyl) azetidine-1-carboxylate A mixture of compound tert-butyl 3-((E)-4-(4-((1 R,2 S)-1-cyclopropyl-3-methoxy-2-methyl-3-oxopropyl)-2-hydroxyphenyl)-1-hydroxybut-3-en-1-yl) azetidine-1-carboxylate (100 mg, 0.218 mmol) and $PdOH_2$/C (1.528 mg, 20%) in MeOH (10 ml) was stirred at 15° C. for 16 hours under $H_2$ atmosphere. The mixture was filtered, and the filtrate was dried over $MgSO_4$ and concentrated in vacuo to give the crude product. The crude product was purified by prep-TLC (PE:EtOAc=3:1) to give the title compound. MS (ESI) m/z: 462.3 [M+H$^+$].

Step D: tert-butyl 3-(8-((1R, 2S)-1-cyclopropyl-3-methoxy-2-methyl-3-oxopropyl)-2, 3, 4, 5-tetrahydrobenzo [b]oxepin-2-yl) azetidine-1-carboxylate To a solution tert-butyl 3-(4-(4-((1R, 2S)-1-cyclopropyl-3-methoxy-2-methyl-3-oxopropyl)-2-hydroxyphenyl)-1-hydroxybutyl) azetidine-1-carboxylate (453 mg, 0.981 mmol) and triphenylphosphine (515 mg, 1.96 mmol) in DCM (8.0 mL) was added a solution of (E)-diisopropyl diazene-1,2-dicarboxylate (397 mg, 1.96 mmol) in DCM (2.0 mL) at 0° C. under $N_2$ atmosphere. The reaction mixture was stirred for 1 hour at 20° C., then concentrated in vacuo to give a residue, which was purified by prep-TLC(PE:EtOAc=5:1) to give the title compound.

Step E: (2S, 3R)-methyl 3-(2-(azetidin-3-yl)-2, 3, 4, 5-tetrahydrobenzo[b]oxepin-8-yl)-3-cyclopropyl-2-methylpropanoate To a solution of tert-butyl 3-(8-(1-cyclopropyl-3-methoxy-2-methyl-3-oxopropyl)-2, 3, 4, 5-tetrahydrobenzo[b]oxepin-2-yl) azetidine-1-carboxylate (60.0 mg, 0.135 mmol) in DCM (10 ml) was added 2, 2, 2-trifluoroacetic acid (308 mg, 2.71 mmol). Then the mixture was stirred at 20° C. for 30 min, and concentrated in vacuo to give the title compound, which was used in next step. MS (ESI) m/z: 344.1 [M+H⁺].

Step F: (2S, 3R)-methyl 3-(2-(1-(2, 5-bis (trifluoromethyl) benzyl) azetidin-3-yl)-2, 3, 4, 5-tetrahydrobenzo[b]oxepin-8-yl)-3-cyclopropyl-2-methylpropanoate A mixture of compound K₂CO₃ (66.0 mg, 0.477 mmol), 2-(bromomethyl)-1,4-bis (trifluoromethyl)benzene (110 mg, 0.358 mmol) and methyl 3-(2-(azetidin-3-yl)-2,3,4,5-tetrahydrobenzo[b]oxepin-8-yl)-3-cyclopropyl-2-methylpropanoate (41.0 mg, 0.119 mmol) in MeCN (10 ml) was stirred at 20° C. for 10 hours. Then water (10 mL) was added, and the reaction mixture was extracted with DCM (5 ml) twice. The combined organic layers were dried over Na₂SO₄, and concentrated in vacuo to give the crude product. The crude product was purified via prep-TLC (PE:EtOAc=5:1) to give the title compound. MS (ESI) m/z: 570.2 [M+H⁺].

Step G: (2S, 3R)-3-(2-(1-(2, 5-bis (trifluoromethyl) benzyl) azetidin-3-yl)-2, 3, 4, 5-tetrahydrobenzo[b]oxepin-8-yl)-3-cyclopropyl-2-methylpropanoic acid A mixture of LiOH (17.24 mg, 0.720 mmol) and (2S,3R)-methyl 3-(2-(1-(2,5-bis(trifluoromethyl)benzyl)azetidin-3-yl)-2,3,4,5-tetrahydrobenzo[b]oxepin-8-yl)-3-cyclopropyl-2-methylpropanoate (41 mg, 0.072 mmol) in water (1.0 mL), THF (1.0 mL) and MeOH (1.0 mL) was stirred at 50° C. for 2 hours. The reaction mixture was then acidified with HCl (2N, 1.0 mL) and diluted with DCM (10 mL). Then the reaction mixture was washed with water (20 ml). The organic layer was separated, dried over anhydrous MgSO₄ and filtered. The filtrate was concentrated to give the crude product, which was purified by prep-HPLC (on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile. Gradient: 32-58% B, 0-10 min; 100% B, 10.5-12.5 min; 5% B, 13-15 min) to give the title compound. ¹H NMR (400 MHz, CDCl₃): δ=8.15 (s, 1H), 7.93-7.80 (m, 2H), 7.10 (d, J=6.4 Hz, 2H), 6.87-6.78 (m, 2H), 4.74-4.58 (m, 4H), 4.12 (s, 2H), 3.65 (s, 1H), 3.22 (s, 1H), 2.87-2.76 (m, 3H), 2.00 (s, 2H), 1.81-1.78 (m, 1H), 1.61-1.51 (m, 2H), 1.01-1.00 (m, 4H), 0.63-0.62 (m, 1H), 0.38-0.37 (m, 2H), 0.05-0.04 (m, 1H).

Step H: (2S, 3R)-3-((R or S)-2-(1-(2,5-bis(trifluoromethyl)benzyl)azetidin-3-yl)-2,3,4,5-tetrahydrobenzo[b]oxepin-8-yl)-3-cyclopropyl-2-methylpropanoic acid and (2S, 3R)-3-((R or S)-2-(1-(2,5-bis(trifluoromethyl)benzyl)azetidin-3-yl)-2,3,4,5-tetrahydrobenzo[b]oxepin-8-yl)-3-cyclopropyl-2-methylpropanoic acid

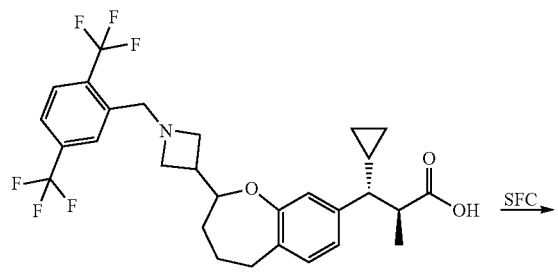

SFC→

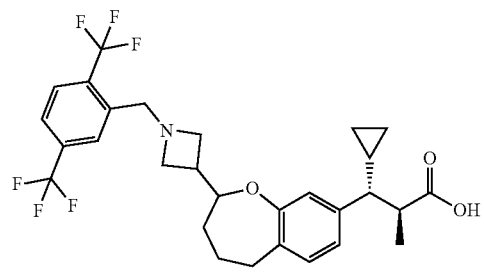

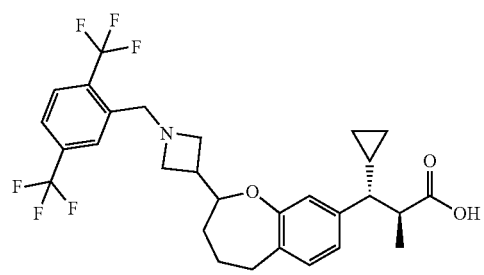

(2S, 3R)-3-(2-(1-(2,5-bis(trifluoromethyl)benzyl)azetidin-3-yl)-2,3,4,5-tetrahydro-benzo[b]oxepin-8-yl)-3-cyclopropyl-2-methylpropanoic acid and (25 mg, 0.045 mmol) was separated via SFC (SFC conditions: Instrument: Berger MultiGram™ SFC, Mettler Toledo Co, Ltd, column: AD (250*30 mm 5 um), mobile phase: 10% EtOH+NH₃H₂O 50 mL/min; wavelength: 220 nm) to give 2 peaks: peak 1 (faster eluting isomer; Example 3): (2S,3R)-3-((R or S)-2-(1-(2,5-bis(trifluoromethyl)benzyl)-azetidin-3-yl)-2,3,4,5-tetrahydrobenzo[b]oxepin-8-yl)-3-cyclopropyl-2-methylpropanoic acid, and peak 2 (slower eluting isomer; Example 4): (2S, 3R)-3-((R or S)-2-(1-(2,5-bis(trifluoromethyl)-benzyl)azetidin-3-yl)-2,3,4,5-tetrahydrobenzo[b]oxepin-8-yl)-3-cyclopropyl-2-methylpropanoic acid. To the faster eluting isomer (Example 3) (2S,3R)-3-((R or S)-2-(1-(2,5-bis(trifluoromethyl)-benzyl)azetidin-3-yl)-2,3,4,5-tetrahydrobenzo[b]oxepin-8-yl)-3-cyclopropyl-2-methylpropanoic acid (9 mg, 0.016 mmol) was added a solution of NaOH (aq. 33 mg, 0.5 M) in MeCN (0.5 mL). The mixture was stirred for 1 hour at room temperature. Then the reaction mixture was lyophilized to give the sodium salt of Example 3. ¹H NMR (400 MHz, CDCl₃): δ=8.00 (s, 1H), 7.77 (d, J=7.2 Hz, 1H), 7.62 (d, J=6.8 Hz, 1H), 7.06 (d, J=6.8 Hz, 1H), 6.84 (d, J=6.8 Hz, 1H), 3.96 (s, 2H), 3.74-3.64 (m, 3H), 3.40-3.39 (m, 1H), 3.13-3.13 (m, 1H), 2.84-2.73 (m, 4H), 2.05-1.99 (m, 2H), 1.86-1.83 (m, 1H), 1.64-1.50 (m, 2H), 1.16-1.15 (m, 1H), 1.00 (d, J=5.6 Hz, 3H), 0.61-0.60 (m, 1H), 0.38-0.37 (m, 2H), 0.06-0.05 (m, 1H).

To a solution of the slower eluting isomer (Example 4) (2S,3R)-3-((R or S)-2-(1-(2,5-bis(trifluoro-methyl)benzyl)azetidin-3-yl)-2,3,4,5-tetrahydrobenzo[b]oxepin-8-yl)-3-cyclopropyl-2-methylpropanoic acid (10 mg, 0.017 mmol) in MeCN (0.5 mL) was added the solution of NaOH (aq. 37 mg, 0.5 M). The mixture was stirred for 1 hour at room temperature. Then the reaction mixture was lyophilized to give the sodium salt of Example 4. MS (ESI) m/z: 556.1 [M+H]⁺.

TABLE 2

Example 4 was prepared as described above

| Example | Structure | MW | Compound Name | LC/MS (ESI) observed [M + 1]+ |
|---|---|---|---|---|
| 4 | 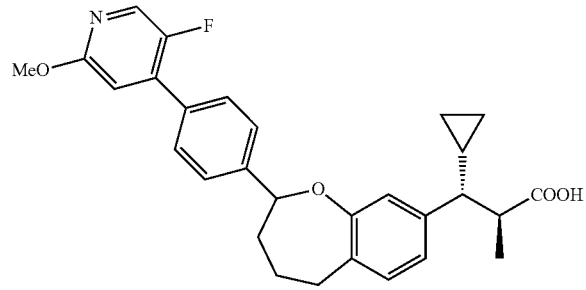 [SMILES: COc1cc(-c2ccc(C3CCCc4ccc([C@H](C5CC5)[C@H](C)C(=O)O)cc4O3)cc2)c(F)cn1] | 555.55 | (2S,3R)-3-((R or S)-2-(1-(2,5-bis(trifluoromethyl)-benzyl)azetidin-3-yl)-2,3,4,5-tetrahydrobenzo[b]-oxepin-8-yl)-3-cyclopropyl-2-methylpropanoic acid | 556.1 |

*stereoisomer at this position

EXAMPLE 5

(2S,3R)-3-cyclopropyl-3-((RS)-2-(4-(5-fluoro-2-methoxypyridin-4-yl)phenyl)-2,3,4,5-tetrahydrobenzo[b]oxepin-8-yl)-2-methylpropanoic acid Step A: 4-(5-fluoro-2-methoxypyridin-4-yl)benzaldehyde To a solution of compounds (5-fluoro-2-methoxypyridin-4-yl)boronic acid (800 mg, 4.68 mmol) and 4-bromobenzaldehyde (1.03 g, 5.62 mmol) in THF (10 mL) and water (2.0 mL) were added $K_2CO_3$ (1.93 g, 14.0 mmol) and $PdCl_2$(dppf) (342 mg, 0.468 mmol) under a $N_2$ atmosphere. The reaction mixture was stirred at 100° C. for 2 hours, then water (10 mL) was added and the mixture was extracted with EtOAc (2 mL×3). The combined organic layers were washed with brine (10 mL), dried over anhydrous $Na_2SO_4$ and filtered. The filtrate was concentrated in vacuo to give a residue, which was purified by preparative TLC (PE/EtOAc=5:1) to give the title compound. $^1$H NMR (400 MHz, CDCl$_3$): δ=10.1 (s, 1H), 8.12 (s, 1H), 8.01 (d, J=8.0 Hz, 2H), 7.77 (d, J=7.2 Hz, 2H), 6.85 (d, J=5.2 Hz, 1H), 3.97 (s, 3H). MS(ESI) m/z: 232.0 [M+H]$^+$.

Step B: 1-(4-(5-fluoro-2-methoxypyridin-4-yl)phenyl)but-3-en-1-ol To a solution of 4-(5-fluoro-2-methoxypyridin-4-yl)benzaldehyde (650 mg, 2.81 mmol) in THF (10 mL) was added allylmagnesium bromide (11.2 mL, 11.2 mmol) dropwise at 0° C. under a $N_2$ atmosphere. The reaction mixture was stirred for 30 mins at 0° C., and 3 hours at room temperature. Then the reaction was quenched with saturated $NH_4Cl$ (20 mL) and extracted with EtOAc (5.0 mL×3). The combined organic layers were washed with brine (30 mL), dried over anhydrous $Na_2SO_4$ and filtered. The filtrate was concentrated in vacuo to give a residue, which was purified by preparative TLC (PE:EtOAc=5:1, v/v) to afford the title compound. $^1$H NMR (400 MHz, CDCl$_3$): δ=8.07 (s, 1H), 7.60 (d, J=7.6 Hz, 2H), 7.50 (d, J=7.6 Hz, 1H), 6.85 (m, 1H), 5.88-5.80 (m, 1H), 6.93 (s, 1H), 5.24 (t, J=10.4 Hz, 2H), 4.83 (d, J=7.6 Hz, 1H), 3.97 (s, 3H), 2.61 (m, 2H). MS(ESI) m/z: 274.1 [M+H]$^+$.

Step C: (2S,3R)-methyl-3-cyclopropyl-3-(4-((Z)-4-(4-(5-fluoro-2-methoxypyridin-4-yl)phenyl)-4-hydroxybut-1-en-1-yl)-3-hydroxyphenyl)-2-methylpropanoate To a solution of 1-(4-(5-fluoro-2-methoxypyridin-4-yl)phenyl)but-3-en-1-ol (620 mg, 2.27 mmol) and (2S, 3R)-methyl 3-cyclopropyl-3-(3-hydroxy-4-iodophenyl)-2-methylpropanoate (545 mg, 1.51 mmol) in toluene (10 mL) were added N-cyclohexyl-N-methylcyclohexanamine (443 mg, 2.27 mmol) and t-buxhos-palladacycle (104 mg, 0.151 mmol) under a $N_2$ atmosphere. The reaction mixture was stirred for 2 hours at 100° C., then cooled to room temperature and concentrated in vacuo to give a residue. The residue was purified via silica gel chromatography (eluted from PE:EtOAc=100:1 to 5:1, v/v) to afford the title compound. MS(ESI) m/z: 506.2 [M+H]$^+$.

Step D: (2S, 3R)-methyl 3-cyclopropyl-3-(4-(4-(2-fluoro-4-(2-methoxypyridin-4-yl) phenyl)-4-hydroxybutyl)-3-hydroxyphenyl)-2-methylpropanoate To a solution of (2S, 3R)-methyl (2S,3R)-methyl 3-cyclopropyl-3-(4-((Z)-4-(4-(5-fluoro-2-methoxypyridin-4-yl)phenyl)-4-hydroxybut-1-en-1-yl)-3-hydroxyphenyl)-2-methylpropanoate (450 mg, 0.890 mmol) in MeOH (10 mL) was added Pd(OH)$_2$/C (13.0 mg, 0.0890 mmol, 20%). The reaction mixture was stirred for 3 hours at room temperature under a $H_2$ balloon. Then the reaction mixture was filtered, and the filtrate was concentrated in vacuo to give the title compound, which was used in the next step. $^1$H NMR (400 MHz, CDCl$_3$): δ=8.05 (s, 1H), 7.57 (d, J=7.6 Hz, 2H), 7.46 (d, J=8.4 Hz, 2H), 7.03 (d, J=7.2 Hz, 1H), 6.81 (d, J=5.2 Hz, 1H), 6.65-6.61 (m, 2H), 4.86 (d, J=6.8 Hz, 1H), 3.94 (s, 3H), 3.74 (s, 3H), 2.80-2.72 (m, 3H), 1.86-1.72 (m, 4H), 1.03-0.93 (m, 4H), 0.54 (s, 1H), 0.32-0.21 (m, 2H), 0.01-0.004 (m, 1H). MS(ESI) m/z: 508.2 [M+H]$^+$.

Step E: (2S,3R)-methyl 3-cyclopropyl-3-(2-(4-(5-fluoro-2-methoxypyridin-4-yl)phenyl)-2,3,4,5-tetrahydrobenzo[b]

oxepin-8-yl)-2-methylpropanoate To a solution of (2S,3R)-methyl 3-cyclopropyl-3-(4-(4-(4-(5-fluoro-2-methoxypyridin-4-yl)phenyl)-4-hydroxybutyl)-3-hydroxyphenyl)-2-methylpropanoate (345 mg, 0.680 mmol) and triphenylphosphine (357 mg, 1.36 mmol) in DCM (3.0 mL) was added dropwise a solution of DIAD (275 mg, 1.36 mmol) in DCM (1.0 mL) at 0° C. under a $N_2$ atmosphere. The reaction mixture was stirred for 2 hours at room temperature, then concentrated in vacuo to give a residue, which was purified by preparative TLC (PE:EtOAc=5:1, v/v) to afford the title compound. $^1$H NMR (400 MHz, $CDCl_3$): δ=8.09 (s, 1H), 7.65-7.58 (m, 4H), 7.12 (d, J=7.2 Hz, 1H), 6.86-6.79 (m, 3H), 4.68 (t, J=5.6 Hz, 1H), 3.97 (s, 3H), 3.72 (s, 3H), 3.00 (t, J=13.2 Hz, 1H), 2.82-2.78 (m, 2H), 2.22-2.12 (m, 4H), 1.87 (t, J=10.0 Hz, 1H), 1.72-1.62 (m, 1H), 1.04 (d, J=4.8 Hz, 1H), 0.94 (t, J=5.6 Hz, 3H), 0.55 (d, J=3.6 Hz, 1H), 0.34 (d, J=4.0 Hz, 1H), 0.23 (d, J=4.4 Hz, 1H), 0.12 (s, 1H); MS(ESI) m/z: 490.3[M+H]$^+$.

Step F: (2S,3R)-methyl 3-cyclopropyl-3-(2-(4-(5-fluoro-2-methoxypyridin-4-yl)phenyl)-2,3,4,5-tetrahydrobenzo[b]oxepin-8-yl)-2-methylpropanoate ((2S,3R)-methyl 3-cyclopropyl-3-((RS)-2-(4-(5-fluoro-2-methoxypyridin-4-yl)phenyl)-2,3,4,5-tetrahydrobenzo[b]oxepin-8-yl)-2-methylpropanoate (60 mg, 0.123 mmol) was separated by SFC (SFC conditions: Column: Chiralpak AD-3 50*4.6 mm I.D., 3 um Mobile phase: ethanol (0.05% DEA) in $CO_2$ from 5% to 40% Flow rate: 4 mL/min Wavelength: 220 nm) to give 2 peaks: Peak 1 (faster eluting isomer): (2S,3R)-methyl 3-cyclopropyl-3-((RS)-2-(4-(5-fluoro-2-methoxypyridin-4-yl)phenyl)-2,3,4,5-tetrahydro-benzo[b]oxepin-8-yl)-2-methylpropanoate; and Peak 2 (slower eluting isomer): (2S,3R)-methyl 3-cyclopropyl-3-((RS)-2-(4-(5-fluoro-2-methoxypyridin-4-yl)phenyl)-2,3,4,5-tetrahydrobenzo[b]oxepin-8-yl)-2-methylpropanoate.

Step G: sodium (2S,3R)-methyl 3-cyclopropyl-3-((RS)-2-(4-(5-fluoro-2-methoxypyridin-4-yl)phenyl)-2,3,4,5-tetrahydrobenzo[b]oxepin-8-yl)-2-methylpropanoate To a solution of Peak 1 (faster eluting isomer) of (2S,3R)-methyl 3-cyclopropyl-3-(2-(4-(5-fluoro-2-methoxypyridin-4-yl)phenyl)-2,3,4,5-tetrahydro-benzo[b]oxepin-8-yl)-2-methylpropanoate (30 mg, 0.0613 mmol) in THF/MeOH/$H_2O$ (1.0 mL/1.0 mL/1.0 mL) was added LiOH (15.0 mg, 0.613 mmol). The reaction mixture was stirred at 50° C. for 16 hours, then cooled to room temperature, and acidified with HCl (1 mol/L) to pH 2. The mixture was extracted with EtOAc (2 mL×3), and the combined organic layers were concentrated in vacuo to afford a residue. The residue was purified by preparative HPLC (on a GILSON 281 instrument fitted with a Phenomenex Gemini $C_{18}$ (250*21.2 mm*5 um) using water and acetonitrile as the eluents. Mobile phase A: water (neutral), mobile phase B: acetonitrile. Gradient: 33-63% B, 0-10 min; 100% B, 10.5-12.5 min; 5% B, 13-15 min) to give (2S,3R)-3-cyclopropyl-3-(2-(2-fluoro-4-(2-methoxypyridin-4-yl)phenyl)-2,3,4,5-tetrahydro-benzo[b]oxepin-8-yl)-2-methylpropanoic acid (Example 5).

To a solution of (2S,3R)-3-cyclopropyl-3-(2-(2-fluoro-4-(2-methoxypyridin-4-yl)phenyl)-2,3,4,5-tetrahydrobenzo[b]oxepin-8-yl)-2-methylpropanoic acid (Example 5, 12.6 mg) in MeCN (0.5 mL) was added a solution of NaOH (aq. 172 mg, 0.5 M). The mixture was stirred for 1 hour at room temperature, then the reaction mixture was lyophilized to give the sodium salt of (2S,3R)-3-cyclopropyl-3-(2-(2-fluoro-4-(2-methoxypyridin-4-yl)phenyl)-2,3,4,5-tetrahydrobenzo[b]oxepin-8-yl)-2-methylpropanoic acid (Example 5). $^1$H NMR (400 MHz, $CDCl_3$): δ=8.13 (d, J=1.2 Hz, 1H), 7.64-7.58 (m, 4H), 7.12 (d, J=7.6 Hz, 1H), 6.88-6.83 (m, 3H), 4.69 (d, J=10.4 Hz, 1H), 3.98 (s, 3H), 2.97 (t, J=12.8 Hz, 1H), 2.82-2.78 (m, 2H), 2.21-2.11 (m, 3H), 1.94 (t, J=10.0 Hz, 1H), 1.75-1.66 (m, 1H), 1.10-1.08 (m, 1H), 0.98 (d, J=6.8 Hz, 3H), 0.62-0.61 (m, 1H), 0.37-0.32 (m, 2H), 0.03-0.02 (m, 1H). MS(ESI) m/z: 476.2 [M+H]$^+$.

To a solution of (2S,3R)-3-cyclopropyl-3-(2-(2-fluoro-4-(2-methoxypyridin-4-yl)phenyl)-2,3,4,5-tetrahydrobenzo[b]oxepin-8-yl)-2-methylpropanoic acid (12.6 mg) in MeCN (0.5 mL) was added the solution of NaOH (aq. 172 mg, 0.5 M), the mixture was stirred for 1 hour at 20° C. (room temperature). Then the reaction mixture was lyophilized to give the sodium salt of (2S,3R)-3-cyclopropyl-3-(2-(2-fluoro-4-(2-methoxypyridin-4-yl)phenyl)-2,3,4,5-tetrahydrobenzo[b]oxepin-8-yl)-2-methylpropanoic acid.

TABLE 3

Example 6 was prepared in a similar manner to Example 5 using the Peak 2, slower eluting isomer of Example 5, Step F as the starting material in Example 5, Step G.

| Example | Structure | MW | Compound Name | LC/MS (ESI) observed [M + 1]+ |
|---------|-----------|-----|---------------|-------------------------------|
| 6 | 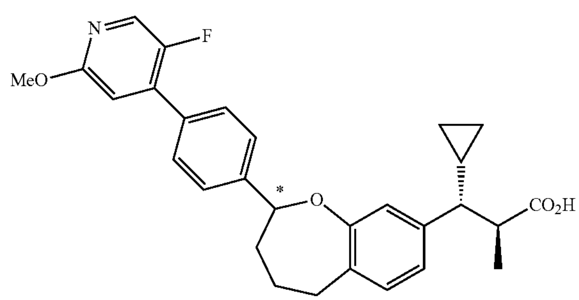 [SMILES: COc1cc(-c2ccc(C3CCCc4ccc([C@H](C5CC5)[C@H](C)C(=O)O)cc4O3)cc2)c(F)cn1] | 475.55 | (2S,3R)-3-cyclopropyl-3-((R or S)-2-(4-(5-fluoro-2-methoxypyridin-4-yl)phenyl)-2,3,4,5-tetrahydrobenzo[b]oxepin-8-yl)-2-methylpropanoic acid | 476.2 |

*stereoisomer at this position

EXAMPLE 7

(2S,3R)-3-cyclopropyl-3-((RS)-2-(5'-fluoro-2'-methoxy-[3,4'-bipyridin]-6-yl)-2,3,4,5-tetrahydrobenzo[b]oxepin-8-yl)-2-methylpropanoic acid

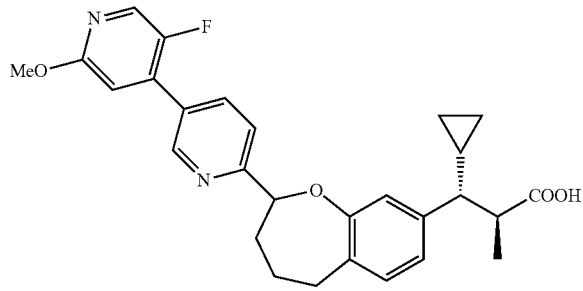 [SMILES: COc1cc(-c2ccc(C3CCCc4ccc([C@H](C5CC5)[C@H](C)C(=O)O)cc4O3)nc2)c(F)cn1]

Step A: 5'-fluoro-2'-methoxy-[3,4'-bipyridine]-6-carbaldehyde To a solution of compounds (5-fluoro-2-methoxypyridin-4-yl)boronic acid (1.00 g, 5.85 mmol) and 5-bromopicolinaldehyde (1.19 g, 6.44 mmol) in THF (10 mL) and water (2.0 mL) were added $K_2CO_3$ (2.42 g, 1.76 mmol) and $PdCl_2$(dppf) (428 mg, 0.585 mmol) under a $N_2$ atmosphere. The reaction mixture was stirred at 100° C. for 2 hours, then water (10 mL) was added and the mixture was extracted with EtOAc (2 mL×3). The combined organic layers were washed with brine (10 mL), dried over anhydrous $Na_2SO_4$ and filtered. The filtrate was concentrated in vacuo to give a residue, which was purified by preparative TLC (PE/EtOAc=5:1, v/v) to give the title compound. $^1$H NMR (400 MHz, $CDCl_3$): δ=10.2 (s, 1H), 8.99 (s, 1H), 8.17 (m, 3H), 6.88 (d, J=4.8 Hz, 1H), 3.98 (s, 3H). MS (ESI) m/z: 233.0 [M+H]$^+$.

Step B: 1-(5'-fluoro-2'-methoxy-[3,4'-bipyridin]-6-yl)but-3-en-1-ol To a solution of 5'-fluoro-2'-methoxy-[3,4'-bipyridine]-6-carbaldehyde (950 mg, 4.09 mmol) in THF (10 mL) was added allylmagnesium bromide (8.18 mL, 8.18 mmol) dropwise at 0° C. under a $N_2$ atmosphere. The reaction mixture was stirred for 30 min at 0° C. and 3 hours at room temperature. Then the reaction mixture was quenched with saturated $NH_4Cl$ (20 mL) and extracted with EtOAc (5.0 mL×3). The combined organic layers were washed with brine (30 mL), dried over anhydrous $Na_2SO_4$ and filtered. The filtrate was concentrated in vacuo to give a residue, which was purified by preparative TLC (PE:EtOAc=5:1, v/v) to give the title compound. $^1$H NMR (400 MHz, $CDCl_3$): δ=8.77 (s, 1H), 8.12 (s, 1H), 7.94 (d, J=4.8 Hz, 1H), 7.46 (d, J=4.2 Hz, 1H), 5.91-5.84 (m, 1H), 5.19-5.15 (m, 2H), 4.91-4.88 (m, 1H), 3.97 (s, 3H), 2.73-2.69 (m, 1H), 2.58-2.52 (m, 1H). MS(ESI) m/z: 275.1 [M+H]$^+$.

Step C: (2S,3R)-methyl 3-cyclopropyl-3-(4-((Z)-4-(5'-fluoro-2'-methoxy-[3,4'-bipyridin]-6-yl)-4-hydroxybut-1-en-1-yl)-3-hydroxyphenyl)-2-methylpropanoate To a solution of 1-(5'-fluoro-2'-methoxy-[3,4'-bipyridin]-6-yl)but-3-en-1-ol (320 mg, 1.17 mmol) and (2S, 3R)-methyl 3-cyclopropyl-3-(3-hydroxy-4-iodophenyl)-2-methyl-propanoate (280 mg, 0.778 mmol) in Toluene (10 mL) were added N-cyclohexyl-N-methylcyclohexanamine (229 mg, 1.17 mmol) and t-buxhos palladacycle (54.0 mg, 0.0778 mmol) under a $N_2$ atmosphere. The reaction mixture was stirred for 2 hours at 100° C., then cooled to room temperature and concentrated in vacuo to give a residue. The residue was purified via silica gel chromatography (eluted from PE:EtOAc=100:1 to 5:1, v/v) to give the title compound. $^1$H NMR (400 MHz, $CDCl_3$): δ=8.80 (s, 1H), 8.12 (s, 1H), 7.97 (d, J=8.4 Hz, 1H), 7.51 (d, J=8.0 Hz, 1H), 7.20 (d, J=8.0 Hz, 1H), 6.85 (d, J=5.2 Hz, 1H), 6.68-6.58 (m, 3H), 6.18-6.14 (m, 1H), 5.02 (s, 1H), 3.97 (s, 3H), 3.73 (s, 3H), 2.86-2.71 (m, 3H), 1.88-1.83 (m, 1H), 1.01 (s, 1H), 0.95 (d, J=6.8 Hz, 3H), 0.57-0.55 (m, 1H), 0.33-0.21 (m, 2H), 0.01-0.03 (m, 1H).

Step D: (2S,3R)-methyl 3-cyclopropyl-3-(4-(4-(5'-fluoro-2'-methoxy-[3,4'-bipyridin]-6-yl)-4-hydroxybutyl)-3-hydroxyphenyl)-2-methylpropanoate To a solution of (2S,3R)-methyl 3-cyclopropyl-3-(4-((Z)-4-(5'-fluoro-2'-methoxy-[3,4'-bipyridin]-6-yl)-4-hydroxybut-1-en-1-yl)-3-hydroxyphenyl)-2-methylpropanoate (290 mg, 0.572 mmol) in MeOH (10 mL) was added Pd(OH)$_2$/C (8.00 mg, 0.0572 mmol, 20%). The reaction mixture was stirred for 3 hours at room temperature under a $H_2$ balloon. Then the reaction mixture was filtered, and the filtrate was concentrated in vacuo to give the title compound, which was used in the next step.

Step E: (2S, 3R)-methyl 3-cyclopropyl-3-(2-(2-fluoro-4-(2-methoxypyridin-4-yl) phenyl)-2, 3, 4, 5-tetrahydrobenzo[b]oxepin-8-yl)-2-methylpropanoate To a solution of (2S, 3R)-methyl 3-cyclopropyl-3-(4-(4-(5'-fluoro-2'-methoxy-[3,4'-bipyridin]-6-yl)-4-hydroxybutyl)-3-hydroxyphenyl)-2-methylpropanoate (225 mg, 0.442 mmol) and triphenylphosphine (232 mg, 0.884 mmol) in DCM (3.0 mL) was added dropwise a solution of DIAD (179 mg, 0.884 mmol) in DCM (1.0 mL) at 0° C. under a $N_2$ atmosphere. The reaction mixture was stirred for 2 hours at room temperature, then concentrated in vacuo to give a residue, which was purified by preparative TLC (PE:EtOAc=5:1, v/v) to give the title compound. $^1$H NMR (400 MHz, $CDCl_3$): δ=8.78 (s, 1H), 8.13 (s, 1H), 8.01 (s, 1H), 7.86 (d, J=7.6 Hz, 1H), 7.13 (d, J=6.8 Hz, 1H), 6.86 (d, J=5.2 Hz, 1H), 6.82-6.81 (m, 3H), 4.77 (s, 1H), 3.97 (s, 3H), 3.71 (s, 3H), 2.84 (t, J=27.8 Hz, 1H), 2.83-2.77 (m, 2H), 2.48 (s, 1H), 1.87 (t, J=10.0 Hz, 1H), 1.74-1.70 (m, 1H), 1.03 (s, 1H), 0.94-0.92 (m, 3H), 0.54 (s, 1H), 0.33-0.21 (m, 2H), 0.02 (m, 1H). MS(ESI) m/z: 491.3 [M+H]$^+$.

Step F: (2S,3R)-methyl 3-cyclopropyl-3-((RS)-2-(5'-fluoro-2'-methoxy-[3,4'-bipyridin]-6-yl)-2,3,4,5-tetrahydrobenzo[b]oxepin-8-yl)-2-methylpropanoate

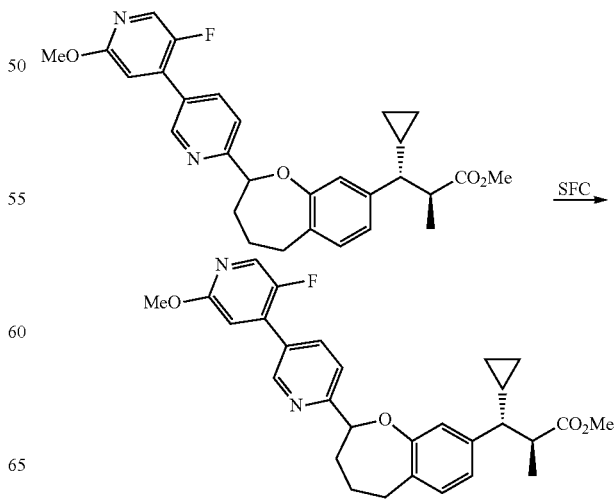

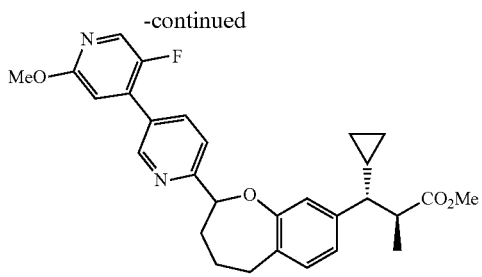

The (2S,3R)-methyl 3-cyclopropyl-3-((RS)-2-(5'-fluoro-2'-methoxy-[3,4'-bipyridin]-6-yl)-2,3,4,5-tetrahydrobenzo[b]oxepin-8-yl)-2-methylpropanoate (190 mg, 0.386 mmol) was separated by SFC (SFC conditions: Column: Chiralpak AD-3 50*4.6 mm I.D., 3 um Mobile phase: ethanol (0.05% DEA) in $CO_2$ from 5% to 40% Flow rate: 4 mL/min Wavelength: 220 nm) to give (2S,3R)-methyl 3-cyclopropyl-3-((R or S)-2-(5'-fluoro-2'-methoxy-[3,4'-bipyridin]-6-yl)-2,3,4,5-tetrahydrobenzo[b]oxepin-8-yl)-2-methylpropanoate (Peak 1, faster eluting isomer); and (2S,3R)-methyl 3-cyclopropyl-3-((R or S)-2-(5'-fluoro-2'-methoxy-[3,4'-bipyridin]-6-yl)-2,3,4,5-tetrahydrobenzo[b]oxepin-8-yl)-2-methylpropanoate (Peak 2, slower eluting isomer).

Step G: (2S,3R)-3-cyclopropyl-3-(2-(5'-fluoro-2'-methoxy-[3,4'-bipyridin]-6-yl)-2,3,4,5-tetrahydrobenzo[b]oxepin-8-yl)-2-methylpropanoic acid (Example 7) To a solution of Peak 1 (faster eluting isomer) of (2S,3R)-methyl 3-cyclopropyl-3-((R or S)-2-(5'-fluoro-2'-methoxy-[3,4'-bipyridin]-6-yl)-2,3,4,5-tetrahydro-benzo[b]oxepin-8-yl)-2-methylpropanoate (90.0 mg, 0.184 mmol) in THF/MeOH/$H_2O$ (1.0 mL/1.0 mL/1.0 mL) was added LiOH (44.0 mg, 1.84 mmol). The reaction mixture was stirred at 50° C. for 16 hours, then cooled to room temperature. The reaction mixture was acidified with HCl (1 mol/L) to pH 2 and extracted with EtOAc (2 mL×3). The combined organic layers were concentrated in vacuo to afford a residue, which was purified by preparative HPLC (on a GILSON 281 instrument fitted with a Phenomenex Gemini $C_{18}$ (250*21.2 mm*5 um) using Mobile phase A: water (neutral), mobile phase B: acetonitrile. Gradient: 33-63% B, 0-10 min; 100% B, 10.5-12.5 min; 5% B, 13-15 min) to give the title compound. $^1$H NMR (400 MHz, $CDCl_3$): δ=8.13 (d, J=1.2 Hz, 1H), 7.64-7.58 (m, 3H), 7.12 (d, J=7.6 Hz, 1H), 6.88-6.83 (m, 3H), 4.69 (d, J=10.8 Hz, 1H), 3.98 (s, 3H), 2.97 (t, J=12.8 Hz, 1H), 2.82-2.79 (m, 2H), 2.21-2.11 (m, 3H), 1.94 (t, J=10.0 Hz, 1H), 1.72-1.69 (m, 1H), 1.10-1.08 (m, 1H), 0.99 (d, J=6.8 Hz, 3H), 0.63-0.61 (m, 1H), 0.37-0.32 (m, 2H), 0.03-0.02 (m, 1H). MS(ESI) m/z: 477.2 [M+H]$^+$.

To a solution of (2S,3R)-3-cyclopropyl-3-(2-(2-fluoro-4-(2-methoxypyridin-4-yl)phenyl)-2,3,4,5-tetrahydrobenzo[b]oxepin-8-yl)-2-methylpropanoic acid (Example 7, 68.9 mg) in MeCN (0.5 mL) was added a solution of NaOH (aq. 172 mg, 0.5 M). The mixture was stirred for 1 hour at room temperature. Then the reaction mixture was lyophilized to give the sodium salt of the title compound.

TABLE 4

Example 8 was prepared in a similar manner to Example 7 using Peak 2, slower eluting isomer of Example 7 Step F as the starting material for Example 7 Step G.

| Example | Structure | MW | Compound Name | LC/MS (ESI) observed [M + 1]+ |
|---|---|---|---|---|
| 8 | 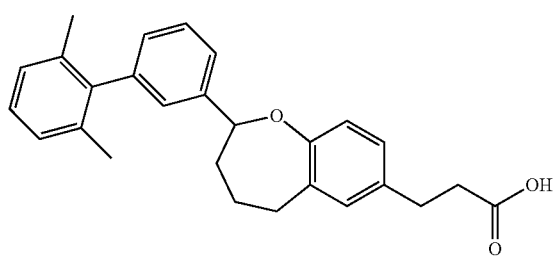 [SMILES: Cc1cccc(C)c1-c1cccc(C2CCCc3cc(CCC(=O)O)ccc3O2)c1] | 476.55 | (2S,3R)-3-cyclopropyl-3-((R or S)-2-(5'-fluoro-2'-methoxy-[3,4'-bipyridin]-6-yl)-2,3,4,5-tetrahydrobenzo[b]oxepin-8-yl)-2-methylpropanoic acid | 477.2 |

*stereoisomer at this position

EXAMPLE 9

3-(2-(2',6'-dimethyl-[1,1'-biphenyl]-3-yl)-2,3,4,5-tetrahydrobenzo[b]oxepin-7-yl)propanoic acid Step 1: 2',6'-dimethyl-[1,1'-biphenyl]-3-carbaldehyde To a degassed solution of 3-bromobenzaldehyde (500 mg, 2.70 mmol), (2,6-dimethylphenyl)boronic acid (608 mg, 4.05 mmol), and Pd(PPh$_3$)$_4$ (156 mg, 0.14 mmol) in dioxane (5 mL) was added $K_2CO_3$ (2N, 4.05 mL, 8.11 mmol). The reaction was heated to 100° C. After 16 h, the mixture was poured into NH$_4$Cl (sat, 25 mL) and extracted with EtOAc (2×25 mL). The combined organic layers were dried over MgSO$_4$ and concentrated. The resulting residue was purified by HPLC (ISCO 40 gram silica gel cartridge, 0 to 40% EtOAc/Hex) to give the title compound.

Step 2: 1-(2',6'-dimethyl-[1,1'-biphenyl]-3-yl)but-3-en-1-ol

To a solution of 2',6'-dimethyl-[1,1'-biphenyl]-3-carbaldehyde (850 mg, 4.04 mmol) in THF (10 mL) at 0° C. was added allyl Grignard (1M in THF, 4.85 mL). After 30 minutes, the reaction was quenched by the slow addition of 25 mL $NH_4C_1$ (saturated, aqueous). The mixture was extracted with EtOAc (2×25 mL). The combined organic layers were dried over $MgSO_4$ and concentrated. The resulting residue was purified by HPLC (40 gram silica gel ISCO cartridge, 0 to 40% EtOAc/hex) to give the title compound.

Step 3: 3'-(1-(4-bromo-2-vinylphenoxy)but-3-en-1-yl)-2,6-dimethyl-1,1'-biphenyl

To a solution of 1-(2',6'-dimethyl-[1,1'-biphenyl]-3-yl) but-3-en-1-ol (100 mg, 0.396 mmol), 4-bromo-2-vinylphenol (79 mg, 0.396 mmol), and triphenylphosphine (208 mg, 0.793 mmol) in toluene (4 mL) was slowly added DIAD (0.154 mL, 0.793 mmol) dropwise. After 16 h, the reaction was filtered and then concentrated. The resulting residue was purified by HPLC (40 gram silica gel ISCO cartridge, 0 to 40% EtOAc/hex) to give the title compound.

Step 4: 7-bromo-2-(2',6'-dimethyl-[1,1'-biphenyl]-3-yl)-2,3-dihydrobenzo[b]oxepine To a solution of 3'-(1-(4-bromo-2-vinylphenoxy)but-3-en-1-yl)-2,6-dimethyl-1,1'-biphenyl (28 mg, 0.065 mmol) in DCM (6 mL) was added Hoveyda-Grubbs Catalyst 2$^{nd}$ Generation (CAS #301224-40-8, 4 mg, 0.006 mmol) and the reaction was heated to reflux. After 1 hour, the reaction was cooled to room temperature, and the volatiles were removed in vacuo. The resulting residue was purified by HPLC (40 gram silica gel ISCO cartridge, 0 to 40% EtOAc/hex) to give the title compound.

Step 5: ethyl 3-(2-(2',6'-dimethyl-[1,1'-biphenyl]-3-yl)-2,3-dihydrobenzo[b]oxepin-7-yl)propanoate To a degassed solution of 7-bromo-2-(2',6'-dimethyl-[1,1'-biphenyl]-3-yl)-2,3-dihydrobenzo[b]oxepine (25 mg, 0.062 mmol) and Sphos Pd G2 (CAS #1028206-58-7, 4.7 mg, 0.006 mmol) in THF (3 mL) was added (3-ethoxy-3-oxopropyl)zinc(II) bromide (Rieke Metals, Inc., 0.5 M solution in THF, 0.370 mL, 0.185 mmol). The reaction was heated to 70° C. in a sealed vial with a teflon screw cap. After 16 h, the reaction was cooled to room temperature and then poured into $NH_4Cl$ (saturated, 25 mL). The mixture was extracted with EtOAc (2×25 mL). The combined organic layers were dried over $MgSO_4$ and concentrated. The resulting residue was purified by HPLC (40 gram silica gel ISCO cartridge, 0 to 40% EtOAc/hex) to give the title compound.

Step 6: 3-(2-(2',6'-dimethyl-[1,1'-biphenyl]-3-yl)-2,3-dihydrobenzo[b]oxepin-7-yl)propanoic acid To a slurry of ethyl 3-(2-(2',6'-dimethyl-[1,1'-biphenyl]-3-yl)-2,3-dihydrobenzo[b]oxepin-7-yl)propanoate (17 mg, 0.04 mmol) and THF (1 mL) in LiOH (10 mg, 0.40 mmol) was added MeOH (1 ml) and water (1 ml). The resulting mixture was heated to 60° C. After 1 hour, the reaction mixture was poured into 1N HCl (10 mL) and extracted with EtOAc (2×10 mL). The combined organic layers were dried over $MgSO_4$ and concentrated. The resulting residue was purified by HPLC (40 gram silica gel ISCO cartridge, 0 to 100% EtOAc/hex) to give the title compound. $^1$H NMR (500 MHz, $CDCl_3$) δ 7.48 (m, 2H), 7.22 (s, 1H), 7.18 (m, 1H), 7.15 (m, 3H), 7.03 (s, 1H), 6.99 (m, 2H), 6.40 (d, 1H), 6.01 (dd, 1H), 5.00 (d, 1H), 3.05 (dd, 1H), 2.95 t, 2H), 2.81 (dd, 1H), 2.70 (t, 2H), 2.07 (s, 6H); (m/z): 381.2 (M-18+H)$^+$.

Step 7: 3-(2-(2',6'-dimethyl-[1,1'-biphenyl]-3-yl)-2,3,4,5-tetrahydrobenzo[b]oxepin-7-yl)propanoic acid

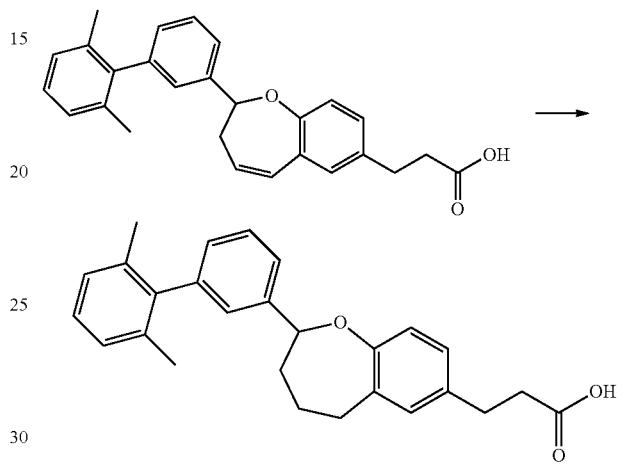

To a solution of 3-(2-(2',6'-dimethyl-[1,1'-biphenyl]-3-yl)-2,3-dihydrobenzo[b]oxepin-7-yl)propanoic acid (10 mg, 0.025 mmol) in EtOAc (1 mL) was added $Pd(OH)_2$ (1 mg, 20 wt %, 0.001 mmol). The mixture was vigorously stirred under a balloon of hydrogen gas. After 2 hours, the reaction was filtered through Celite™ and the filtrate concentrated to give the title compound. $^1$H NMR (500 MHz, $CDCl_3$) δ 7.48 (br, 2H), 7.21 (s, 1H), 7.10-7.20 (m, 4H), 7.01 (s, 1H), 6.98 (s, 2H), 4.62 (d, 1H), 3.00 (t, 1H), 2.92 (t, 2H), 2.78 (dd, 1H), 2.70 (t, 2H), 2.24-2.10 (m, 2H), 2.04 (s, 6H), 1.62 (q, 2H); (m/z): 383.4 (M-18+H)$^+$.

EXAMPLE 10

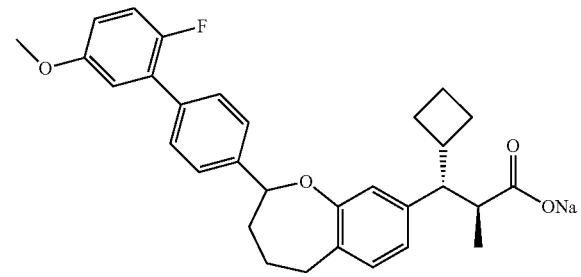

Sodium (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Isomer 1)

Step A: (2S,3R)-methyl 3-cyclobutyl-3-(4-(4-(2'-fluoro-5'-methoxy-[1,1'-biphenyl]-4-yl)-4-hydroxybutyl)-3-hydroxyphenyl)-2-methylpropanoate A solution of (2S,3R)-methyl 3-cyclobutyl-3-(4-((E)-4-(2'-fluoro-5'-methoxy-[1,1'-biphenyl]-4-yl)-4-hydroxybut-1-en-1-yl)-3-hydroxyphenyl)-2-methylpropanoate (550 mg, 1.061 mmol; prepared in a manner analogous to that in Example 5, Step C, but substituting (2S,3R)-methyl 3-cyclobutyl-3-(3-hydroxy-4-iodophenyl)-2-methylpropanoate for (2S, 3R)-methyl 3-cyclopropyl-3-(3-hydroxy-4-iodophenyl)-2-methylpropanoate) in anhydrous MeOH (27 mL) was transferred to a flask which was flushed with nitrogen. Then dry Pd/C (113 mg, 0.106 mmol) was added. The flask was evacuated and backfilled with hydrogen three times. The reaction was stirred at 15° C. under 1 atm of hydrogen for 16 hours. Then the catalyst was filtered off, and the filtrate was concentrated by rotary evaporator to give (2S,3R)-methyl 3-cyclobutyl-3-(4-(4-(2'-fluoro-5'-methoxy-[1,1'-biphenyl]-4-yl)-4-hydroxybutyl)-3-hydroxyphenyl)-2-methylpropanoate, which was used in the next step without further purification. $^1$H NMR (400 MHz, CDCl$_3$): δ=7.54 (d, J=7.0 Hz, 2H), 7.43 (d, J=8.2 Hz, 2H), 7.08 (t, J=9.4 Hz, 1H), 6.99 (d, J=8.2 Hz, 1H), 6.94 (dd, J=3.1, 6.3 Hz, 1H), 6.87-6.79 (m, 1H), 6.59 (d, J=7.4 Hz, 1H), 6.56-6.52 (m, 1H), 4.91-4.79 (m, 1H), 3.83 (s, 3H), 3.68 (s, 3H), 2.79-2.49 (m, 5H), 2.01-1.92 (m, 1H), 1.91-1.68 (m, 5H), 1.53-1.45 (m, 1H), 0.89 (d, J=6.8 Hz, 3H)

Step B: (2S,3R)-methyl 3-cyclobutyl-3-(2-(2'-fluoro-5'-methoxy-[1,1'-biphenyl]-4-yl)-2,3,4,5-tetrahydrobenzo[b]oxepin-8-yl)-2-methylpropanoate To a flask was added (2S, 3R)-methyl 3-cyclobutyl-3-(4-(4-(2'-fluoro-5'-methoxy-[1,1'-biphenyl]-4-yl)-4-hydroxybutyl)-3-hydroxyphenyl)-2-methylpropanoate (426 mg, 0.818 mmol) and triphenylphosphine (300 mg, 1.15 mmol) under a nitrogen atmosphere. Then anhydrous DCM (4 mL) was added via syringe, and the colorless solution was cooled to 0° C. A solution of DIAD (0.223 ml, 1.14 mmol) in DCM (2 mL) was added dropwise over 1 hour. The reaction was stirred at 15° C. for 12 hours. Then the reaction mixture was directly purified by preparative TLC (silica gel, PE:EtOAc=5:1, v/v) to give (2S,3R)-methyl 3-cyclobutyl-3-(2-(2'-fluoro-5'-methoxy-[1,1'-biphenyl]-4-yl)-2,3,4,5-tetrahydrobenzo[b]oxepin-8-yl)-2-methylpropanoate. $^1$H NMR (400 MHz, CDCl$_3$): δ=7.60 (d, J=7.8 Hz, 2H), 7.55 (d, J=7.8 Hz, 2H), 7.13-7.03 (m, 2H), 7.01-6.95 (m, 1H), 6.89-6.81 (m, 1H), 6.79-6.76 (m, 1H), 6.76-6.72 (m, 1H), 4.67-4.59 (m, 1H), 3.85 (s, 3H), 3.70-3.63 (m, 3H), 2.98 (t, J=13.2 Hz, 1H), 2.82-2.72 (m, 2H), 2.65-2.50 (m, 2H), 2.27-2.04 (m, 3H), 2.01-1.90 (m, 1H), 1.77-1.56 (m, 6H), 0.89-0.87 (m, 3H)

Step C: (2S,3R)-methyl 3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Faster Eluting Isomer) and (2S,3R)-methyl 3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Slower Eluting Isomer) (2 S,3R)-Methyl 3-cyclobutyl-3-(2-(2'-fluoro-5'-methoxy-[1,1'-biphenyl]-4-yl)-2,3,4,5-tetrahydrobenzo[b]oxepin-8-yl)-2-methylpropanoate (310 mg, 0.617 mmol) was separated by SFC (Column: Chrialpak AD (250 mm*30 mm, 5 m); Mobile phase: A: Supercritical CO$_2$, B: MeOH (0.05% NH$_3$H$_2$O), A:B=60:40 at 50 mL/min; Column Temp: 38° C.; Nozzle Pressure: 100 Bar; Wavelength: 220 nm) to afford (2S,3R)-methyl 3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpro-panoate (Faster Eluting Isomer) and (2S,3R)-methyl 3-cyclobutyl-3-((S or R)-2-(2'-fluoro-5'-methoxy-[1,1'-biphenyl]-4-yl)-2,3,4,5-tetrahydrobenzo[b]oxepin-8-yl)-2-methylpropanoate (Slower Eluting Isomer).

Step D: Sodium (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate To a solution of (2S,3R)-methyl 3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Faster eluting isomer from Step 3; 134 mg, 0.267 mmol) in THF (0.5 mL), MeOH (0.5 mL) and water (0.5 mL) was added lithium hydroxide monohydrate (112 mg, 2.67 mmol). The mixture was heated to 50° C. for 12 hours, and then acidified to pH 3 by adding concentrated aqueous HCl. The solvents were removed by rotary evaporator. The resulting residue was purified by preparative HPLC (preparative HPLC on a GILSON 281 instrument fitted with a YMC-Actus Triart C18 150*30 mm*5 m using water and acetonitrile as the eluents. mobile phase A: water (containing 0.1% TFA, v/v), mobile phase B: acetonitrile. Gradient: 52-82% B, 0-10 min; 100% B, 10.5-12.5 min; 5% B, 13-15 min) to give (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoic acid (Isomer 1). (2S,3R)-3-Cyclobutyl-3-((R)-2-(2'-fluoro-5'-methoxy-[1,1'-biphenyl]-4-yl)-2,3,4,5-tetrahydrobenzo[b]oxepin-8-yl)-2-methylpropanoic acid (Isomer 1, 67.2 mg, 0.138 mmol) was dissolved in 1 mL of acetonitrile. To the solution was added 276 mg of NaOH solution (2% wt/wt). The mixture was stirred at 15° C. for 2 h. The clear solution was freeze-dried to give sodium (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Isomer 1). MS (ESI) m/z: 511.2[M+Na]$^+$; $^1$H NMR (400 MHz, CDCl$_3$): δ=7.60 (d, J=8.0 Hz, 2H), 7.55 (d, J=8.0 Hz, 2H), 7.09-7.04 (m, 2H), 6.98-6.97 (m, 1H), 6.88-6.81 (m, 1H), 6.81-6.74 (m, 2H), 4.64 (d, J=9.6 Hz, 1H), 3.84 (s, 3H), 3.05-2.92 (m, 1H), 2.88-2.73 (m, 2H), 2.70-2.56 (m, 2H), 2.28-2.03 (m, 4H), 1.85-1.60 (m, 5H), 1.55-1.44 (m, 1H), 0.93 (d, J=7.2 Hz, 3H).

EXAMPLE 11

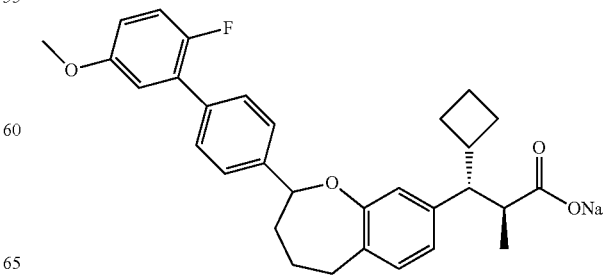

Sodium (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Isomer 2) Utilizing a method similar to that outlined in Step 4, Example 10, (2S,3R)-methyl 3-cyclobutyl-3-((S or R)-2-(2'-fluoro-5'-methoxy-[1,1'-biphenyl]-4-yl)-2,3,4,5-tetrahydro-benzo[b]oxepin-8-yl)-2-methylpropanoate (Slower Eluting Isomer) from Step 3, Example 10 was converted to Sodium (2S,3R)-3-cyclobutyl-3-((R or S)-2-(2'-fluoro-5'-methoxy-[1,1'-biphenyl]-4-yl)-2,3,4,5-tetrahydrobenzo[b]oxepin-8-yl)-2-methylpropanoate (Isomer 2). MS (ESI) m/z: 511.2 [M+Na]$^+$; $^1$H NMR (400 MHz, CDCl$_3$): δ=7.60 (d, J=8.4 Hz, 2H), 7.53 (d, J=8.2 Hz, 2H), 7.09-7.07 (m, 2H), 6.98-6.97 (m, 1H), 6.88-6.82 (m, 1H), 6.79-6.75 (m, 2H), 4.63 (d, J=10.0 Hz, 1H), 3.84 (s, 3H), 2.98-2.81 (m, 1H), 2.79-2.63 (m, 2H), 2.61-2.59 (m, 2H), 2.20-2.08 (m, 4H), 1.78-1.65 (m, 5H), 1.51-1.49 (m, 1H), 0.92 (d, J=6.4 Hz, 3H).

EXAMPLES 12 and 13

Example 12

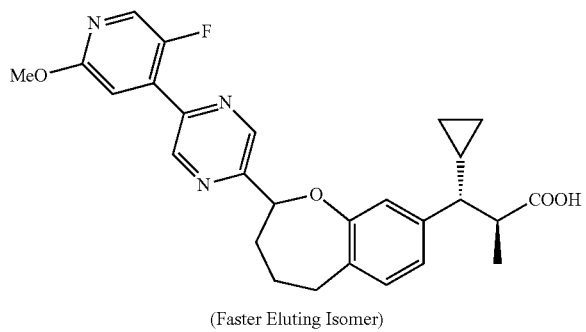

(Faster Eluting Isomer)

Example 13

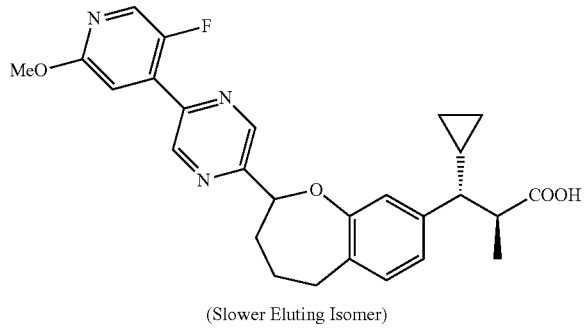

(Slower Eluting Isomer)

(2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoic acid (Faster Eluting Isomer) and (2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoic acid (Slower Eluting Isomer)

Step A: (5-(5-fluoro-2-methoxypyridin-4-yl)pyrazin-2-yl)methanol To a solution of (5-fluoro-2-methoxypyridin-4-yl) boronic acid (2.60 g, 15.2 mmol) and (5-chloropyrazin-2-yl)methanol (2.00 g, 13.8 mmol) in THF (10 mL) and water (2.0 mL) were added K$_3$PO$_4$ (8.80 g, 41.5 mmol) and PdCl$_2$(dppf) (1.01 g, 1.38 mmol) under a N$_2$ atmosphere. The reaction mixture was stirred at reflux with a 100° C. bath for 2 hours. Then the reaction mixture was added to water (10 mL) and extracted with EtOAc (2.0 mL×3). The combined organic layers were washed with brine (10 mL), dried over anhydrous Na$_2$SO$_4$ and filtered. The filtrate was concentrated in vacuo to give a residue, which was purified by preparative TLC (PE/EtOAc=5:1) to afford (5-(5-fluoro-2-methoxypyridin-4-yl)pyrazin-2-yl)methanol. MS(ESI) m/z: 236.0 [M+H]$^+$.

Step B: 5-(5-fluoro-2-methoxypyridin-4-yl) pyrazine-2-carbaldehyde To a solution of (5-(5-fluoro-2-methoxypyridin-4-yl) pyrazin-2-yl) methanol (1.56 g, 6.64 mmol) in DCM (20 mL) was added Dess-Martin Periodinane (4.22 g, 9.96 mmol) under a N$_2$ atmosphere. The reaction mixture was stirred for 2 hours at room temperature, then quenched with saturated Na$_2$S$_2$O$_3$ (30 mL) and extracted with DCM (10 mL×3). The combined organic layers were washed with aqueous NaOH (0.2 M, 50 mL), followed by brine (50 mL), dried over anhydrous Na$_2$SO$_4$ and filtered. The filtrate was concentrated in vacuo to give a residue, which was purified by silica gel chromatography (eluted from PE:EtOAc=100:1 to 20:1, v/v) to afford 5-(5-fluoro-2-methoxypyridin-4-yl) pyrazine-2-carbaldehyde. $^1$H NMR (400 MHz, CDCl$_3$): δ=10.23 (s, 1H), 9.31 (d, J=6.8 Hz, 2H), 8.22 (d, J=2.0 Hz, 1H), 7.49 (d, J=4.8 Hz, 1H), 3.99 (s, 3H). MS(ESI) m/z: 234.0 [M+H]$^+$ Step C: 1-(5-(5-fluoro-2-methoxypyridin-4-yl)pyrazin-2-yl)but-3-en-1-ol To a solution of 4-(5-fluoro-2-methoxypyridin-4-yl)benzaldehyde (900 mg, 3.86 mmol) in THF (10 mL) was added allylmagnesium bromide (1M in diethyl ether, 4.63 mL, 4.63 mmol) dropwise at 0° C. under a N$_2$ atmosphere. The reaction mixture was stirred for 30 min at 0° C. and 3 hours at room temperature. The reaction mixture was then quenched with saturated NH$_4$C$_1$ (20 mL) and extracted with EtOAc (5.0 mL×3). The combined organic layers were washed with brine (30 mL), dried over anhydrous Na$_2$SO$_4$ and filtered. The filtrate was concentrated in vacuo to give a residue, which was purified by preparative TLC (PE:EtOAc=5:1, v/v) to afford 1-(5-(5-fluoro-2-methoxypyridin-4-yl)pyrazin-2-yl)but-3-en-1-ol. $^1$H NMR (400 MHz, CDCl$_3$): δ=9.08 (s, 1H), 8.81 (s, 1H), 8.17 (d, J=2.4 Hz, 1H), 7.43 (s, J=4.8 Hz, 1H), 5.90-5.83 (m, 1H), 5.22-5.18 (m, 2H), 4.98 (s, 1H), 3.97 (s, 3H), 3.25 (s, 1H), 2.79-2.73 (m, 1H), 2.63-2.58 (m, 1H).
MS(ESI) m/z: 276.1 [M+H]$^+$ Step D: (2S,3R)-methyl 3-cyclopropyl-3-(4-((Z)-4-(5-(5-fluoro-2-methoxypyridin-4-yl)pyrazin-2-yl)-4-hydroxybut-1-en-1-yl)-3-hydroxyphenyl)-2-methylpropanoate To a solution of 1-(5-(5-fluoro-2-methoxypyridin-4-yl)pyrazin-2-yl)but-3-en-1-ol (532 mg, 1.93 mmol) and (2S, 3R)-methyl 3-cyclopropyl-3-(3-hydroxy-4-iodophenyl)-2-methylpropanoate (385 mg, 1.07 mmol) in toluene (10 mL) were added N-cyclohexyl-N-methylcyclohexanamine (377 mg, 1.93 mmol) and chloro[2-(di-tert-butylphosphino)-2',4',6'-triisopropyl-1,1'-biphenyl][2-(2-aminoethyl)-phenyl)]palladium(II) (73.5 mg, 0.107 mmol) under a N$_2$ atmosphere. The reaction mixture was stirred for 2 hours at 100° C., then cooled to room temperature and concentrated in vacuo to give a residue. The residue was purified by silica gel chromatography (eluted from PE:EtOAc=100:1 to 5:1, v/v) to afford (2S,3R)-methyl 3-cyclopropyl-3-(4-((Z)-4-(5-(5-fluoro-2-methoxypyridin-4-yl)pyrazin-2-yl)-4-hydroxybut-1-en-1-yl)-3-hydroxyphenyl)-2-methylpropanoate.
MS(ESI) m/z: 508.3 [M+H]$^+$; $^1$H NMR (400 MHz, CDCl$_3$): δ=9.08 (s, 1H), 8.86 (s, 1H), 8.16 (d, J=2.0 Hz, 1H), 7.43 (d, J=5.2 Hz, 1H), 7.25 (d, J=8.0 Hz, 1H), 6.72-6.62 (m, 3H), 6.23-6.16 (m, 1H), 5.06 (t, J=6.0 Hz, 1H), 3.97 (s, 3H), 3.73 (s, 3H), 2.93-2.76 (m, 3H), 2.18 (s, 3H), 1.87-1.82 (m, 2H), 1.01-0.93 (m, 4H), 0.56-0.55 (m, 1H), 0.34-0.31 (m, 1H), 0.24-0.21 (m, 1H), 0.01-0.03 (m, 1H).

Step E: (2S,3R)-methyl 3-cyclopropyl-3-(4-(4-(5-(5-fluoro-2-methoxypyridin-4-yl)pyrazin-2-yl)-4-hydroxybutyl)-3-hydroxyphenyl)-2-methylpropanoate To a solution of ((2S,3R)-methyl 3-cyclopropyl-3-(4-((Z)-4-(5-(5-fluoro-2-methoxypyridin-4-yl)pyrazin-2-yl)-4-hydroxybut-1-en-1-yl)-3-hydroxyphenyl)-2-methylpropanoate (510 mg, 1.01 mmol) in MeOH (10 mL) was added Pd(OH)$_2$/C (14.2 mg, 0.101 mmol, 20%). The reaction mixture was stirred for 3 hours at room temperature under an H$_2$ atmosphere (H$_2$ balloon). The reaction mixture was then filtered. The filtrate was concentrated in vacuo to give (2S,3R)-methyl 3-cyclopropyl-3-(4-(4-(5-(5-fluoro-2-methoxypyridin-4-yl)pyrazin-2-yl)-4-hydroxy-butyl)-3-hydroxyphenyl)-2-methylpropanoate, which was used in the next step without further purification. MS(ESI) m/z: 510.2 [M+H]; $^1$H NMR (400 MHz, CDCl$_3$): δ=9.07 (s, 1H), 8.79 (s, 1H), 8.17 (d, J=2.4 Hz, 1H), 7.42 (d, J=5.2 Hz, 1H), 7.04 (d, J=7.2 Hz, 2H), 6.66-6.62 (m, 2H), 5.94 (m, 1H), 5.04 (s, 1H), 3.97 (s, 3H), 3.73 (s, 3H), 3.50 (s, 2H), 2.80-2.86 (m, 4H), 2.04-1.81 (m, 6H), 1.03 (d, J=4.8 Hz, 1H), 0.94 (d, J=6.4 Hz, 6H), 0.24-0.20 (m, 2H), 0.02-0.01 (m, 1H).

Step F: (2S,3R)-methyl 3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoate To a solution of (2S,3R)-methyl 3-cyclopropyl-3-(4-(4-(5-(5-fluoro-2-methoxypyridin-4-yl)pyrazin-2-yl)-4-hydroxybutyl)-3-hydroxyphenyl)-2-methylpropanoate (495 mg, 0.972 mmol) and triphenylphosphine (509 mg, 1.94 mmol) in DCM (10 mL) was added dropwise a solution of DIAD (392 mg, 1.94 mmol) in DCM (1.0 mL) at 0° C. under a N$_2$ atmosphere. The reaction mixture was stirred for 2 hours at room temperature. Then the reaction mixture was concentrated in vacuo to give a residue, which was purified by silica gel preparative TLC (PE:EtOAc=5:1, v/v) to afford (2S,3R)-methyl 3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoate. MS(ESI) m/z: 492.3 [M+H]; $^1$H NMR (400 MHz, CDCl$_3$): δ=9.15 (s, 1H), 9.07 (s, 1H), 8.18 (s, 1H), 7.46 (d, J=4.8 Hz, 1H), 7.14 (d, J=6.0 Hz, 2H), 6.89-6.82 (m, 2H), 4.85-4.81 (m, 1H), 3.99 (s, 3H), 3.72 (s, 3H), 3.01 (t, J=13.2 Hz, 1H), 2.86-2.76 (m, 1H), 2.53 (d, J=13.2 Hz, 2H), 2.18-2.04 (m, 2H), 1.89 (t, J=10.4 Hz, 1H), 1.78 (q, J=12.0 Hz, 1H), 1.04-0.93 (m, 4H), 0.56-0.55 (m, 1H), 0.36-0.33 (m, 1H), 0.25-0.22 (m, 1H), 0.01-0.01 (m, 1H).

Step G: (2S,3R)-methyl 3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoate To a solution of compound ((2S,3R)-methyl 3-cyclopropyl-3-((R or S)-2-(5-(5-fluoro-2-methoxypyridin-4-yl)pyrazin-2-yl)-2,3,4,5-tetrahydrobenzo[b]oxepin-8-yl)-2-methylpropanoate (278 mg, 0.566 mmol) in THF/MeOH/H$_2$O (1.0 mL/1.0 mL/1.0 mL) was added LiOH (135 mg, 5.66 mmol). The reaction mixture was stirred at 50° C. for 16 hours. After the mixture was cooled to room temperature, the reaction mixture was acidified to pH=2 with 1N HCl$_{(aq.)}$ and extracted with EtOAc (2.0 mL×3). The combined organic layers were concentrated in vacuo to afford a residue which was purified by preparative HPLC (on a GILSON 281 instrument fitted with a Phenomenex Gemini C$_{18}$ (250*21.2 mm*5 um) using water and acetonitrile as the eluents. Mobile phase A: water (neutral), mobile phase B: acetonitrile. Gradient: 33-63% B, 0-10 min; 100% B, 10.5-12.5 min; 5% B, 13-15 min) to give compound (2S,3R)-3-cyclopropyl-3-((R S)-2-(4-(5-fluoro-2-methoxypyridin-4-yl)phenyl)-2,3,4,5-tetrahydrobenzo[b]oxepin-8-yl)-2-methylpropanoic acid.

Step H: (2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoic acid (Example 12, Faster Eluting Isomer) and (2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoic acid (Example 13, Slower Eluting Isomer) (2S,3R)-3-Cyclopropyl-3-((RS)-2-(4-(5-fluoro-2-methoxypyridin-4-yl)phenyl)-2,3,4,5-tetrahydrobenzo[b]oxepin-8-yl)-2-methylpropanoic acid (248 mg, 0.520 mmol) was subjected to chiral SFC purification (Column: Chiralpak AD-3 50*4.6 mm I.D., 3 um Mobile phase: ethanol (0.05% DEA) in CO$_2$ from 5% to 40% Flow rate: 4 mL/min Wavelength: 220 nm) to afford (2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methylpropanoic acid (Example 12, Faster Eluting Isomer) and (2S,3R)-3-cyclopropyl-3-((RS)-2-(5-(5-fluoro-2-methoxypyridin-4-yl)pyrazin-2-yl)-2,3,4,5-tetrahydrobenzo[b]oxepin-8-yl)-2-methyl-propanoic acid (Example 13, Slower Eluting Isomer). Example 12 (Faster Eluting Isomer): MS(ESI) m/z: 478.2[M+H]; 1H NMR (400 MHz, CDCl$_3$): δ=9.16 (s, 1H), 9.07 (s, 1H), 8.18 (d, J=1.6 Hz, 1H), 7.45 (d, J=4.8 Hz, 1H), 7.15 (d, J=8.0 Hz, 1H), 6.90-6.86 (m, 2H), 4.84 (d, J=10.8 Hz, 1H), 3.99 (s, 3H), 3.04 (t, J=13.6 Hz, 1H), 2.85-2.79 (m, 2H), 2.52 (d, J=13.6 Hz, 3H), 1.94 (t, J=10.0 Hz, 1H), 2.16-1.99 (m, 2H), 1.94 (t, J=10.0 Hz, 1H), 1.96-1.75 (m, 1H), 1.11-0.98 (m, 4H), 0.62-0.60 (m, 1H), 0.37-0.36 (m, 2H), 0.03-0.02 (m, 1H). Example 13 (Slower Eluting Isomer): MS(ESI) m/z: 478.2 [M+H]; 1H NMR (400 MHz, CDCl$_3$): δ=9.16 (s, 1H), 9.07 (s, 1H), 8.18 (d, J=1.6 Hz, 1H), 7.45 (d, J=4.8 Hz, 1H), 7.15 (d, J=8.0 Hz, 1H), 6.90-6.86 (m, 2H), 4.84 (d, J=10.8 Hz, 1H), 3.99 (s, 3H), 3.04 (t, J=13.6 Hz, 1H), 2.85-2.79 (m, 2H), 2.52 (d, J=13.6 Hz, 3H), 1.94 (t, J=10.0 Hz, 1H), 2.16-1.99 (m, 2H), 1.94 (t, J=10.0 Hz, 1H), 1.96-1.75 (m, 1H), 1.11-0.98 (m, 4H), 0.62-0.60 (m, 1H), 0.37-0.36 (m, 2H), 0.03-0.02 (m, 1H). Example 12 (faster eluting isomer) and Example 13 (slower eluting isomer) may be converted to the sodium salt by the following method. To a solution of Example 12 (92 mg, 0.078 mmol) in MeCN (0.5 mL) was added a solution of NaOH (aq. 172 mg, 0.5 M), the mixture was stirred for 1 hour at 20° C. (room temperature). Then the reaction mixture was frozen and lyophilized to give the sodium salt of Example 12. The sodium salt of Example 13 may be prepared using the same method starting with Example 13 (slower eluting isomer).

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:
Human and mouse GPR40 stable cell-lines were generated in CHO cells stably expressing NFAT BLA (Beta-lactamase). A human GPR40 stable cell-line was generated in HEK cells stably expressing the acquorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μL medium/well. The cells were incubated with 20 μl/well of the assay buffer (HBSS, 0.1% BSA, 20 mM HEPES, 2.5 mM probenecid, pH 7.4) containing 8 μM fluo-4,AM, 0.08% pluronic acid at room temperature for 100 minutes. Fluorescence output was measured using FLIPR. Compounds were dissolved in DMSO and diluted to desired concentrations with assay buffer. 13.3 μL/well of compound solution was added. The FLIPR Assay $EC_{50}$ values for specific compounds are listed in Table I.

Inositol Phosphate Turnover (IP1) Assay:

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% CO2 incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is acoustically transferred to the appropriate well in the assay cell plate. The plates are then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay. The Inositol Phosphate Turnover (IP1) Assay $EC_{50}$ values for specific compounds are listed in Table I.

The compounds of the present invention, including the compounds in Examples 1-13, have either $EC_{50}$ values less than 10 micromolar (μM) in the FLIPR assay described above, or have $EC_{50}$ values less than 6500 nanomolar (nM) in the Inositol Phosphate Turnover (IP1) Assay described above.

TABLE I

| Example No. | Stereoisomers | Human FLIPR $EC_{50}$, nM or % activation | Human IP1 Assay, EC50, nM |
| --- | --- | --- | --- |
| 1 | Isomer A[a] | ND | 3.6 |
| 2 | Isomer B[a] | ND | 14 |
| 3 | Isomer A[b] | ND | 13 |
| 4 | Isomer B[b] | ND | 27 |
| 5 | Isomer A[a] | ND | 3.1 |
| 6 | Isomer B[a] | ND | 5.2 |
| 7 | Isomer A[a] | ND | 3.0 |
| 8 | Isomer B[a] | ND | 29 |
| 9 | Mix of isomers | 3300 | ND |
| 10 | Isomer A[a] | ND | 4.6 |
| 11 | Isomer B[a] | ND | 6.0 |

TABLE I-continued

| Example No. | Stereoisomers | Human FLIPR $EC_{50}$, nM or % activation | Human IP1 Assay, EC50, nM |
| --- | --- | --- | --- |
| 12 | Isomer A[b] | ND | 116 |
| 13 | Isomer B[b] | ND | 684 |

*Isomer A = first eluting peak from chiral column;
Isomer B = second eluting peak from chiral column;
"ND" is not determined;
[a]Isomers separated at methyl ester stage;
[b]Isomers separated at carboxylic acid stage.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

The invention claimed is:

1. A compound of structural formula I:

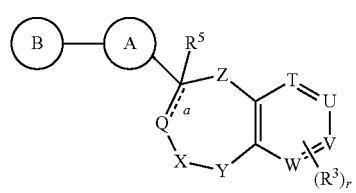

I or a pharmaceutically acceptable salt thereof; wherein
"a" is a single bond;
T is CH;
U is $CR^1$;
V is $CR^2$;
W is CH;

Q is selected from the group consisting of: —CR$^4$R$^6$;
X is selected from the group consisting of: —CR$^9$R$^9$;
Y is selected from the group consisting of: —CR$^9$R$^9$;
Z is oxygen;
A is selected from the group consisting of:
  (1) aryl,
  (2) heteroaryl,
  (3) C$_{3-6}$cycloalkyl, and
  (4) C$_{2-5}$cycloheteroalkyl,
wherein A is unsubstituted or substituted with one to five substituents selected from R$^a$;
B is selected from the group consisting of:
  (1) hydrogen,
  (2) aryl,
  (3) aryl-O—,
  (4) aryl-C$_{1-10}$ alkyl-,
  (5) aryl-C$_{1-10}$ alkyl-O—,
  (6) C$_{3-6}$cycloalkyl,
  (7) C$_{3-6}$cycloalkyl-C$_{1-10}$alkyl-,
  (8) C$_{3-6}$cycloalkyl-C$_{1-10}$alkyl-O—,
  (9) C$_{3-6}$cycloalkenyl,
  (10) C$_{3-6}$cycloalkenyl-C$_{1-10}$alkyl-,
  (11) C$_{3-6}$cycloalkenyl-C$_{1-10}$alkyl-O—,
  (12) C$_{2-5}$cycloheteroalkyl,
  (13) C$_{3-6}$cycloheteroalkyl-C$_{1-10}$alkyl-,
  (14) C$_{3-6}$cycloheteroalkyl-C$_{1-10}$alkyl-O—,
  (15) heteroaryl,
  (16) heteroaryl-O—,
  (17) heteroaryl-C$_{1-10}$ alkyl-, and
  (18) heteroaryl-C$_{1-10}$ alkyl-O—,
wherein B is unsubstituted or substituted with one to five substituents selected from R$^b$;
R$^1$ and R$^2$ are each independently selected from:
  (1) a bond,
  (2) hydrogen,
  (3) halogen,
  (4) —OR$^k$,
  (5) —CN,
  (6) —C$_{1-6}$alkyl,
  (7) —C$_{3-6}$cycloalkyl,
  (8) —C$_{3-6}$cycloalkyl-C$_{1-3}$alkyl-,
  (9) —C$_{2-6}$cycloheteroalkyl, and
  (10) —C$_{2-6}$cycloheteroalkyl-C$_{1-3}$alkyl-,
wherein each alkyl, cycloalkyl and cycloheteroalkyl is unsubstituted or substituted with one to three substituents selected from R$^L$, and wherein one of R$^1$ and R$^2$ is substituted with a substituent selected from R$^7$,
or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N-Rg, wherein each R$^1$ and R$^2$ is unsubstituted or substituted with one to three substituents selected from R$^L$, and wherein one of R$^1$ and R$^2$ is substituted with a substituent selected from R$^7$;
R$^3$ is absent or selected from the group consisting of:
  (1) hydrogen,
  (2) halogen,
  (3) —OR$^e$,
  (4) —CN,
  (5) —C$_{1-6}$alkyl,
  (6) —C$_{3-6}$cycloalkyl, and
  (7) —C$_{3-6}$cycloalkyl-C$_{1-3}$alkyl-,
wherein each alkyl and cycloalkyl is unsubstituted or substituted with one to three substituents selected from R$^i$;

R$^4$ is selected from the group consisting of:
  (1) hydrogen,
  (2) halogen,
  (3) OR$^e$,
  (4) C$_{0-5}$alkylNR$^c$R$^d$,
  (5) C$_{1-6}$alkyl,
  (6) C$_{1-6}$alkyl-O—,
  (7) C$_{3-6}$cycloalkyl,
  (8) C$_{3-6}$cycloalkyl-O—,
  (9) C$_{3-6}$cycloalkyl-C$_{1-10}$alkyl-,
  (10) C$_{3-6}$cycloalkyl-C$_{1-10}$alkyl-O—,
  (11) C$_{2-5}$cycloheteroalkyl,
  (12) C$_{2-5}$cycloheteroalkyl-O—,
  (13) C$_{2-5}$cycloheteroalkyl-C$_{1-10}$ alkyl-,
  (14) C$_{2-5}$ cycloheteroalkyl-C$_{1-10}$ alkyl-O—,
  (15) aryl,
  (16) aryl-O—,
  (17) aryl-C$_{1-10}$alkyl-,
  (18) heteroaryl,
  (19) heteroaryl-O—, and
  (20) heteroaryl-C$_{1-10}$alkyl-,
wherein each alkyl, cycloalkyl, cycloheteroalkyl, aryl and heteroaryl is unsubstituted or substituted with one to three substituents selected from R$^j$;
R$^5$ is selected from the group consisting of:
  (1) hydrogen,
  (2) —C$_{1-6}$alkyl, and
  (3) —C$_{3-6}$cycloalkyl,
wherein each alkyl and cycloalkyl is unsubstituted or substituted with one to three substituents selected from R$^j$;
R$^6$ is selected from the group consisting of:
  (1) hydrogen,
  (2) —C$_{1-6}$alkyl, and
  (3) —C$_{3-6}$cycloalkyl,
wherein each alkyl and cycloalkyl is unsubstituted or substituted with one to three substituents selected from R$^j$;
R$^7$ is selected from the group consisting of:
  (1) —CO$_2$R$^8$,
  (2) —C$_{1-6}$alkyl-CO$_2$R$^8$,
  (3) —C$_{1-6}$alkyl-CONHSO$_2$R$^m$,
  (4) —C$_{1-6}$alkyl-SO$_2$NHCOR$^m$,
  (5) —C$_{1-6}$alkyl-tetrazolyl, and
  (6) a cycloheteroalkyl selected from the group consisting of:

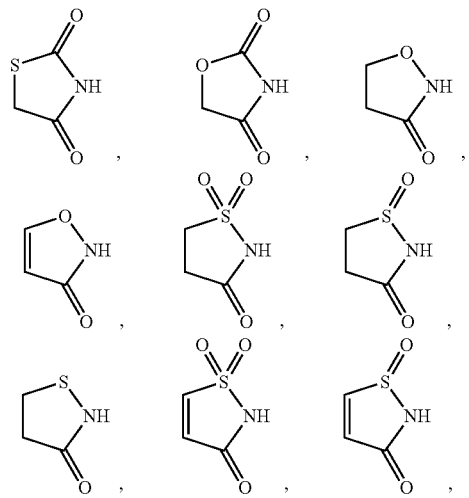

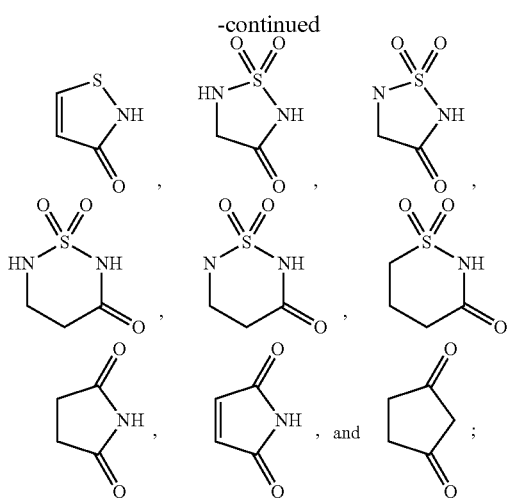

R[8] is selected from the group consisting of:
 (1) hydrogen,
 (2) —$C_{1-6}$alkyl,
 (3) —$C_{3-6}$cycloalkyl, and
 (4) aryl-$C_{1-6}$alkyl,
wherein each alkyl, cycloalkyl and aryl is unsubstituted or substituted with one to three substituents selected from R[j];

R[9] is selected from the group consisting of:
 (1) hydrogen,
 (2) —$C_{1-6}$alkyl,
 (3) halogen,
 (4) —$(CH_2)_{0-5}$OH,
 (5) —$(CH_2)_{0-5}$ $OC_{1-6}$alkyl,
 (6) —$(CH_2)_{0-5}$ $NR^cR^d$,
 (7) —$C_{3-6}$cycloalkyl, and
 (8) aryl-$C_{1-6}$alkyl,
wherein each $CH_2$, alkyl, cycloalkyl and aryl is unsubstituted or substituted with one to three substituents selected from R[j];

R[a] is selected from the group consisting of:
 (1) —$C_{1-6}$alkyl,
 (2) halogen,
 (3) —$C_{0-6}$alkyl-OR[e],
 (4) —$C_{0-6}$alkyl-$NR^cS(O)_nR^e$,
 (5) —$C_{0-6}$alkyl-$S(O)_nR^e$,
 (6) —$C_{0-6}$alkyl-$S(O)_nNR^cR^d$,
 (7) —$C_{0-6}$alkyl-$NR^cR^d$,
 (8) —$C_{0-6}$alkyl-$C(O)R^e$,
 (9) —$C_{0-6}$alkyl-$OC(O)R^e$,
 (10) —$C_{0-6}$alkyl-$CO_2R^e$,
 (11) —$C_{0-6}$alkyl-CN,
 (12) —$C_{0-6}$alkyl-$C(O)NR^cR^d$,
 (13) —$C_{0-6}$alkyl-$NR^cC(O)R^e$,
 (14) —$C_{0-6}$alkyl-$NR^cC(O)OR^e$,
 (15) —$C_{0-6}$alkyl-$NR^cC(O)NR^cR^d$,
 (16) —$CF_3$,
 (17) —$OCF_3$,
 (18) —$OCHF_2$,
 (19) —$C_{0-6}$alkyl-aryl,
 (20) —$C_{0-6}$alkyl-heteroaryl,
 (21) —$C_{0-6}$alkyl-$C_{3-10}$cycloalkyl,
 (22) —$C_{0-6}$alkyl-$C_{3-10}$cycloalkenyl, and
 (23) —$C_{0-6}$alkyl -$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alky, —CN, —$OCHF_2$, —$OCF_3$, —$CF_3$, and —$C_{0-6}$alkyl-$NR^cR^d$;

R[b] is independently selected from the group consisting of:
 (1) —$C_{1-10}$alkyl,
 (2) —$C_{2-10}$alkenyl,
 (3) —$CF_3$,
 (4) halogen,
 (5) —CN,
 (6) —OH,
 (7) —$OC_{1-10}$alkyl,
 (8) —$OC_{2-10}$alkenyl,
 (9) —$O(CH_2)_pOC_{1-10}$alkyl,
 (10) —$O(CH_2)_pC_{3-6}$cycloalkyl,
 (11) —$O(CH_2)_pC_{3-6}$cycloalkyl-$C_{1-10}$alkyl-,
 (12) —$O(CH_2)_pC_{2-5}$cycloheteroalkyl,
 (13) —$O(CH_2)_pC_{2-5}$cyclohereroalkyl-$C_{1-10}$alkyl-,
 (14) —O-aryl,
 (15) —O-heteroaryl,
 (16) —O-aryl-$C_{1-10}$alkyl-,
 (17) —O-heteroaryl-$C_{1-10}$alkyl-,
 (18) —$O(CH_2)_pNR^cS(O)_mR^e$,
 (19) —$O(CH_2)_pS(O)_mR^e$,
 (20) —$O(CH_2)_pS(O)_mNR^cR^d$,
 (21) —$O(CH_2)_pNR^cR^d$,
 (22) —$C(O)R^e$,
 (23) —$OC(O)R^e$,
 (24) —$CO_2R^e$,
 (25) —$C(O)NR^cR^d$,
 (26) —$NR^cC(O)R^e$,
 (27) —$NR^cC(O)OR^e$,
 (28) —$NR^cC(O)NR^cR^d$,
 (29) —$O(CH_2)_pO$—$C_{3-6}$cycloalkyl,
 (30) —$O(CH_2)_pO$—$C_{2-5}$cycloheteroalkyl,
 (31) —$OCF_3$,
 (32) —$OCHF_2$,
 (33) —$(CH_2)_pC_{3-6}$cycloalkyl,
 (34) —$(CH_2)_pC_{2-5}$cycloheteroalkyl,
 (35) aryl,
 (36) heteroaryl,
 (37) aryl-$C_{1-10}$alkyl-, and
 (38) heteroaryl-$C_{1-10}$alkyl-,
wherein each CH, $CH_2$, alkyl, alkenyl, cycloalkyl, cycloheteroalkyl, aryl and heteroaryl is unsubstituted or substituted with one to five substituents independently selected from: —$C_{1-6}$alkyl, halogen, OH, —O—$C_{1-6}$alkyl and —$CF_3$;

R[c] and R[d] are each independently selected from the group consisting of:
 (1) hydrogen,
 (2) $C_{1-10}$alkyl,
 (3) $C_{2-10}$alkenyl,
 (4) $C_{3-6}$cycloalkyl,
 (5) $C_{3-6}$ cycloalkyl-$C_{1-10}$alkyl-,
 (6) $C_{2-5}$cycloheteroalkyl,
 (7) $C_{2-5}$cycloheteroalkyl-$C_{1-10}$alkyl-,
 (8) aryl,
 (9) heteroaryl,
 (10) aryl-$C_{1-10}$alkyl-, and
 (11) heteroaryl-$C_{1-10}$alkyl-,
wherein each alkyl, alkenyl, cycloalkyl, cycloheteroalkyl, aryl and heteroaryl is unsubstituted or substituted with one to three substituents independently selected from R[f],
or R[c] and R[d] together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$;

each $R^e$ is independently selected from the group consisting of:
(1) hydrogen,
(2) —$C_{1-10}$alkyl,
(3) —$C_{2-10}$alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) aryl-$C_{1-10}$alky-,
(10) heteroaryl, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;

each $R^f$ is selected from the group consisting of:
(1) halogen,
(2) $C_{1-10}$alkyl,
(3) —OH,
(4) —O—$C_{1-4}$alkyl,
(5) —$S(O)_m$-$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;

each $R^g$ is selected from the group consisting of:
(1) hydrogen,
(2) —$C(O)R^e$, and
(3) —$C_{1-10}$alkyl,
wherein each alkyl is unsubstituted or substituted with one to five halogens;

each $R^h$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;

$R^i$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

$R^j$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

each $R^k$ is independently selected from the group consisting of:
(1) hydrogen,
(2) —$C_{1-6}$ alkyl,
(3) —$C_{1-6}$alkyl-$SO_2C_{1-6}$alkyl,
(4) —$CF_3$, and
(5) —$CHF_2$,
wherein each alkyl is unsubstituted or substituted with one to three substituents independently selected from: —OH, —$OC_{1-6}$alkyl, halogen, cyano, and —$S(O)_2C_{1-6}$alkyl;

each $R^L$ is independently selected from the group consisting of:
(1) —$CO_2C_{1-6}$alkyl,
(2) —$C_{1-10}$alkyl,
(3) —$C_{2-10}$ alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with one to four substituents independently selected from $C_{1-6}$alkyl, halogen, and —$OC_{1-6}$alkyl;

each $R^m$ is independently selected from the group consisting of:
(1) —$C_{1-10}$alkyl,
(2) —$C_{2-10}$ alkenyl,
(3) —$C_{3-6}$ cycloalkyl,
(4) —$C_{3-6}$ cycloalkyl-$C_{1-10}$alkyl-,
(5) —$C_{2-5}$cycloheteroalkyl,
(6) —$C_{2-5}$ cycloheteroalkyl-$C_{1-10}$alkyl-,
(7) aryl,
(8) heteroaryl,
(9) aryl-$C_{1-10}$alkyl-, and
(10) heteroaryl-$C_{1-10}$alkyl-;

each n is independently selected from: 0, 1 or 2;
each m is independently selected from: 0, 1 or 2;

each p is independently selected from: 0, 1, 2, 3, 4, 5 or 6; and each r is independently selected from: 0, 1, 2 or 3.

2. The compound according to claim 1 wherein A is selected from the group consisting of:
   (1) aryl,
   (2) heteroaryl, and
   (3) $C_{2-5}$cycloheteroalkyl,
wherein each aryl, heteroaryl and cycloheteroalkyl is unsubstituted or substituted with one to five substituents selected from $R^a$; or a pharmaceutically acceptable salt thereof.

3. The compound according to claim 1 wherein A is selected from the group consisting of:
   (1) phenyl,
   (2) pyridyl, and
   (3) azetidine,
wherein each phenyl, pyridyl and azetidine is unsubstituted or substituted with one to five substituents selected from $R^a$; or a pharmaceutically acceptable salt thereof.

4. The compound according to claim 1 wherein B is selected from the group consisting of:
   (1) aryl,
   (2) aryl-$C_{1-10}$ alkyl-, and
   (3) heteroaryl,
wherein each alkyl, aryl and heteroaryl is unsubstituted or substituted with one to five substituents selected from $R^b$; or a pharmaceutically acceptable salt thereof.

5. The compound according to claim 1 wherein B is selected from the group consisting of:
   (1) phenyl,
   (2) —$CH_2$-phenyl, and
   (3) pyridyl,
wherein each phenyl and pyridyl is unsubstituted or substituted with one to five substituents selected from $R^b$; or a pharmaceutically acceptable salt thereof.

6. The compound according to claim 1 wherein $R^1$ and $R^2$ are each independently selected from:
   (1) hydrogen, and
   (2) —$C_{1-6}$alkyl,
wherein each alkyl is unsubstituted or substituted with one to three substituents selected from $R^L$, and wherein one of $R^1$ and $R^2$ is substituted with a substituent selected from $R^7$; or a pharmaceutically acceptable salt thereof.

7. The compound according to claim 1 wherein $R^1$ and $R^2$ are each independently selected from:
   (1) hydrogen, and
   (2) —$C_2$alkyl,
wherein each alkyl is unsubstituted or substituted with one to three substituents selected from $R^L$, and wherein one of $R^1$ and $R^2$ is substituted with a substituent selected from $R^7$; or a pharmaceutically acceptable salt thereof.

8. The compound according to claim 1 wherein
$R^3$ is absent or hydrogen;
$R^4$ is hydrogen;
$R^5$ is hydrogen; and
$R^6$ is hydrogen;
or a pharmaceutically acceptable salt thereof.

9. The compound according to claim 1 wherein $R^7$ is —$CO_2R^8$; or a pharmaceutically acceptable salt thereof.

10. The compound according to claim 1 wherein $R^8$ is hydrogen; or a pharmaceutically acceptable salt thereof.

11. The compound according to claim 1 wherein $R^9$ is hydrogen; or a pharmaceutically acceptable salt thereof.

12. The compound according to claim 1 of structural Formula Ia:

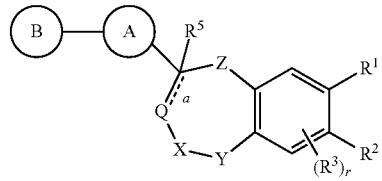

wherein
"a" is a single bond;
Q is selected from the group consisting of: —$CR^4R^6$;
X is selected from the group consisting of: —$CR^9R^9$;
Y is selected from the group consisting of: —$CR^9R^9$;
Z is oxygen;
A is selected from the group consisting of:
   (1) aryl,
   (2) heteroaryl, and
   (3) $C_{2-5}$cycloheteroalkyl,
wherein each aryl, heteroaryl and cycloheteroalkyl is unsubstituted or substituted with one to five substituents selected from $R^a$;
B is selected from the group consisting of:
   (1) aryl,
   (2) aryl-$C_{1-10}$ alkyl-, and
   (3) heteroaryl,
wherein each alkyl, aryl and heteroaryl is unsubstituted or substituted with one to five substituents selected from $R^b$;
$R^1$ and $R^2$ are each independently selected from:
   (1) hydrogen, and
   (2) —$C_{1-6}$alkyl,
wherein each alkyl is unsubstituted or substituted with one to three substituents selected from $R^L$, and wherein one of $R^1$ and $R^2$ is substituted with a substituent selected from $R^7$;
$R^3$ is absent or hydrogen;
$R^4$ is hydrogen;
$R^5$ is hydrogen;
$R^6$ is hydrogen;
$R^7$ is —$CO_2R^8$;
$R^8$ is hydrogen;
$R^9$ is hydrogen;
each $R^L$ is independently selected from the group consisting of: —$C_{1-10}$alkyl, and -$C_{3-6}$cycloalkyl, wherein each alkyl, and cycloalkyl is unsubstituted or substituted with one to four substituents independently selected from $C_{1-6}$alkyl, halogen, and —$OC_{1-6}$alkyl; and
each r is independently selected from: 0, 1, 2 or 3;
or a pharmaceutically acceptable salt thereof.

13. The compound according to claim 1 of structural Formula Ia:

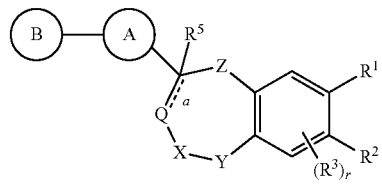

wherein
"a" is a single bond;
Q is selected from the group consisting of: —CR$^4$R$^6$;
X is selected from the group consisting of: —CR$^9$R$^9$;
Y is selected from the group consisting of: —CR$^9$R$^9$;
Z is oxygen;
A is selected from the group consisting of:
  (1) phenyl,
  (2) pyridyl, and
  (3) azetidine,
wherein each phenyl, pyridyl and azetidine is unsubstituted or substituted with one to five substituents selected from R$^a$;
B is selected from the group consisting of:
  (1) phenyl,
  (2) —CH$_2$-phenyl, and
  (3) pyridyl,
wherein each phenyl and pyridyl is unsubstituted or substituted with one to five substituents selected from R$^b$;
R$^1$ and R$^2$ are each independently selected from:
  (1) hydrogen, and
  (2) —C$_2$alkyl,
wherein each alkyl is unsubstituted or substituted with one to three substituents selected from R$^L$, and wherein one of R$^1$ and R$^2$ is substituted with a substituent selected from R$^7$;
R$^3$ is absent or hydrogen;
R$^4$ is hydrogen;
R$^5$ is hydrogen;
R$^6$ is hydrogen;
R$^7$ is —CO$_2$R$^8$;
R$^8$ is hydrogen;
R$^9$ is hydrogen;
each R$^L$ is independently selected from the group consisting of: —CH$_3$, and —cyclopropyl; and
each r is independently selected from: 0, 1, 2 or 3;
or a pharmaceutically acceptable salt thereof.

14. The compound according to claim 13 selected from:

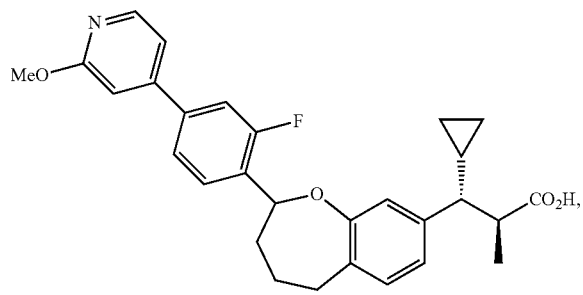

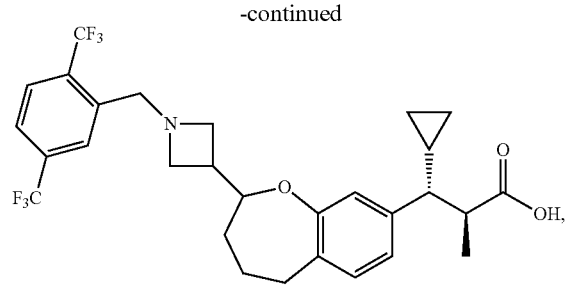

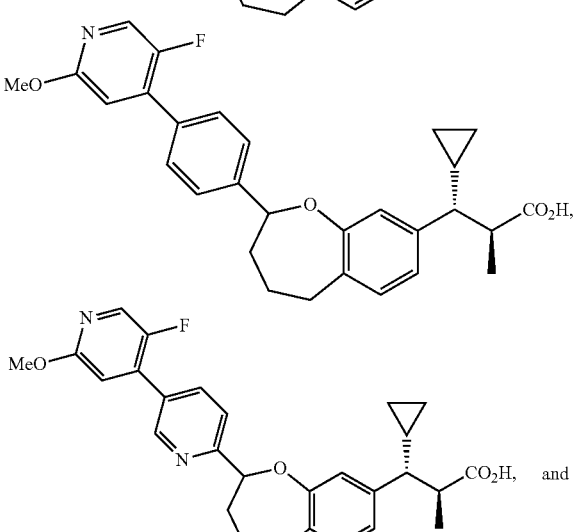

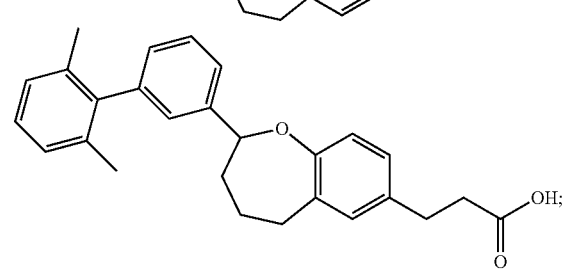

or a pharmaceutically acceptable salt thereof.

15. A pharmaceutical composition comprising a compound of claim 1, or a pharmaceutically acceptable salt thereof, and a pharmaceutically acceptable carrier.

16. A method of treating type 2 diabetes mellitus in a patient in need of treatment comprising the administration to the patient of a therapeutically effective amount of a compound of claim 1, or a pharmaceutically acceptable salt thereof.

* * * * *